(12) United States Patent
Labadie et al.

(10) Patent No.: US 8,071,797 B2
(45) Date of Patent: Dec. 6, 2011

(54) HETEROCYCLIC ANTIVIRAL COMPOUNDS

(75) Inventors: Sharada Shenvi Labadie, Sunnyvale, CA (US); Clara Jeou Jen Lin, Palo Alto, CA (US); Francisco Xavier Talamas, Mountain View, CA (US); Robert James Weikert, Boulder Creek, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 536 days.

(21) Appl. No.: 12/378,346

(22) Filed: Feb. 12, 2009

(65) Prior Publication Data

US 2009/0208449 A1 Aug. 20, 2009

Related U.S. Application Data

(60) Provisional application No. 61/028,629, filed on Feb. 14, 2008, provisional application No. 61/138,603, filed on Dec. 18, 2008.

(51) Int. Cl.
*C07D 307/00* (2006.01)
*A61K 31/34* (2006.01)

(52) U.S. Cl. ........ 549/468; 549/469; 549/470; 514/469; 514/489

(58) Field of Classification Search .................. 549/468, 549/469, 470; 514/469, 489
See application file for complete search history.

(56) References Cited

U.S. PATENT DOCUMENTS

| 7,265,152 B2 | 9/2007 | Saha et al. |
| 2007/0224167 A1 | 9/2007 | Emini et al. |
| 2007/0231318 A1 | 10/2007 | Saha et al. |

FOREIGN PATENT DOCUMENTS

| WO | WO 2008/100867 A2 | 8/2008 |
| WO | WO 2008/100867 A3 | 8/2008 |

*Primary Examiner* — Andrew D Kosar
*Assistant Examiner* — Raymond Covington
(74) *Attorney, Agent, or Firm* — Brian L. Buckwalter

(57) ABSTRACT

Compounds having the formula I wherein $R^1$, $R^2$, $R^3$, $R^4$, $R^5$ and X are as defined herein are Hepatitis C virus NS5b polymerase inhibitors. Also disclosed are compositions and methods for treating an HCV infection and inhibiting HCV replication.

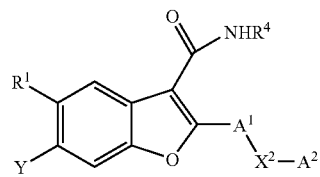

20 Claims, No Drawings

HETEROCYCLIC ANTIVIRAL COMPOUNDS

CROSS REFERENCE TO PRIOR APPLICATIONS

This application claims the benefit of priority to U.S. Ser. No. 61/028,629 filed Feb. 14, 2008 and to U.S. Ser. No. 61/138,603 filed Dec. 18, 2008 both of which are hereby incorporated by reference in their entirety.

FIELD OF THE INVENTION

The present invention provides non-nucleoside compounds and certain derivatives thereof which are inhibitors of RNA-dependent RNA viral polymerase. These compounds are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND

Hepatitis C virus is the leading cause of chronic liver disease throughout the world. (Boyer, N. et al., *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family *Flaviviridae* that includes the genera flaviviruses, pestiviruses, and hapaceiviruses which includes hepatitis C viruses (Rice, C. M., *Flaviviridae*: The viruses and their replication. In: Fields Virology, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a highly conserved 5' untranslated region (UTR), a long open reading frame encoding a polyprotein precursor of approximately 3011 amino acids, and a short 3' UTR.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forns and J. Bukh, *Clinics in Liver Disease* 1999 3:693-716; J. Bukh et al., *Semin. Liv. Dis.* 1995 15:41-63). Unfortunately Type 1 infectious is more resistant to therapy than either type 2 or 3 genotypes (N. N. Zein, *Clin. Microbiol. Rev.*, 2000 13:223-235).

Viral structural proteins include a nucleocapsid core protein (C) and two envelope glycoproteins, E1 and E2. HCV also encodes two proteases, a zinc-dependent metalloproteinase encoded by the NS2—NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of non-structural protein 5) remain unknown. It is believed that most of the non-structural proteins encoded by the HCV RNA genome are involved in RNA replication Currently a limited number of approved therapies are available for the treatment of HCV infection. New and existing therapeutic approaches for treating HCV infection and inhibiting of HCV NS5B polymerase activity have been reviewed: R. G. Gish, *Sem. Liver. Dis.*, 1999 19:5; Di Besceglie, A. M. and Bacon, B. R., *Scientific American*, October: 1999 80-85; G. Lake-Bakaar, Current and Future Therapy for Chronic Hepatitis C Virus Liver Disease, *Curr. Drug Targ. Infect Dis.* 2003 3(3):247-253; P. Hoffmann et al., Recent patent on experimental therapy for hepatitis C virus infection (1999-2002), *Exp. Opin. Ther. Patents* 2003 13(11):1707-1723; M. P. Walker et al., Promising Candidates for the treatment of chronic hepatitis C, *Exp. Opin. Investing. Drugs* 2003 12(8): 1269-1280; S.-L. Tan et al., Hepatitis C Therapeutics: Current Status and Emerging Strategies, *Nature Rev. Drug Discov.* 2002 1:867-881; J. Z. Wu and Z. Hong, Targeting NS5B RNA-Dependent RNA Polymerase for Anti-HCV Chemotherapy, *Curr. Drug Targ.—Infect. Dis.* 2003 3(3):207-219.

Ribavirin (1-((2R,3R,4S,5R)-3,4-Dihydroxy-5-hydroxymethyl-tetrahydro-furan-2-yl)-1H-[1,2,4]triazole-3-carboxylic acid amide; Virazole®) is a synthetic, non-interferon-inducing, broad-spectrum antiviral nucleoside analog. Ribavirin has in vitro activity against several DNA and RNA viruses including *Flaviviridae* (Gary L. Davis. *Gastroenterology* 2000 118:S104-S114). Although, in monotherapy ribavirin reduces serum amino transferase levels to normal in 40% of patients, it does not lower serum levels of HCV-RNA. Ribavirin also exhibits significant toxicity and is known to induce anemia. Viramidine is a ribavirin prodrug converted to ribavirin by adenosine deaminase to in hepatocytes. (J. Z. Wu, *Antivir. Chem. Chemother.* 2006 17(1):33-9)

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon beta, type 2 includes interferon gamma. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (Davis, Luke-Bakaar, supra)

One limitation of early IFN therapy was rapid clearance of the protein from the blood. Chemical derivatization of IFN with polyethyleneglycol (PEG) has resulted in proteins with substantially improved pharmacokinetic properties. PEGASYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release* 2001 72:217-224).

Combination therapy of HCV with ribavirin and interferon-α currently is the optimal therapy for HCV. Combining ribavirin and PEG-IFN (infra) results in a sustained viral response (SVR) in 54-56% of patients with type 1 HCV. The SVR approaches 80% for type 2 and 3 HCV. (Walker, supra) Unfortunately, combination therapy also produces side effects which pose clinical challenges. Depression, flu-like symptoms and skin reactions are associated with subcutaneous IFN-α and hemolytic anemia is associated with sustained treatment with ribavirin.

A number of potential molecular targets for drug development as anti-HCV therapeutics have now been identified including, but not limited to, the NS2—NS3 autoprotease, the NS3 protease, the NS3 helicase and the NS5B polymerase. The RNA-dependent RNA polymerase is absolutely essential for replication of the single-stranded, positive sense, RNA genome. This enzyme has elicited significant interest among medicinal chemists.

Nucleoside inhibitors can act either as a chain terminator or as a competitive inhibitor that interferes with nucleotide binding to the polymerase. To function as a chain terminator the nucleoside analog must be taken up by the cell in vivo and be converted in vivo to its triphosphate form to compete as a substrate at the polymerase nucleotide binding site. This conversion to the triphosphate is commonly mediated by cellular kinases which impart additional structural limitations on any nucleoside. In addition this requirement for phosphorylation limits the direct evaluation of nucleosides as inhibitors of HCV replication to cell-based assays (J. A. Martin et al., U.S. Pat. No. 6,846,810; C. Pierra et al., *J. Med. Chem.* 2006 49(22):6614-6620; J. W. Tomassini et al., *Antimicrob. Agents and Chemother.* 2005 49(5):2050; J. L. Clark et al., *J. Med. Chem.* 2005 48(17):2005).

Compounds of the present invention and their isomeric forms and pharmaceutically acceptable salts thereof are also useful in treating and preventing viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and antiinfective compounds. Such combination therapy may also comprise providing a compound of the invention either concurrently or sequentially with other medicinal agents or potentiators, such as ribavirin and related compounds, amantadine and related compounds, various interferons such as, for example, interferon-alpha, interferon-beta, interferon gamma and the like, as well as alternate forms of interferons such as pegylated interferons. Additionally combinations of ribavirin and interferon, may be administered as an additional combination therapy with at least one of the compounds of the present invention.

Other interferons currently in development include albinterferon-α-2b (Albuferon), IFN-omega with DUROS, LOCTERON™ and interferon-α-2b XL. As these and other interferons reach the marketplace their use in combination therapy with compounds of the present invention is anticipated.

HCV polymerase inhibitors are another target for drug discovery and compounds in development include R-1626, R-7128, IDX184/IDX102, PF-868554 (Pfizer), VCH-759 (ViroChem), GS-9190 (Gilead), A-837093 and A-848837 (Abbot), MK-3281 (Merck), GSK949614 and GSK625433 (Glaxo), ANA598 (Anadys), VBY 708 (ViroBay).

Inhibitors of the HCV NS3 protease also have been identified as potentially useful for treatment of HCV. Protease inhibitors in clinical trials include VX-950 (Telaprevir, Vertex), SCH503034 (Broceprevir, Schering), TMC435350 (Tibotec/Medivir) and ITMN-191 (Intermune). Other protease inhibitors in earlier stages of development include MK7009 (Merck), BMS-790052 (Bristol Myers Squibb), VBY-376 (Virobay), IDXSCA/IDXSCB (Idenix), BI12202 (Boehringer), VX-500 (Vertex), PHX1766 Phenomix).

Other targets for anti-HCV therapy under investigation include cyclophilin inhibitors which inhibit RNA binding to NS5b, nitazoxanide, Celgosivir (Migenix), an inhibitor of α-glucosidase-1, caspase inhibitors, Toll-like receptor agonists and immunostimulants such as Zadaxin (SciClone).

SUMMARY OF THE INVENTION

There is currently no preventive treatment of Hepatitis C virus (HCV) and currently approved therapies, which exist only against HCV, are limited. Design and development of new pharmaceutical compounds is essential.

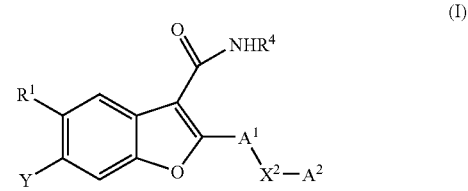

(I)

The present invention provides a compound according to formula I, or a pharmaceutically acceptable salt thereof, and the use of such compounds for the treatment of a host infected with HCV wherein:

$A^1$ is phenylene or pyridinylene;

$A^2$ is phenyl or pyridinyl either optionally substituted with 1 to 3 groups independently selected from the group consisting of halogen, $C_{1-6}$ alkyl, $C_{1-6}$ haloalkyl, cyano and $C_{1-6}$ alkoxy;

$R^1$ is hydrogen, $C_{1-10}$ alkyl, $C_{3-7}$ cycloalkyl, $C_{1-10}$ alkoxy or halogen;

Y is $NR^2R^3$, $C_{1-6}$ hydroxyalkyl, $C_{1-6}$ acyl or heteroaryl selected from the group consisting of pyrrolyl, pyrazolyl or isoxazolyl said heteroaryl optionally substituted by one or two groups selected from $C_{1-3}$ alkyl, $C_{1-3}$ haloalkyl, $C_{1-3}$ alkoxy, halogen or pyrrolidinyl wherein the nitrogen atom is optionally substituted by $C_{1-6}$ acyl or $C_{1-6}$ alkylsulfonyl;

either (i) $R^2$ is (a) hydrogen,
(b) $C_{1-10}$ alkyl,
(c) $C_{1-10}$ alkyl substituted by one to four groups selected independently in each occurrence from hydroxy, $NR^{7b}R^{8b}$, $C_{1-3}$ alkoxy, halogen or cyano;
(d) $R^{11}S(=O)_m[C(R_5)_2]_{1-6}$ wherein $R^{11}$ is $C_{1-6}$ alkyl or $NR^{7c}R^{8c}$;
(e) $C_{1-3}$ alkyl-$S(=O)_2NH$—$[C(R^5)_2]_{1-6}$;
(f) $R^{7b}R^{8b}NC(=O)$—$[C(R^5)_2]_{1-6}$;
(g) $C_{3-6}$ cycloalkyl optionally substituted by —OH, $C_{1-3}$ alkoxy or —$NR^{7b}R^{8b}$;
(h) heterocyclyl;
(i) heterocyclyl-$C_{1-6}$alkyl;
(j) heteroaryl-$C_{1-6}$ alkyl;
(k) $C_{1-6}$ acyl optionally substituted with $C_{1-6}$ alkylsulfonyl;
(l) $(CH_2)_pCOX^3$ wherein p is one to six and $X^3$ is hydroxy, $C_{1-6}$ alkoxy or $NR^{7c}R^{8c}$;
wherein said heterocyclyl moiety is oxetanyl, tetrahydrofuranyl, tetrahydropyranyl, azetidinyl, pyrrolidinyl or piperidinyl, oxazolidin-2-on-4-yl and said heteroaryl moiety is pyridinyl or pyrimidinyl and said heterocyclyl or heteroaryl groups are optionally substituted with optionally substituted by —OH, $C_{1-3}$ alkoxy, $C_{1-3}$ alkyl or —$NR^{7b}R^{8b}$;

$R^3$ is hydrogen, $C_{1-10}$ alkyl, $S(=O)_2R^6$, $S(=O)_2NR^{7a}R^{8a}$, $C_{1-6}$ acyl or $C(=O)NR^{7a}R^{8a}$; or, (ii) $R^2$ and $R^3$ together are $(CH_2)_2X^1(CH_2)_2$, $(CH_2)_{3-4}S(=O)_2$, $(CH_2)_{2-3}NR^{10}S(=O)_2$;

$R^4$ and $R^5$ are independently in each occurrence hydrogen or $C_{1-6}$ alkyl;

$R^6$ is $C_{1-6}$ alkyl or $C_{3-7}$ cycloalkyl;

$R^{7a}$ and $R^{8a}$ are (i) independently hydrogen, $C_{1-6}$ alkyl, $C_{1-6}$ hydroxyalkyl $C_{1-6}$ haloalkyl or (ii) $R^{7a}$ and $R^{8a}$ together are $(CH_2)_2X^1(CH_2)_2$;

$R^{7b}$, $R^{8b}$ and $R^{10}$ are independently hydrogen, $C_{1-6}$ alkyl, $C_{1-6}$ acyl or $C_{1-6}$ alkylsulfonyl, $R^{7c}$ and $R^{8c}$ are independently hydrogen or $C_{1-3}$ alkyl;

$R^9$ is hydrogen $C_{1-3}$ acyl, $C_{1-3}$ alkylsulfonyl or $C_{1-3}$ alkyl;

$R^{10}$ is hydrogen or $C_{1-6}$ alkyl;

$X^1$ is —O—, —$NR^9$—, —$S(O)_m$—, $(CH_2)_n$;

$X^2$ is $NHR^5$ or O;

m and n are independently in each occurrence an integer from 0 to 2; or, a pharmaceutically acceptable salts thereof.

The present invention also provides compositions comprising compounds of the present invention optionally including at least one pharmaceutically acceptable carrier, excipient or diluent for the treatment of HCV infection in the manufacture of a medicament for the treatment or prophylaxis HCV in a host.

Combination therapy has proven useful for the treatment of viral disease and new compounds synergistic with other approved and investigational HCV therapeutics and the present invention provides for treatment of HCV with nucleosides as described herein, or a pharmaceutically acceptable salt thereof, one or more other effective antiviral agent(s) or immunomodulators, optionally including at least one pharmaceutically acceptable carrier, excipient or diluent in combination with compounds according to formula I.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "optional bond" means that the bond may or may not be present, and that the description includes single, double, or triple bonds. If a substituent is designated to be a "bond" or "absent", the atoms linked to the substituents are then directly connected.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's The Pharmacological Basis of Therapeutics, 10th Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

As used herein, unless specifically indicated otherwise, the word "or" is used in the "inclusive" sense of "and/or" and not the "exclusive" sense of "either/or".

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

It will be understood that the subject to which a compound of the invention is administered need not suffer from a specific traumatic state. Indeed, the compounds of the invention may be administered prophylactically, prior to any development of symptoms. The term "therapeutic", "therapeutically", and permutations of these terms are used to encompass therapeutic, palliative as well as prophylactic uses. Hence, as used herein, by "treating or alleviating the symptoms" is meant reducing, preventing, and/or reversing the symptoms of the individual to which a compound of the invention has been administered, as compared to the symptoms of an individual receiving no such administration.

When any variable (e.g., $R^1$, $R^{4a}$, Ar, $X^1$ or Het) occurs more than one time in an constituent or in any formula depicting and describing compounds employed or claimed in the present invention, its definition on each occurrence is independent of its definition at every other occurrence. Also, combinations of substituents and/or variables are permissible only if such compounds result in stable compounds. A "stable" compound is a compound which can be prepared and isolated and whose structure and properties remain or can be made to remain essentially unchanged for a period of time sufficient to allow the use of the compound for the purposes described herein (e.g., therapeutic or prophylactic administration to a subject).

Unless expressly stated to the contrary, all ranges cited herein are inclusive. For example, a heterocyclic ring described as containing "1 to 4 heteroatoms" means the ring can contain 1, 2, 3 or 4 heteroatoms. It is also to be understood that any range cited herein includes within its scope all of the subranges within that range. Thus, for example, an aryl or a heteroaryl described as optionally substituted with "from 1 to 5 substituents" is intended to include as aspects thereof, any aryl optionally substituted with 1 to 4 substituents, 1 to 3 substituents, 1 to 2 substituents, 2 to 5 substituents, 2 to 4 substituents, 2 to 3 substituents, 3 to 5 substituents, 3 to 4 substituents, 4 to 5 substituents, 1 substituent, 2 substituents, 3 substituents, 4 substituents, and 5 substituents.

In one embodiment of the present invention there is provided a compound according to formula I wherein A1, A2, R1, R2, R3, R4, R5, R6, R7, R7a, R7b, R7c, R8, R8a, R8b, R8c, R9, R10, R11, X1, X2, Y, m and n are as defined hereinabove.

In another embodiment of the present invention there is provided a compound according to formula I wherein $A^1$ is para-phenylene or para-pyridinylene, $A^2$, $R^1$, $R^2$, $R^3$, $R^4$, $R^5$, $R^6$, $R^7$, $R^{7a}$, $R^{7b}$, $R^{7c}$, $R^8$, $R^{8a}$, $R^{8c}$, $R^9$, $R^{10}$, $R^{11}$, $X^1$, $X^2$, $X^3$, Y, m, n and p are as defined hereinabove.

In a second embodiment of the present invention there is provided a compound according to formula I wherein Y is $NR^2R^3$ and $A^1$ is para-phenylene.

In a third embodiment of the present invention there is provided a compound according to formula I wherein Y is $NR^2R^3$ and $R^3$ is $S(=O)_2R^6$ and $R^6$ is $C_{1-6}$ alkyl.

In another embodiment of the present invention there is provided a compound according to formula I wherein Y is $NR^2R^3$ and $R^3$ is $S(=O)_2R^6$ and $R^6$ is $C_{3-7}$ cycloalkyl.

In a fourth embodiment of the present invention there is provided a compound according to formula I wherein Y is $NR^2R^3$, $R^2$ is $R^{11}S(=O)_m[C(R^5)_2]_{1-6}$, $R^3$ is $S(=O)_2R^6$, $R^6$ is $C_{1-6}$ alkyl and $R^{11}$ is $C_{1-6}$ alkyl or $NR^7NR^{8c}$.

In a another embodiment of the present invention there is provided a compound according to formula I wherein Y is $NR^2R^3$, $R^2$ is $R^{11}S(=O)_m[C(R^5)_2]_{1-6}$, $R^3$ is $S(=O)_2R^6$, $R^6$ is $C_{1-6}$ alkyl and $R^{11}$ is $NR^7NR^{8c}$.

In yet another embodiment of the present invention there is provided a compound according to formula I wherein Y is $NR^2R^3$, $R^2$ is $R^{11}S(=O)_m[C(R^5)_2]_{1-6}$, $R^3$ is $S(=O)_2R^6$, $R^6$ is $C_{1-6}$ alkyl, $R^{11}$ is $C_{1-6}$ alkyl or $NR^7NR^X$, $A^1$ is phenylene and $A^2$ is phenyl.

In a fifth embodiment of the present invention there is provided a compound according to formula I wherein Y is $NR^2R^3$, $R^2$ is $R^{11}S(=O)_m[C(R^5)_2]_{1-6}$, $R^3$ is $S(=O)_2R^6$, $R^6$ is $C_{1-6}$ alkyl and $R^{11}$ is $C_{1-6}$ alkyl.

In a sixth embodiment of the present invention there is provided a compound according to formula I wherein Y is $NR^2R^3$, $R^2$ is $C_{1-10}$ alkyl substituted by one to four groups selected independently in each occurrence from hydroxy, $NR^{7b}R^{8b}$, $C_{1-3}$ alkoxy, halogen or cyano, $R^3$ is $S(=O)_2R^6$ and $R^6$ is $C_{1-6}$ alkyl.

In another embodiment of the present invention there is provided a compound according to formula I wherein Y is $NR^2R^3$, $R^2$ is $C_{1-10}$ alkyl substituted by one to four groups selected independently in each occurrence from hydroxy, $NR^{7b}R^{8b}$, $C_{1-3}$ alkoxy, halogen or cyano, $R^3$ is $S(=O)_2R^6$, $R^6$ is $C_{1-6}$ alkyl, $A^1$ is phenylene and $A^2$ is phenyl.

In a seventh embodiment of the present invention there is provided a compound according to formula I wherein Y is $NR^2R^3$, $R^2$ is $C_{1-10}$ alkyl substituted a hydroxy or a $NR^{7b}R^{8b}$ moiety, $R^3$ is $S(=O)_2R^6$ and $R^6$ is $C_{1-6}$ alkyl.

In a eighth embodiment of the present invention there is provided a compound according to formula I wherein Y is $NR^2R^3$, $R^2$ is $C_{1-10}$ alkyl substituted by a $NR^{7b}R^{8b}$ moiety, $R^3$ is $S(=O)_2R^6$, $R^6$ is $C_{1-6}$ alkyl and $R^{7b}$ is $C_{1-6}$ alkylsulfonyl or $C_{1-6}$ acyl.

In a ninth embodiment of the present invention there is provided a compound according to formula I wherein Y is $NR^2R^3$, $R^2$ is heterocyclyl or heterocyclyl-$C_{1-6}$ alkyl, $R^3$ is $S(=O)_2R^6$, $R^6$ is $C_{1-6}$ alkyl and $R^{7b}$ is $C_{1-6}$ alkylsulfonyl or $C_{1-6}$ acyl.

In another embodiment of the present invention there is provided a compound according to formula I wherein Y is $NR^2R^3$, $R^2$ is heterocyclyl or heterocyclyl-$C_{1-6}$ alkyl wherein the heterocycle is an optionally substituted oxetanyl, tetrahydrofuranyl or tetrahydropyranyl, $R^3$ is $S(=O)_2R^6$, $R^6$ is $C_{1-6}$ alkyl and $R^{7b}$ is $C_{1-6}$ alkylsulfonyl or $C_{1-6}$ acyl.

In another embodiment of the present invention there is provided a compound according to formula I wherein Y is $NR^2R^3$, $R^2$ is heterocyclyl or heterocyclyl-$C_{1-6}$ alkyl wherein the heterocycle is an optionally substituted azetidinyl, pyrrolidinyl or piperidinyl and the heterocyclic nitrogen is optionally substituted by $C_{1-6}$ acyl or $C_{1-6}$ alkylsulfonyl, $R^3$ is $S(=O)_2R^6$, $R^6$ is $C_{1-6}$ alkyl and $R^{7b}$ is $C_{1-6}$ alkylsulfonyl or $C_{1-6}$ acyl.

In a tenth embodiment of the present invention there is provided a compound according to formula I wherein Y is $NR^2R^3$ and $A^1$ is meta-phenylene.

In a eleventh embodiment of the present invention there is provided a compound according to formula I wherein Y is $NR^2R^3$ and $A^2$ is optionally substituted 2-pyridinyl or 3-pyridinyl.

In a twelfth embodiment of the present invention there is provided a compound according to formula I wherein Y is $NR^2R^3$ and $A^1$ is pyridinylene.

In a thirteenth embodiment of the present invention there is provided a compound according to formula I select from the group consisting of I-1 to I-127 and I-128 in TABLE 1 of the specification.

In a fourteenth embodiment of the present invention there is provided a method for treating a disease caused by the Hepatitis C Virus (HCV) virus comprising administering to a patient in need thereof, a therapeutically effective quantity of a compound according to formula I wherein $A^1$, $A^2$, $R^1$, $R^2$, $R^3$, $R^4$, $R^5$, $R^6$, $R^7$, $R^{7a}$, $R^{7b}$, $R^{7c}$, $R^8$, $R^{8a}$, $R^{8b}$, $R^{8c}$, $R^9$, $R^{10}$, $R^{11}$, $R^1$, $X^2$, $X^3$, Y, m, n and p are as defined hereinabove.

In an fifteenth embodiment of the present invention there is provided a method for treating a disease caused by the Hepatitis C Virus (HCV) virus comprising co-administering to a patient in need thereof, a therapeutically effective quantity of a compound according to formula I wherein $A^1$, $A^2$, $R^1$, $R^2$, $R^3$, $R^4$, $R^5$, $R^6$, $R^7$, $R^{7a}$, $R^{7b}$, $R^{7c}$, $R^8$, $R^{8a}$, $R^{8b}$, $R^{8c}$, $R^9$, $R^{10}$, $R^{11}$, $X^1$, $X^2$, $X^3$, Y, m, n and p are as defined hereinabove along with at least one immune system modulator and/or at least one antiviral agent that inhibits replication of HCV.

In an sixteenth embodiment of the present invention there is provided a method for treating a disease caused by the Hepatitis C Virus (HCV) virus comprising co-administering to a patient in need thereof, a therapeutically effective quantity of a compound according to formula I wherein $A^1$, $A^2$, $R^1$, $R^2$, $R^3$, $R^4$, $R^5$, $R^6$, $R^7$, $R^{7a}$, $R^{7b}$, $R^{7c}$, $R^8$, $R^{8a}$, $R^{8b}$, $R^{8c}$, $R^9$, $R^{10}$, $R^{11}$, $X^1$, $X^2$, $X^3$, Y, m, n and p are as defined hereinabove along with at least one immune system modulator selected from the group consisting of an interferon, interleukin, tumor necrosis factor or colony stimulating factor.

In an seventeenth embodiment of the present invention there is provided a method for treating a disease caused by the Hepatitis C Virus (HCV) virus comprising co-administering to a patient in need thereof, a therapeutically effective quantity of a compound according to formula I wherein $A^1$, $A^2$, $R^1$, $R^2$, $R^3$, $R^4$, $R^5$, $R^6$, $R^7$, $R^{7a}$, $R^{7b}$, $R^{7c}$, $R^8$, $R^{8a}$, $R^{8b}$, $R^{8c}$, $R^9$, $R^{10}$, $R^{11}$, $X^1$, $X^2$, $X^3$, Y, m, n and p are as defined hereinabove along with at least one immune system modulator selected from the group consisting of an interferon, or a chemically derivatized interferon.

In an eighteenth embodiment of the present invention there is provided a method for treating a disease caused by the Hepatitis C Virus (HCV) virus comprising co-administering to a patient in need thereof, a therapeutically effective quantity of a compound according to formula I wherein $A^1$, $A^2$, $R^1$, $R^2$, $R^3$, $R^4$, $R^5$, $R^6$, $R^7$, $R^{7a}$, $R^{7b}$, $R^{7c}$, $R^8$, $R^{8a}$, $R^{8b}$, $R^{8c}$, $R^9$, $R^{10}$, $R^{11}$, $X^1$, $X^2$, $X^3$, Y, m, n and p are as defined hereinabove along with at least one antiviral agent selected from the group consisting of a HCV protease inhibitor, another HCV polymerase inhibitor, a HCV helicase inhibitor, a HCV primase inhibitor and a HCV fusion inhibitor.

In an nineteenth embodiment of the present invention there is provided a method for inhibiting replication of HCV virus in a cell comprising treating the cell comprising administering a therapeutically effective quantity of a compound according to formula I wherein $A^1$, $A^2$, $R^1$, $R^2$, $R^3$, $R^4$, $R^5$, $R^6$, $R^7$, $R^{7a}$, $R^{7b}$, $R^{7c}$, $R^8$, $R^{8a}$, $R^{8b}$, $R^{8c}$, $R^9$, $R^{10}$, $R^{11}$, $X^1$, $X^2$, $X^3$, Y, m, n and p are as defined.

In a twentieth embodiment of the present invention there is provided a pharmaceutical composition according to formula I wherein $A^1$, $A^2$, $R^1$, $R^2$, $R^3$, $R^4$, $R^5$, $R^6$, $R^7$, $R^{7a}$, $R^{7b}$, $R^{7c}$, $R^8$, $R^{8a}$, $R^{8b}$, $R^{8c}$, $R^9$, $R^{10}$, $R^{11}$, $X^1$, $X^2$, $X^3$, Y, m, n and p are as defined hereinabove admixed with at least one pharmaceutically acceptable carrier, diluent or excipient.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to; lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically named group. Thus, for example, "phenylalkyl" denotes the radical R'R''', wherein R' is a phenyl radical, and R'' is an alkylene radical as defined herein with the understanding that the attachment point of the phenylalkyl moiety will be on the alkylene radical. Examples of arylalkyl radicals include, but are not limited to, benzyl, phenylethyl, and 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe— or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "haloalkyl" as used herein denotes an unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The terms "amino", "alkylamino" and "dialkylamino" as used herein refer to —NH$_2$, —NHR and —NR$^2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to NH$_2$(alkylene)-, RHN(alkylene)-, and R$_2$N(alkylene)-respectively wherein R is alkyl, and both alkylene and alkyl are as defined herein. "$C_{1-10}$ alkylamino" as used herein refers to an aminoalkyl wherein alkyl is $C_{1-10}$. "$C_{1-10}$ alkyl-amino-$C_{2-6}$ alkyl" as used herein refers to a $C_{1-10}$ alkylamino(alkylene)$_{2-6}$ wherein alkyl is $C_{1-10}$ and the alkylene is $(CH_2)_{2-6}$. When the alkylene group contains three or more carbon atoms, the alkylene can be linear, e.g. —(CH$_2$)$_4$— or branched, e.g., —(CMe$_2$CH$_2$)—. The term "phenylamino" as used herein refers to —NHPh wherein Ph represents an optionally substituted phenyl group.

The terms "hydroxyalkyl" and "alkoxyalkyl" as used herein denotes alkyl radical as herein defined wherein one to three hydrogen atoms on different carbon atoms is/are replaced by hydroxyl or alkoxy groups respectively. A $C_{1-3}$ alkoxy-$C_{1-6}$ alkyl moiety refers to a $C_{1-6}$ alkyl substituent in which 1 to 3 hydrogen atoms are replaced by a $C_{1-3}$ alkoxy and the point of attachment of the alkoxy is the oxygen atom.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 1 to 6 carbon atoms. The $C_1$ acyl group is the formyl group wherein R=H and a $C_6$ acyl group refers to hexanoyl when the alkyl chain is unbranched. The term "arylcarbonyl" as used herein means a group of formula C(=O)R wherein R is an aryl group; the term "benzoyl" as used herein an "arylcarbonyl" group wherein R is phenyl.

The terms "alkylsulfonyl" and "arylsulfonyl" as used herein denotes a group of formula —S(=O)$_2$R wherein R is alkyl or aryl respectively and alkyl and aryl are as defined herein.

The term "halogen" or "halo" as used herein means fluorine, chlorine, bromine, or iodine.

The term "phenylene" as used herein refers to a benzene ring with two open valences. A phenylene moiety has three possible regioisomers, ortho-, -meta-orpara-phenylene. The term "pyridinylene" as used herein refers to a pyridine ring with two open valences. A pyridinylene moiety has six regioisomers. Para-pyridinylene refers to a 2,5-disubstituted pyridine and meta-phenylene refers to a 2,4-, 2,6- or 3,5-disubstituted pyridine.

The term "heteroaryl" or "heteroaromatic" as used herein means a monocyclic aromatic ring of 4 to 6 atoms incorporating one or more N, O, or S heteroatoms, the remaining ring atoms being carbon, with the understanding that the attachment point of the heteroaryl radical will be on a carbon atom. As well known to those skilled in the art, heteroaryl rings have less aromatic character than their all-carbon counter parts. Thus, for the purposes of the invention, a heteroaryl group need only have some degree of aromatic character. Examples of heteroaryl moieties include, but are not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. The term (hetero)aryl as used herein refers to an aromatic ring which is either an aryl or a heteroaryl ring as defined herein.

The term "heteroarylalkyl" (or "heteroaralkyl") means the radical of the formula R'R", wherein R' is an optionally substituted heteroaryl radical as defined herein, and R" is an alkylene radical as defined herein with the understanding that the attachment point of the heteroaryl radical will be on the alkylene radical. Examples of heteroarylalkyl radicals include, but are not limited to, 2-imidazolylmethyl, 3-pyrrolylethyl.

The term "heterocyclyl" or "heterocycle" as used herein denotes a monovalent saturated cyclic radical, consisting of one or more rings, preferably one to two rings, of three to eight atoms per ring, incorporating one or more ring heteroatoms (chosen from N, O or $S(=O)_{0-2}$) with the remaining ring atoms being carbon, with the understanding that the attachment point of the heteroaryl radical will be on a carbon atom. The heterocyclyl moiety can optionally be independently substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The terms "oxetane" (oxetanyl), "tetrahydrofuran" (tetrahydrofuranyl) and "tetrahydropyran" (tetrahydropyranyl") refer to a four, five and six-membered non-fused heterocyclic ring respectively, each containing one oxygen atom. "azetidine" ("azetidinyl") "pyrrole" ("pyrrolidinyl"), "piperidine" ("piperidinyl"), "azepine" ("azepinyl") The terms "furan" ("furyl"), "ipyrrole" ("pyrrolyl") and "thiophene" ("thienyl") refer to five membered heteroaryl rings with one oxygen, nitrogen and sulfur respectively. The term "pyridine" ("pyridinyl") refers to a six-membered heteroaromatic ring with one nitrogen atom. The terms "pyrimidine" (pyrimidinyl), "pyrazine" ("pyrazinyl") and "pyridazine" ("pyridazinyl") refer to a six-membered nonfused heteroaromatic ring with two nitrogen atoms disposed in a 1, 3, a 1, 4 and a 1, 2 relationship respectively. The respective radical names are in parentheses.

The term "heterocycloalkyl" (or "heterocyclylalkyl") denotes the radical of the formula R'R", wherein R' is a heterocyclic radical as defined herein, and R" is an alkylene radical as defined herein and the attachment point of the heterocycloalkyl radical will be on the alkylene radical. Examples of heterocycloalkyl radicals include, but are not limited to, 1-oxetanylmethyl, 2-piperidinylmethyl, and the like.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

The term "combination" as used herein in reference in administering a plurality of drugs in a therapeutic regimen by concurrent or sequential administration of the drugs at the same time or at different times.

The term "chemically-derivatized interferon" as used herein refers to an interferon molecule covalently linked to a polymer which alters the physical and/or pharmacokinetic properties of the interferon. A non-limiting list of such polymers include polyalkylene oxide homopolymers such as polyethylene glycol (PEG) or polypropylene glycol (PPG), polyoxyethylenated polyols, copolymers thereof and block copolymers thereof, provided that the water solubility of the block copolymers is maintained. One skilled in the art will be aware of numerous approaches to linking the polymer and interferon (for example, see A. Kozlowski and J. M. Harris *J. Control. Release* 2001 72(1-3):217-24). A non-limiting list of chemically derivatized IFNα contemplated in the present patent includes PEG interferon-α-2a (PEGASYS®) and PEG interferon-α-2b (PEGINTRON®).

Commonly used abbreviations include: acetyl (Ac), aqueous (aq.), atmospheres (Atm), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), $MeSO_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), satd. (saturated), tert-butyldimethylsilyl or t-BuMe2Si (TBDMS), triethylamine (TEA or $Et_3N$), triflate or $CF_3SO_2$— (Tf), trifluoroacetic acid (TFA), O-benzotriazol-1-yl-N,N,N',N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), $4$-Me-$C_6H_4SO_2$— or tosyl (Ts), N-urethane-N-carboxyanhydride (UNCA). Conventional nomenclature including the prefixes normal (n), iso (i-), secondary (sec-), tertiary (tert-) and neo- have their customary meaning when used with an alkyl moiety. (J. Rigaudy and D. P. Klesney, Nomenclature in Organic Chemistry, IUPAC 1979 Pergamon Press, Oxford.).

Compounds and Preparation

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, Volumes 1-21; R. C. LaRock, Comprehensive Organic Transformations, 2nd edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted as a Markush structure with generalized substituents; however, one skilled in the art will immediately appreciate that the nature of the R groups as defined in the claims can varied as defined in the appended claims to afford the various compounds contemplated in this invention. Moreover, the reaction conditions are exemplary and alternative conditions can be identified without undue experimentation. The reaction sequences in the following examples are not meant to limit the scope of the invention as set forth in the claims.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

TABLE I

| Cpd. No. | Structure | ms[1] | mp | IC$_{50}$[2] |
|---|---|---|---|---|
| I-1 | (structure) | 510 | 144.6-146.9 | 0.043 |
| I-2 | (structure) | 528 | | 0.1 |
| I-3 | (structure) | 544 | | 0.214 |

TABLE I-continued
| Cpd. No. | Structure | ms[1] | mp | IC$_{50}$[2] |
|---|---|---|---|---|
| I-4 | 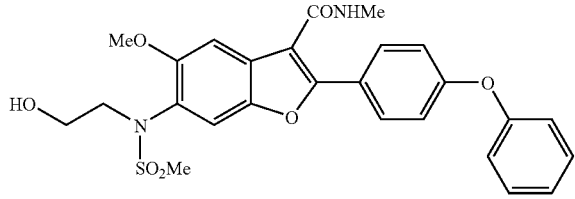 | 511 | | 0.062 |
| I-5 | 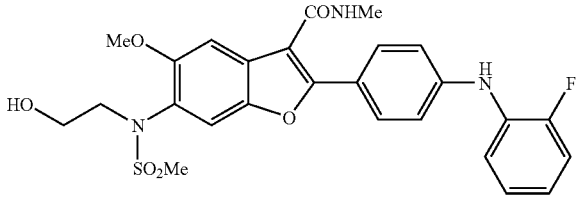 | 528 | | 0.034 |
| I-6 | 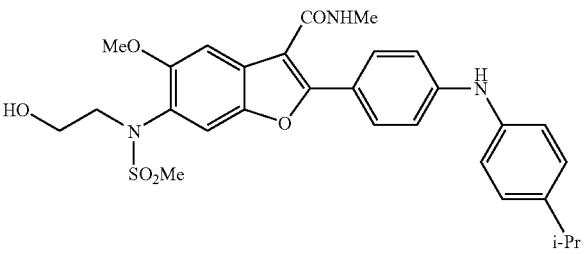 | 552 | 223.9-234.5 | 0.544 |
| I-7 | 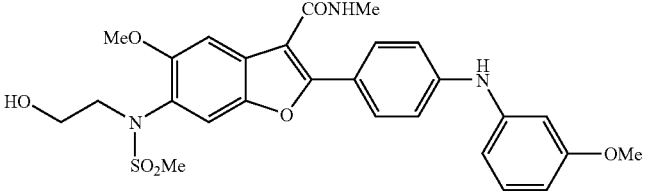 | 540 | | 0.136 |
| I-8 | 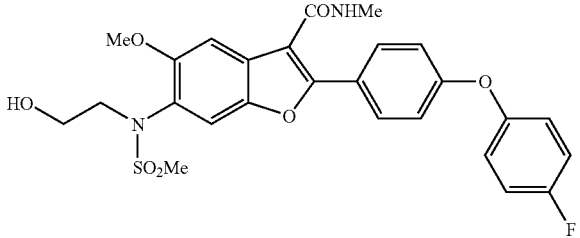 | 529 | | 0.057 |
| I-9 | 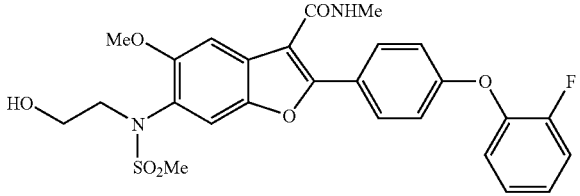 | 529 | | 0.085 |

TABLE I-continued

| Cpd. No. | Structure | ms[1] | mp | IC$_{50}$[2] |
|---|---|---|---|---|
| I-10 | 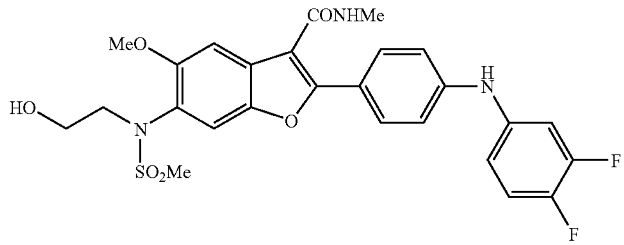 | 546 | | 0.065 |
| I-11 | 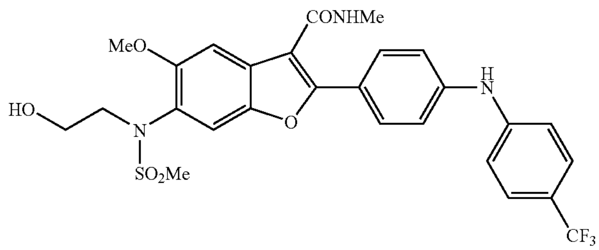 | 578 | | 1.955 |
| I-12 | 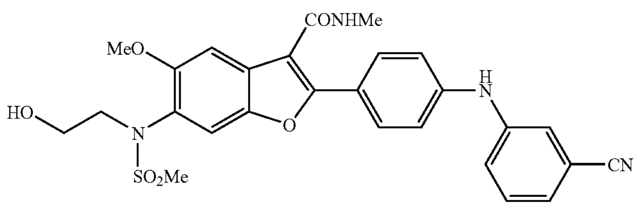 | 535 | | 0.298 |
| I-13 | 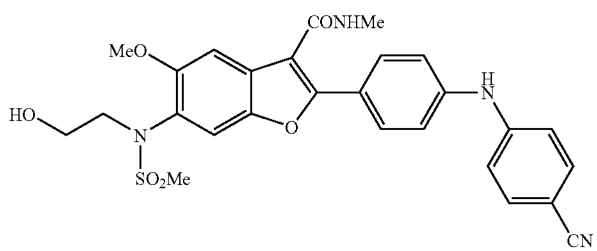 | 535 | | 1.845 |
| I-14 | 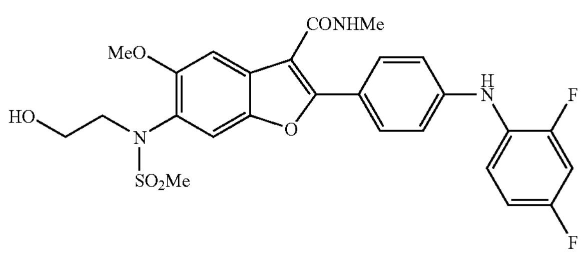 | 546 | | 0.024 |
| I-15 | 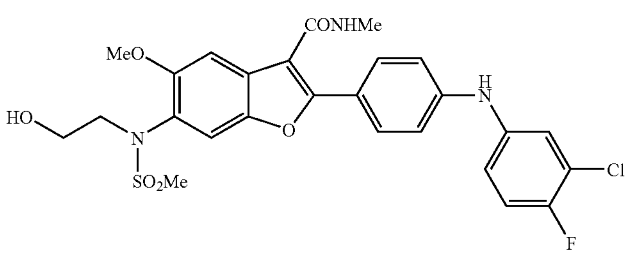 | 562 | | 0.082 |

TABLE I-continued

| Cpd. No. | Structure | ms[1] | mp | IC$_{50}$[2] |
|---|---|---|---|---|
| I-16 | 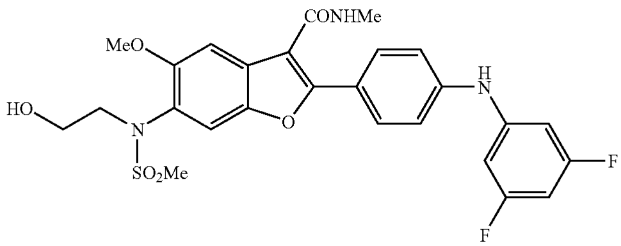 | 546 | | 0.172 |
| I-17 | 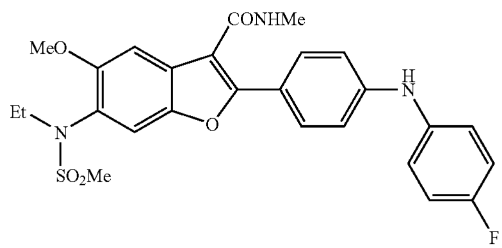 | 512 | | 0.081 |
| I-18 | 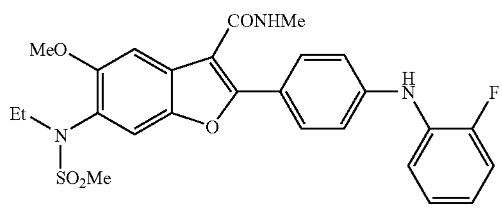 | 512 | | 0.005 |
| I-19 | 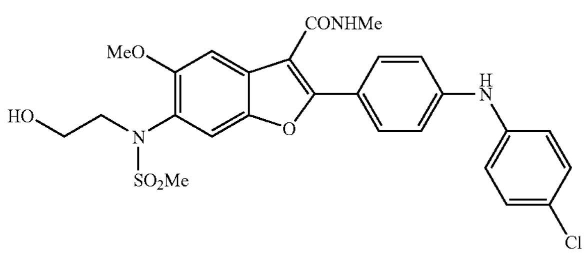 | 545 | | 0.037 |
| I-20 | 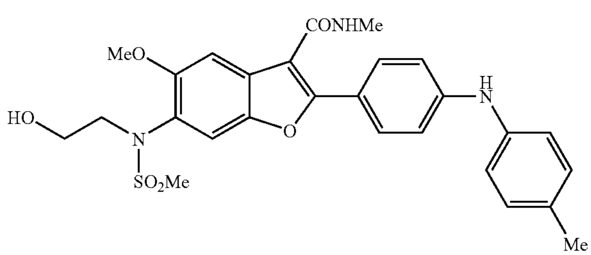 | 524 | | 0.092 |
| I-21 | 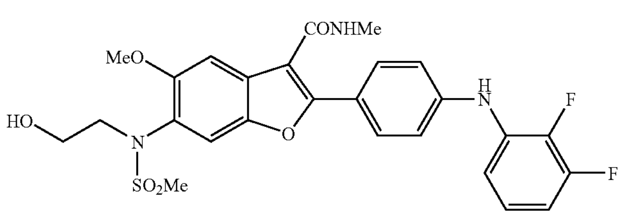 | 546 | | 0.059 |

TABLE I-continued

| Cpd. No. | Structure | ms[1] | mp | IC$_{50}$[2] |
|---|---|---|---|---|
| I-22 | 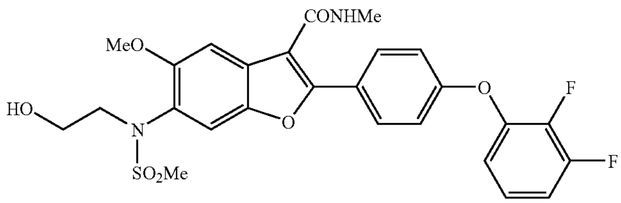 | 547 | | 0.055 |
| I-23 | 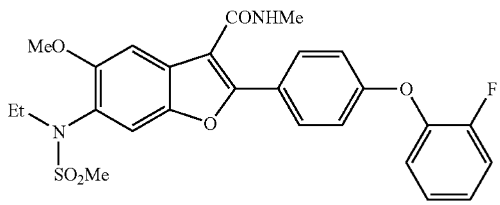 | 513 | | 0.052 |
| I-24 | 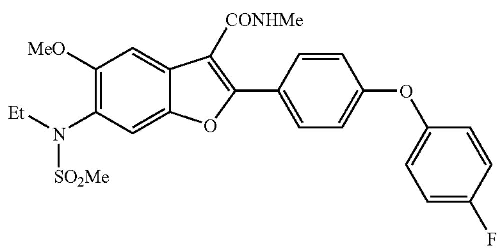 | 513 | | 0.13 |
| I-25 | 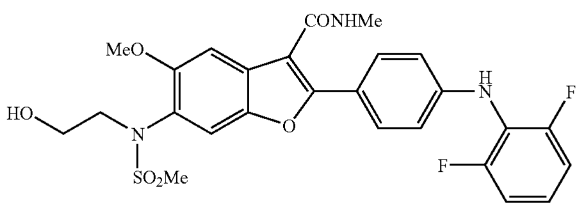 | 546 | | 0.123 |
| I-26 | 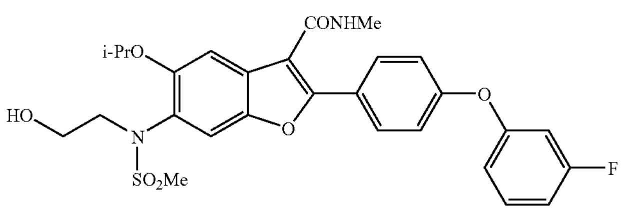 | 579 M + 23 | | 0.082 |
| I-27 | 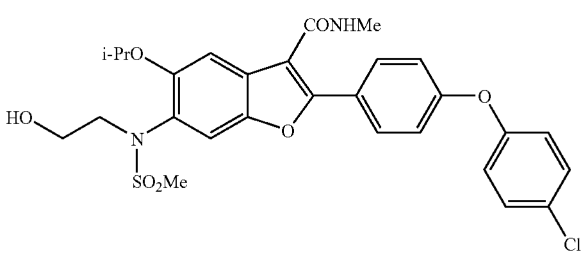 | 595 M + 23 | | 0.07 |
| I-28 | 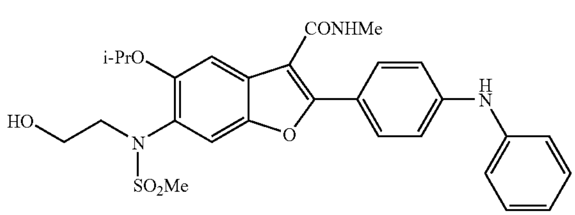 | 538 | | 0.042 |

TABLE I-continued

| Cpd. No. | Structure | ms[1] | mp | IC$_{50}$[2] |
| --- | --- | --- | --- | --- |
| I-29 | 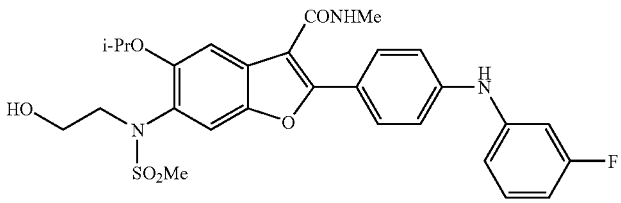 | 578 M + 23 | | 0.094 |
| I-30 | 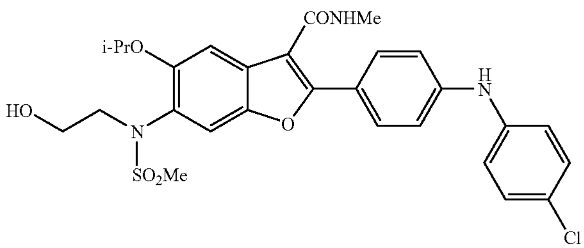 | 594 M + 23 | | 0.815 |
| I-31 | 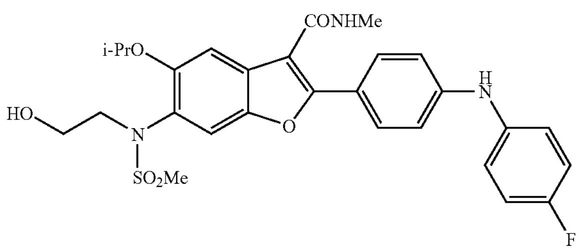 | 556 | | 0.092 |
| I-32 | 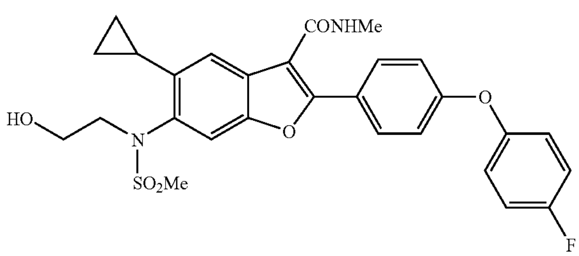 | 539 | 110.0-115.0 | 0.06 |
| I-33 | 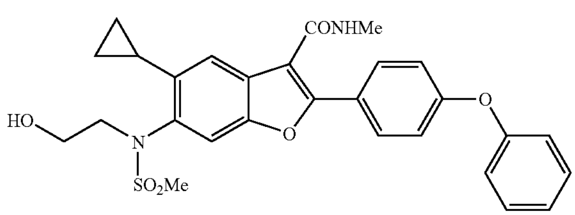 | 521 | 110.0-115.0 | 0.021 |
| I-34 | 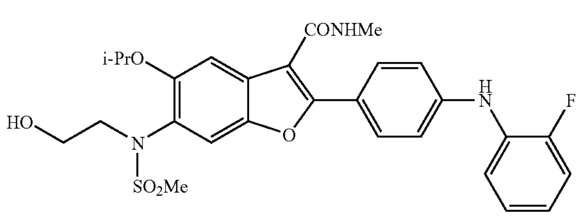 | 556 | | 0.064 |

TABLE I-continued

| Cpd. No. | Structure | ms[1] | mp | IC$_{50}$[2] |
|---|---|---|---|---|
| I-35 | 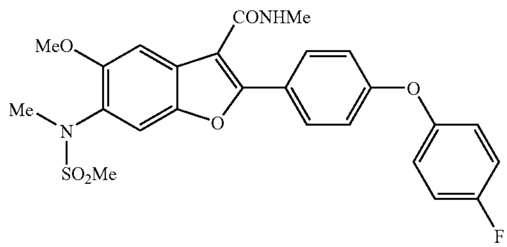 | 499 | | 0.051 |
| I-36 | 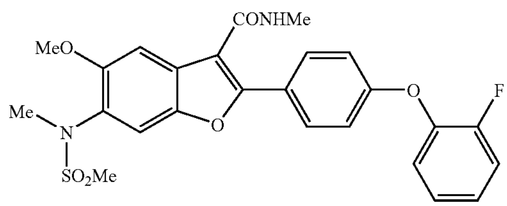 | 499 | | 0.048 |
| I-37 | 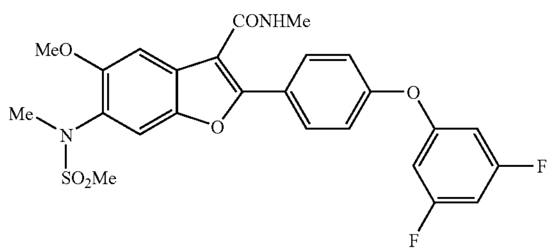 | 569 M + 23 | | 0.115 |
| I-38 | 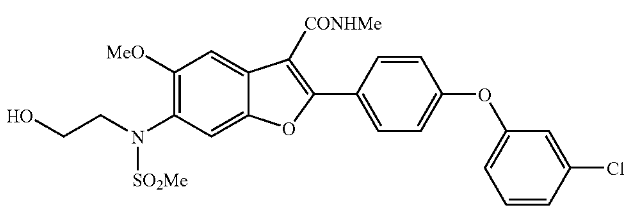 | 545 | | 0.05 |
| I-39 | 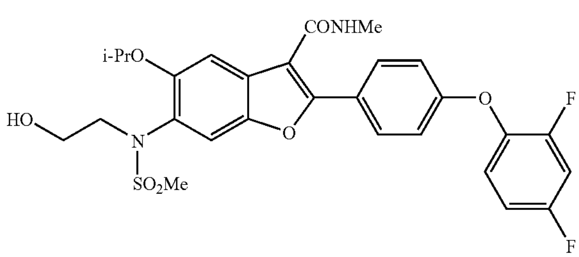 | 575 | | 0.195 |
| I-40 | 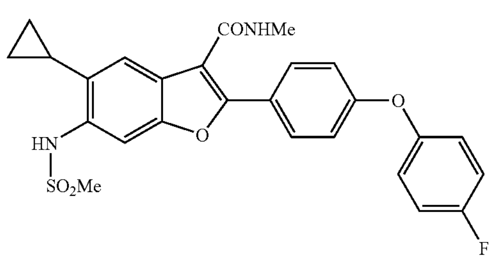 | | 169.0-170.0 | 0.098 |

TABLE I-continued

| Cpd. No. | Structure | ms[1] | mp | IC$_{50}$[2] |
|---|---|---|---|---|
| I-41 | 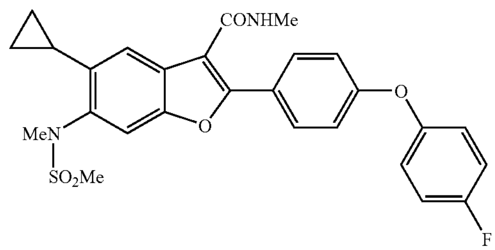 | 509 | 198.0-199.0 | 0.044 |
| I-42 | 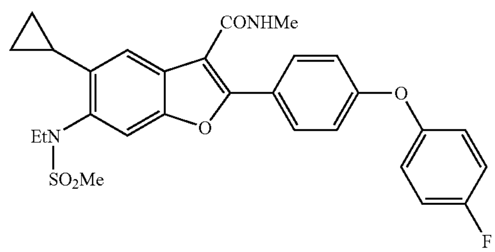 | 523 | | 0.143 |
| I-43 | 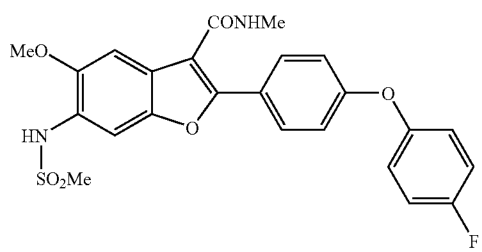 | 485 | | 0.238 |
| I-44 | 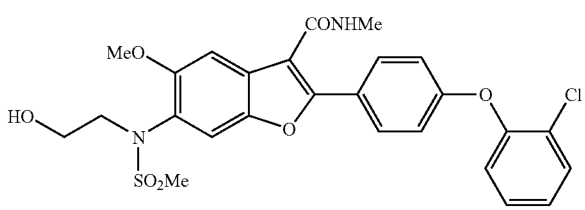 | 567 M + 23 | | 0.082 |
| I-45 | 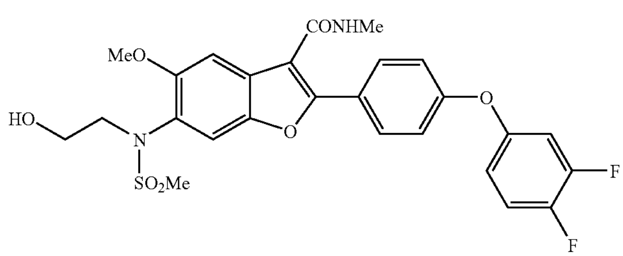 | 569 M + 23 | | 0.048 |
| I-46 | 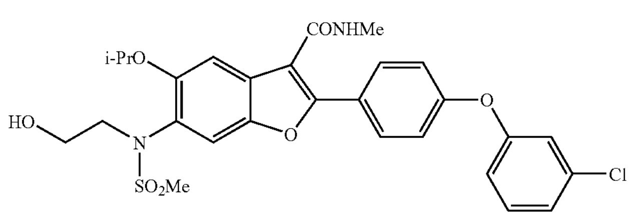 | 573 | | 0.051 |

TABLE I-continued

| Cpd. No. | Structure | ms[1] | mp | IC$_{50}$[2] |
|---|---|---|---|---|
| I-47 | MeO-, CONHMe, HO-ethyl-N(SO$_2$Me)-, benzofuran, -C$_6$H$_4$-O-C$_6$H$_4$-CN (3-CN) | 558 M + 23 | | 0.338 |
| I-48 | MeO-, CONHMe, HO-ethyl-N(SO$_2$Me)-, benzofuran, -C$_6$H$_4$-O-C$_6$H$_4$-CN (4-CN) | 558 M + 23 | | 1.07 |
| I-49 | i-PrO-, CONHMe, HO-ethyl-N(SO$_2$Me)-, benzofuran, -C$_6$H$_4$-O-C$_6$H$_4$-Cl (2-Cl) | 573 | | 0.143 |
| I-50 | i-PrO-, CONHMe, HO-ethyl-N(SO$_2$Me)-, benzofuran, -C$_6$H$_4$-O-C$_6$H$_3$-3,4-F$_2$ | 575 | | 0.261 |
| I-51 | Et-, CONHMe, HO-ethyl-N(SO$_2$Me)-, benzofuran, -C$_6$H$_4$-O-C$_6$H$_4$-F (4-F) | 527 | | 0.088 |
| I-52 | Et-, CONHMe, Me-N(SO$_2$Me)-, benzofuran, -C$_6$H$_4$-O-C$_6$H$_4$-F (4-F) | 497 | | 0.128 |

TABLE I-continued

| Cpd. No. | Structure | ms[1] | mp | IC$_{50}$[2] |
|---|---|---|---|---|
| I-53 | 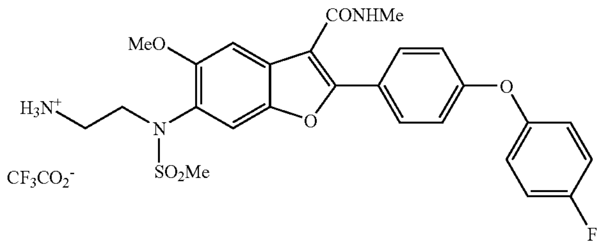 | 528 | | 0.25 |
| I-54 | 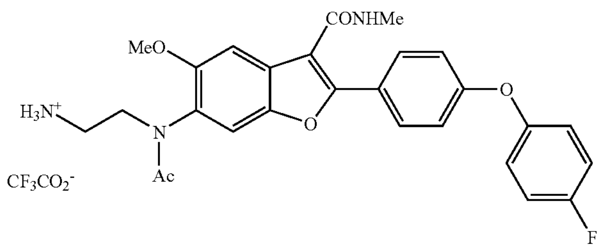 | 492 | | 1.235 |
| I-55 | 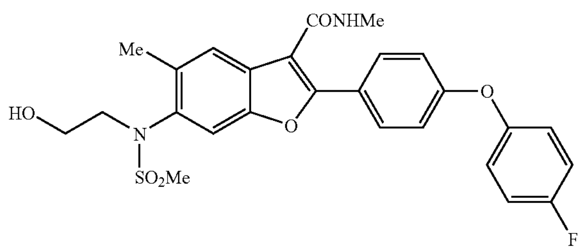 | 513 | | 0.044 |
| I-56 | 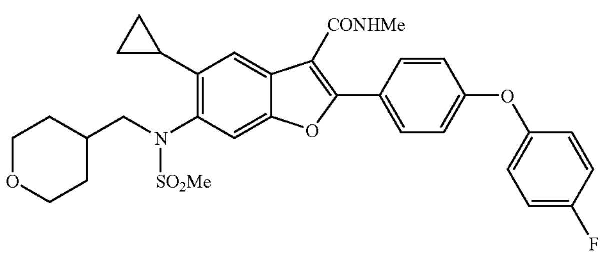 | 593 | | 0.157 |
| I-57 | 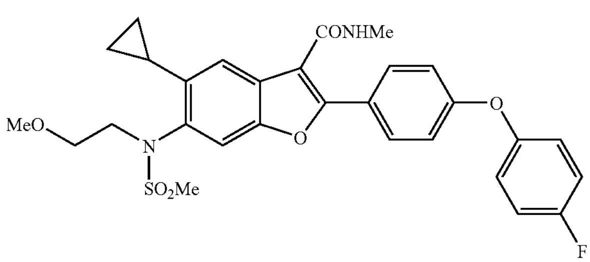 | 553 | | 0.11 |
| I-58 | 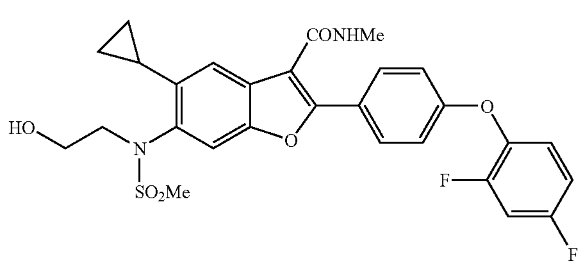 | 557 | | 0.085 |

TABLE I-continued

| Cpd. No. | Structure | ms[1] | mp | IC$_{50}$[2] |
|---|---|---|---|---|
| I-59 | 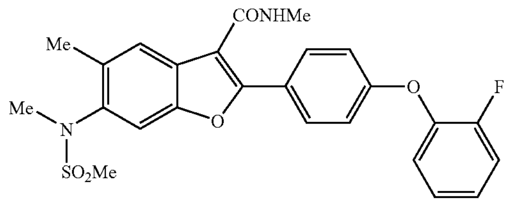 | 483 | | 0.093 |
| I-60 | 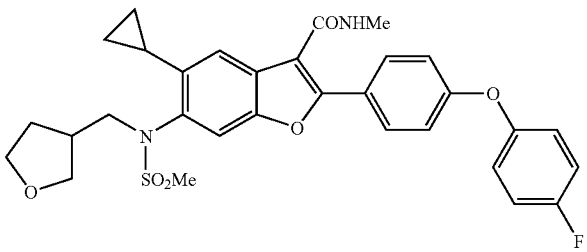 | 579 | | 0.115 |
| I-61 | 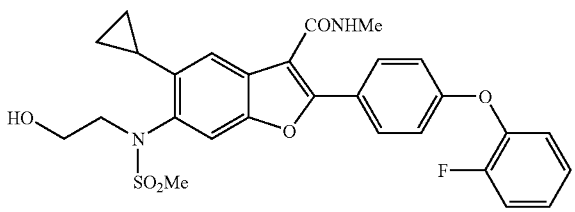 | 539 | | 0.035 |
| I-62 | 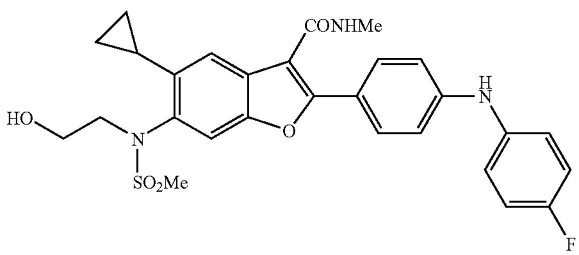 | 538 | | 0.013 |
| I-63 | 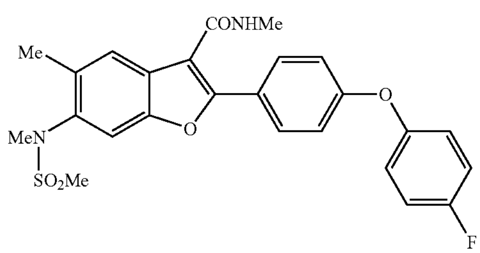 | 483 | 209.0-211.0 | 0.029 |
| I-64 | 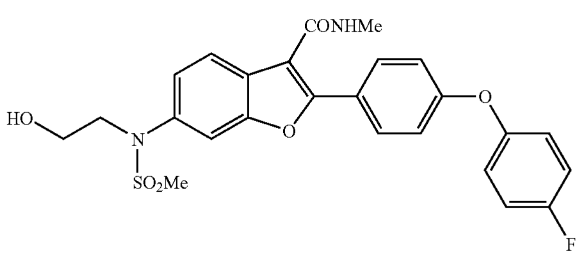 | 499 | 214.6-215.7 | 0.415 |

TABLE I-continued

| Cpd. No. | Structure | ms[1] | mp | IC$_{50}$[2] |
|---|---|---|---|---|
| I-65 | 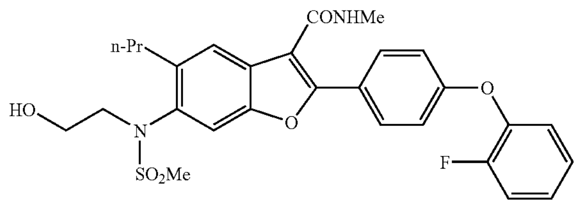 | 563 M + 23553 | | 0.021 |
| I-66 | 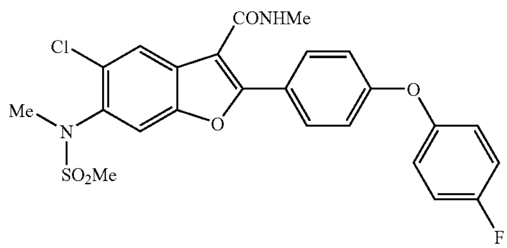 | 503 | | 0.029 |
| I-67 | | 595 | | 0.008 |
| I-67 | | 595 | | 0.008 |
| I-68 | 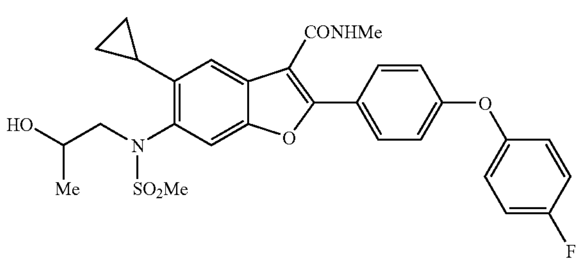 | 553 | | 0.026 |
| I-69 | 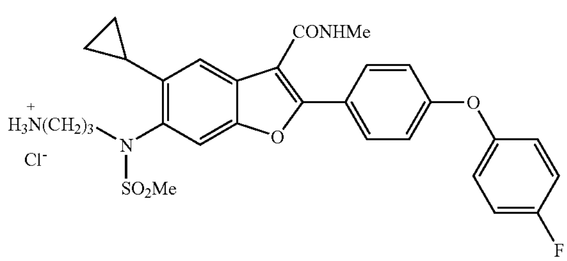 | 552 | | 0.018 |

TABLE I-continued

| Cpd. No. | Structure | ms[1] | mp | IC$_{50}$[2] |
|---|---|---|---|---|
| I-70 | 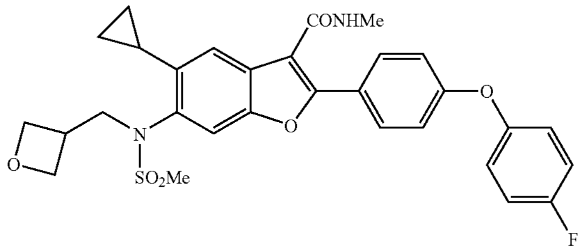 | 565 | | 0.013 |
| I-71 | 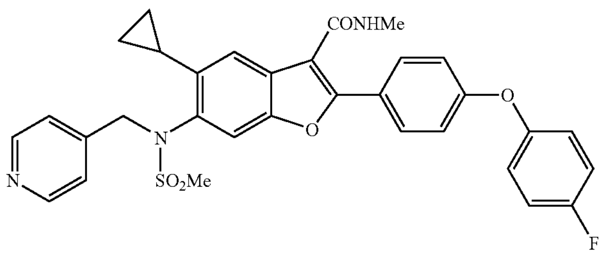 | 586 | | 0.009 |
| I-72 | 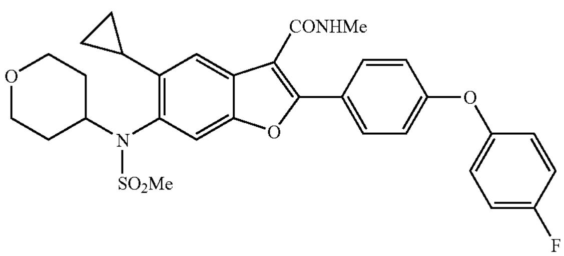 | 579 | | 0.591 |
| I-73 | 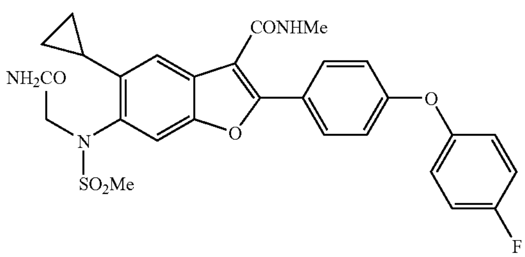 | 574 M + 223 | | 0.056 |
| I-74 | 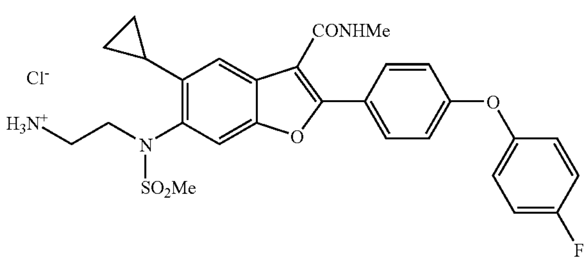 | 538 | 223.0-224.0 | 0.083 |
| I-75 | 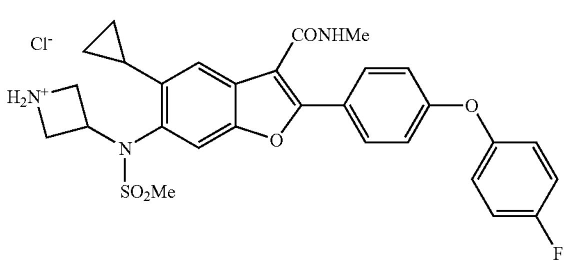 | 550 | | 0.3 |

TABLE I-continued

| Cpd. No. | Structure | ms[1] | mp | IC$_{50}$[2] |
|---|---|---|---|---|
| I-76 | 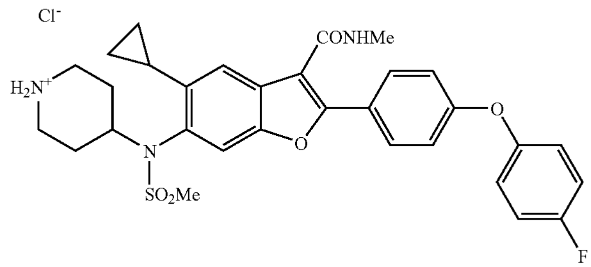 | 578 | | 0.376 |
| I-77 | 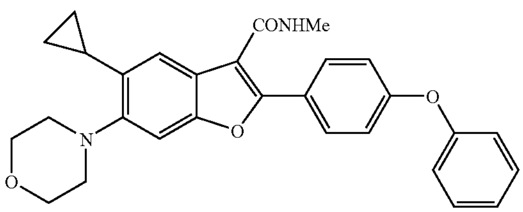 | 469 | 223.4-223.9 | 0.672 |
| I-78 | 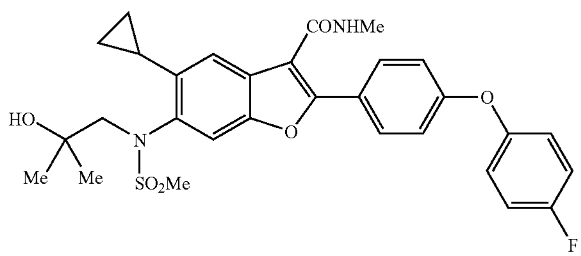 | 589 M + 23 | | 0.055 |
| I-79 | 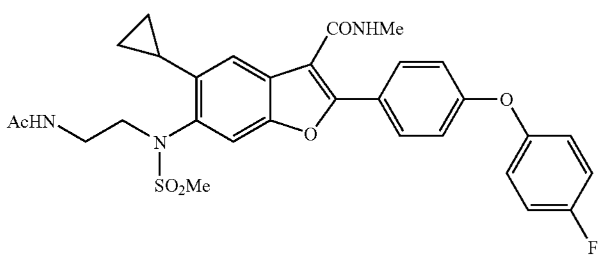 | 580 | | 0.068 |
| I-80 | 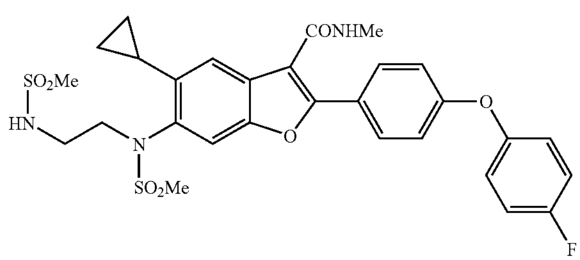 | 616 | | 0.179 |
| I-81 | 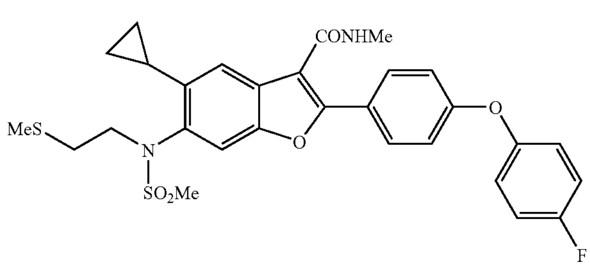 | 569 | | 0.016 |

TABLE I-continued

| Cpd. No. | Structure | ms[1] | mp | IC$_{50}$[2] |
|---|---|---|---|---|
| I-82 | 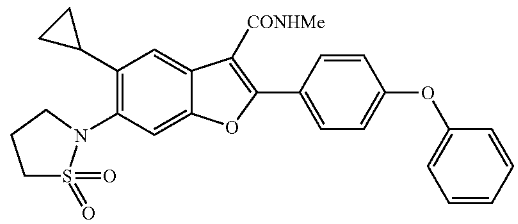 | 503 | 174.0-176.0 | 0.066 |
| I-83 | 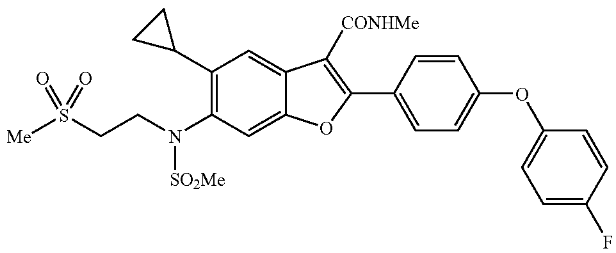 | 601 | 158.0-160.0 | 0.029 |
| I-84 | 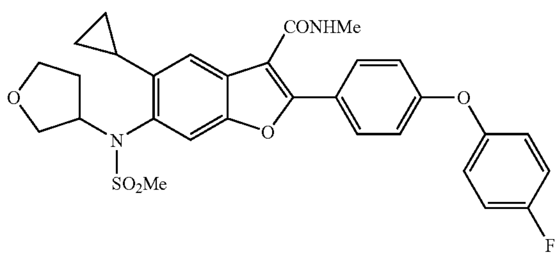 | 565 | | 0.155 |
| I-85 | 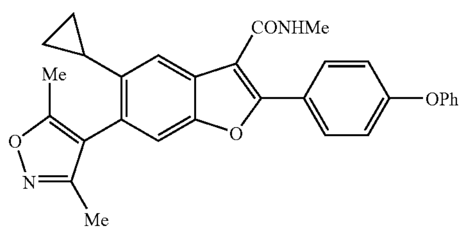 | 479 | | 0.344 |
| I-86 | 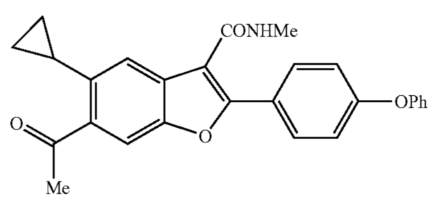 | 426 | | 0.362 |
| I-87 | 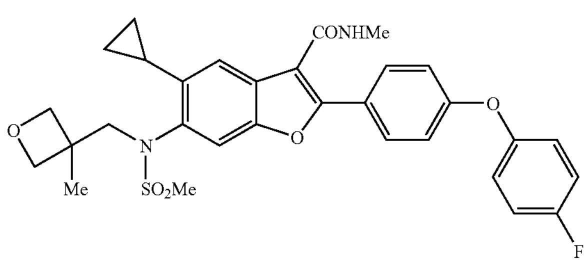 | 579 | | 0.134 |

TABLE I-continued

| Cpd. No. | Structure | ms[1] | mp | IC$_{50}$[2] |
|---|---|---|---|---|
| I-88 | 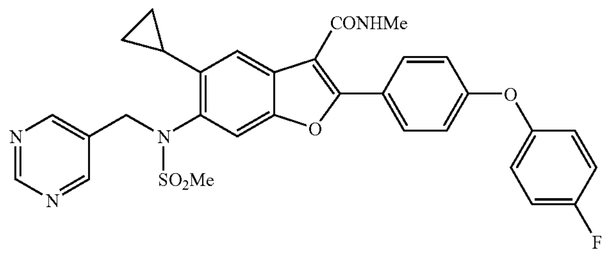 | 587 | | 0.026 |
| I-89 | 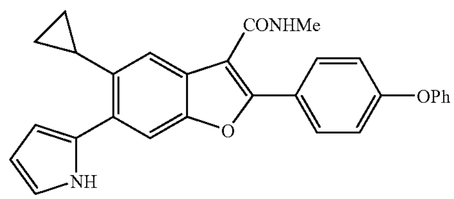 | 449 | | 0.722 |
| I-90 | 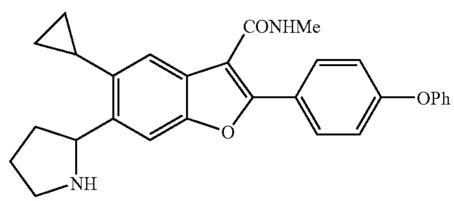 | 453 | | 0.254 |
| I-91 | 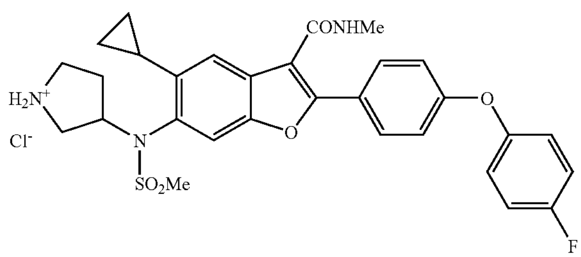 | 564 | | 0.024 |
| I-92 | 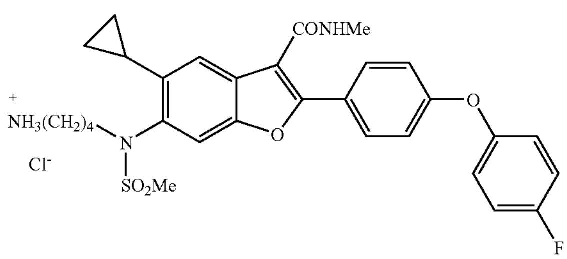 | 566 | | 0.056 |
| I-93 | 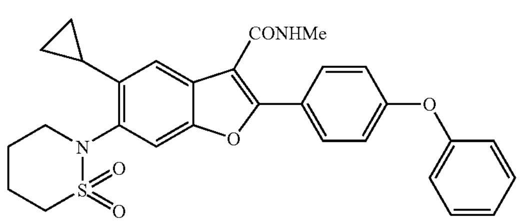 | 517 | 197.0-199.0 | 0.071 |

TABLE I-continued

| Cpd. No. | Structure | ms[1] | mp | IC$_{50}$[2] |
|---|---|---|---|---|
| I-94 | 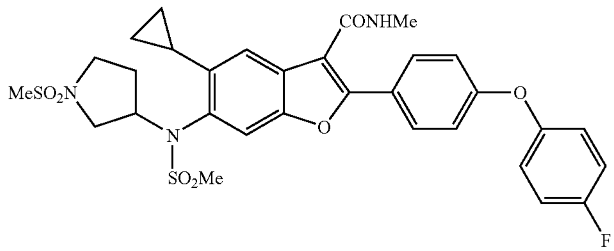 | 542 | | 0.028 |
| I-95 | 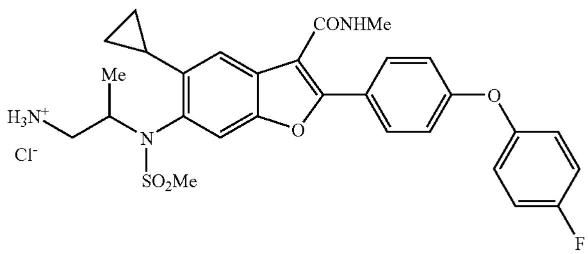 | 552 | | 0.06 |
| I-96 | 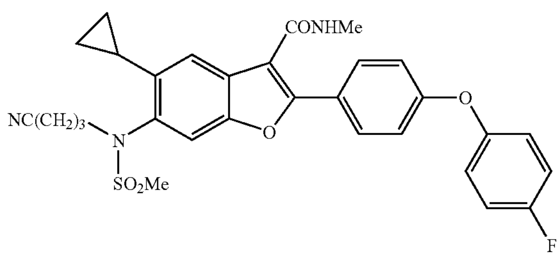 | 562 | | 0.007 |
| I-97 | 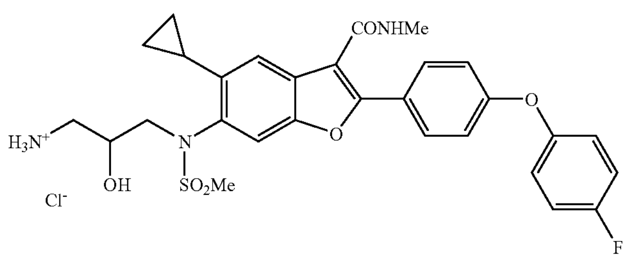 | 568 | | 0.048 |
| I-98 | 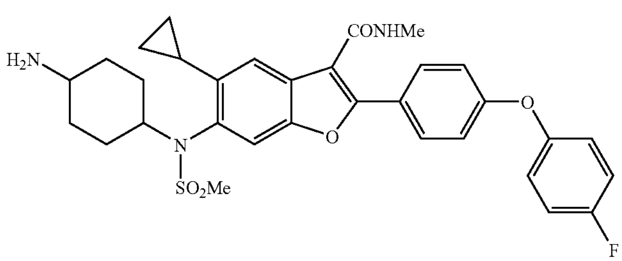 | 592 | | 0.044 |
| I-99 | 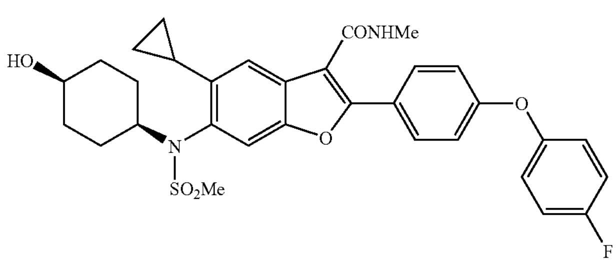 | 593 | | 0.023 |

TABLE I-continued

| Cpd. No. | Structure | ms[1] | mp | IC$_{50}$[2] |
|---|---|---|---|---|
| I-100 | 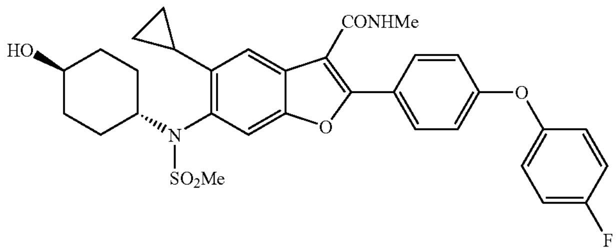 | 593 | | 0.025 |
| I-101 | 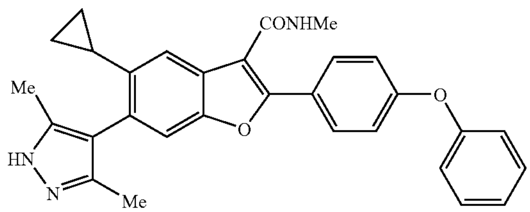 | 478 | | 0.318 |
| I-102 | 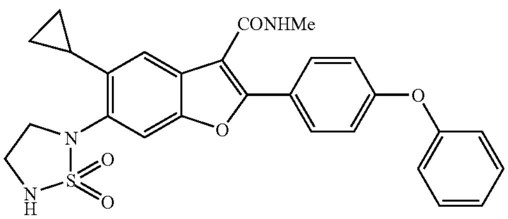 | 504 | 183.4-184.5 | 0.02 |
| I-103 | 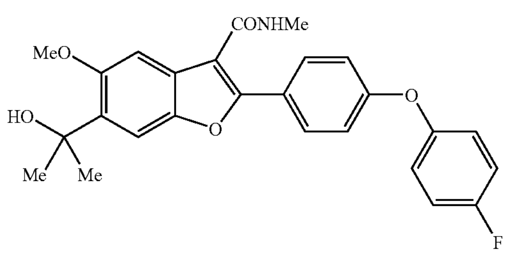 | 450 | | 0.037 |
| I-104 | 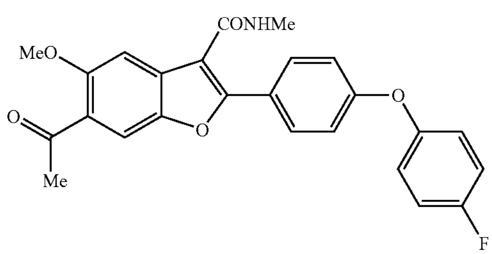 | 434 | 207.0-209.0 | 0.139 |
| I-105 | 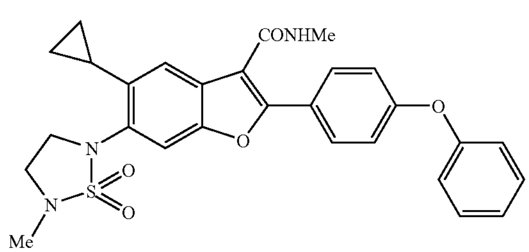 | 518 | 105.0-107.0 | 0.041 |

TABLE I-continued

| Cpd. No. | Structure | ms[1] | mp | IC$_{50}$[2] |
|---|---|---|---|---|
| I-106 | 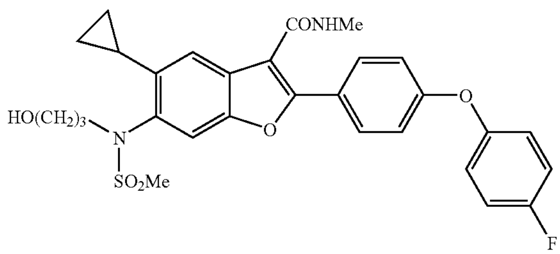 | 553 | | 0.018 |
| I-107 | 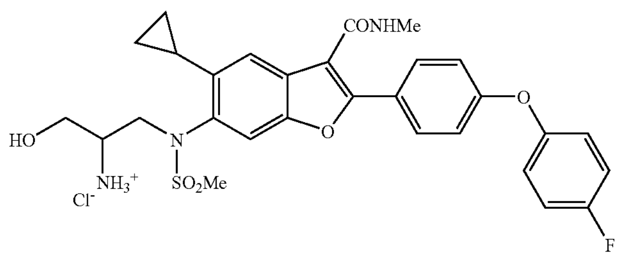 | 568 | 178.0-180.0 | 0.019 |
| I-108 | 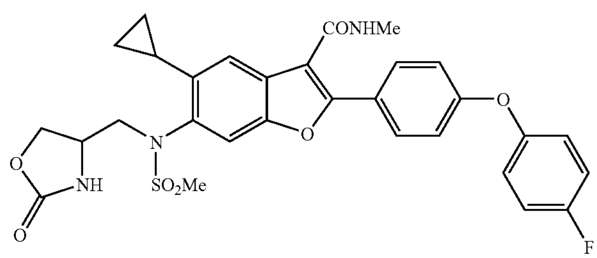 | 594 | | 0.026 |
| I-109 | 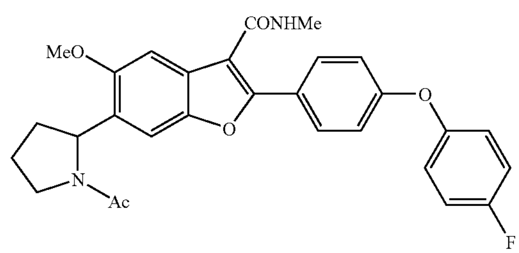 | 503 | | 0.044 |
| I-110 | 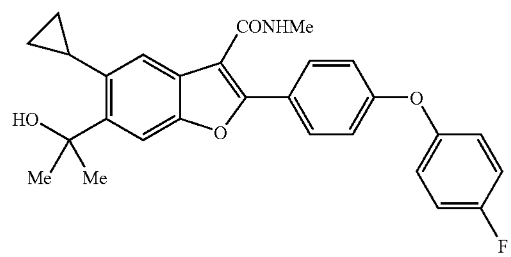 | 460 | | 0.039 |
| I-111 | 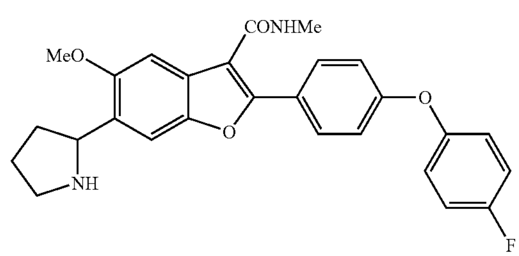 | 461 | | 0.933 |

TABLE I-continued

| Cpd. No. | Structure | ms[1] | mp | IC$_{50}$[2] |
|---|---|---|---|---|
| I-112 | 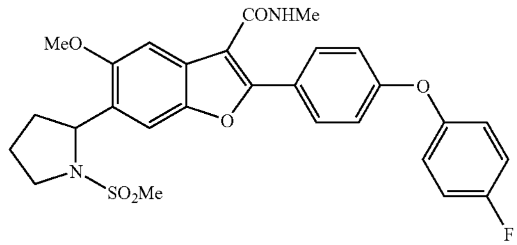 | 539* | | 0.349 |
| I-113 | 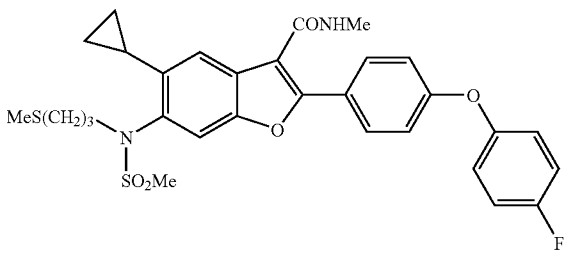 | 583 | | 0.018 |
| I-114 | 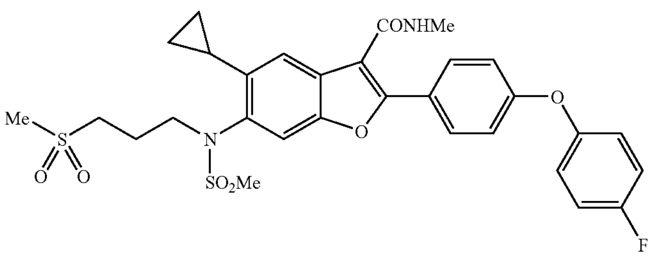 | 615 | | 0.021 |
| I-115 | 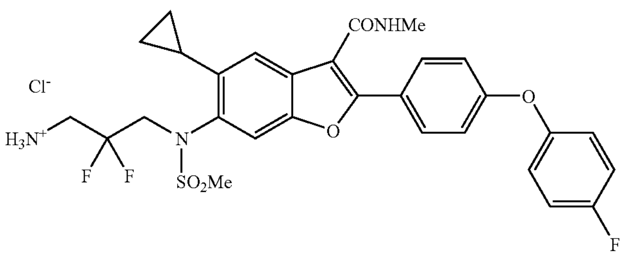 | 588 | | 0.029 |
| I-116 | 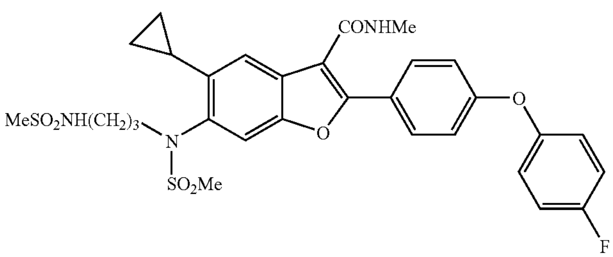 | 630 | | |
| I-117 | 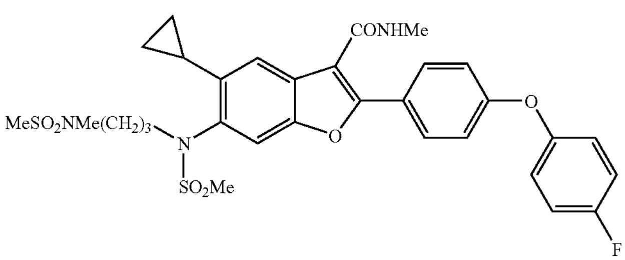 | 644 | | 0.011 |

TABLE I-continued

| Cpd. No. | Structure | ms[1] | mp | IC$_{50}$[2] |
|---|---|---|---|---|
| I-118 | 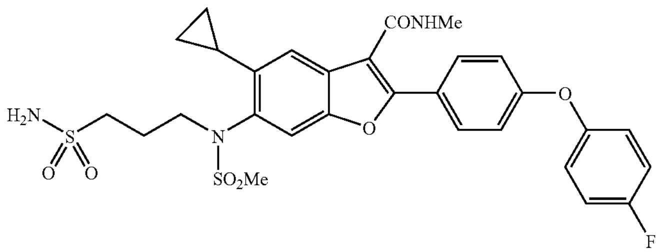 | 616 | | 0.007 |
| I-119 | 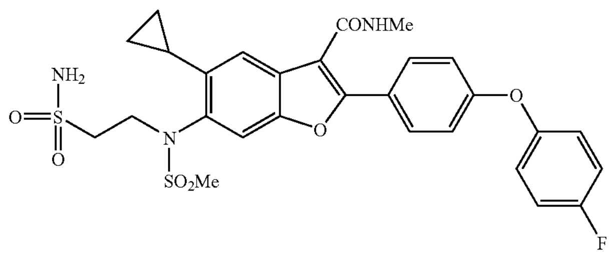 | 600 M − 1 | | 0.014 |
| I-120 | 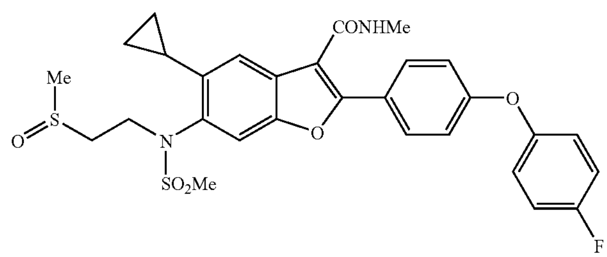 | 585 | | 0.019 |
| I-121 | 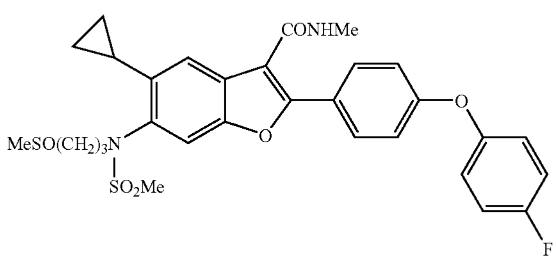 | 599 | | 0.005 |
| I-122 | 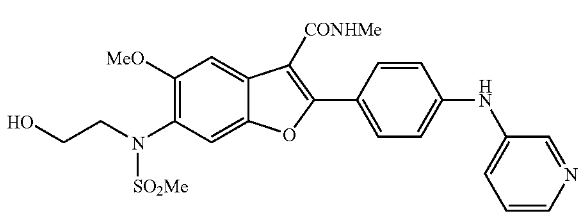 | 511 | | 2.05 |
| I-123 | 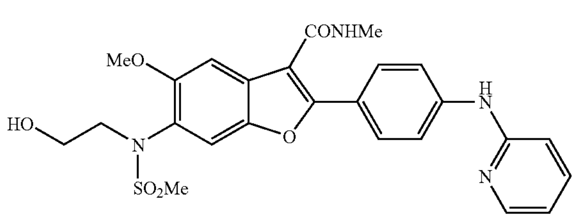 | 511 | 241.0-243.0 | 0.156 |

TABLE I-continued

| Cpd. No. | Structure | ms[1] | mp | IC$_{50}$[2] |
|---|---|---|---|---|
| I-124 | 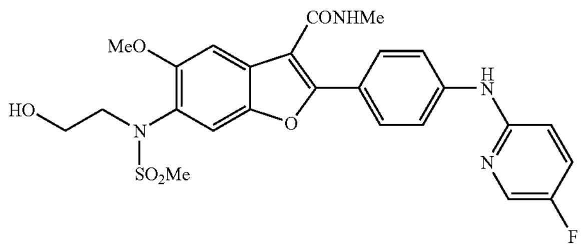 | 529 | | 0.195 |
| I-125 | 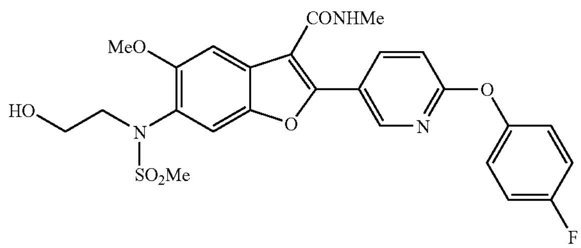 | 530 | | 0.49 |
| I-126 | 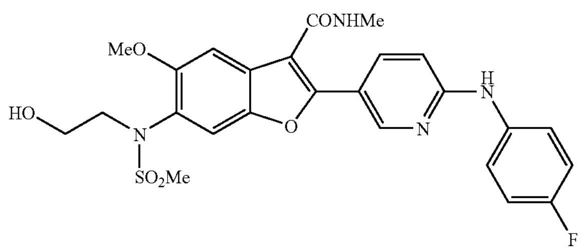 | 529 | | 0.468 |
| I-127 | 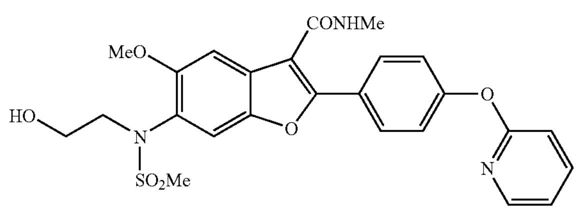 | 512 | | 0.611 |
| I-128 | 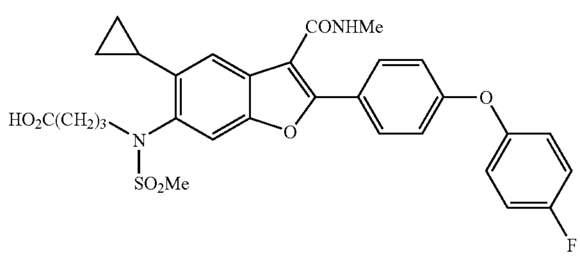 | 581 | | 0.004 |

1. Mass spectra data are (M + 1)+ peaks unless designated otherwise.
2. IC$_{50}$ (μM) data for NS5B polymerase assay as described in Example 25.

Compounds of the present invention with a 5-alkoxy substituent are prepared by condensation of a 5-alkoxy-salicylaldehyde and ethyl diazoacetate to afford an ethyl 5-alkoxy-benzofuran-3-carboxylate A-2a. (M. E. Dudley et al., *Synthesis* 2006 1711-14) The sequence depicted in SCHEME A exemplifies a compound wherein the 5-alkoxy moiety is a methoxy substituent; however, one skilled in the art will appreciate that other alkoxy ethers can be prepared from 5-hydroxy-salicylaldehyde. Introduction of a 4-bromo-phenyl substituent at C-2 is accomplished by a palladium-catalyzed Suzuki coupling. Deprotonation of C-2 with lithium diisopropylamide and quenching the resulting anion with trimethyl borate which is hydrolyzed to the requisite boronic acid during the aqueous workup. The 4-bromo-phenyl substituent is then conveniently introduced via a palladium-catalyzed coupling of A-2b and 4-iodo-bromobenzene.

SCHEME A

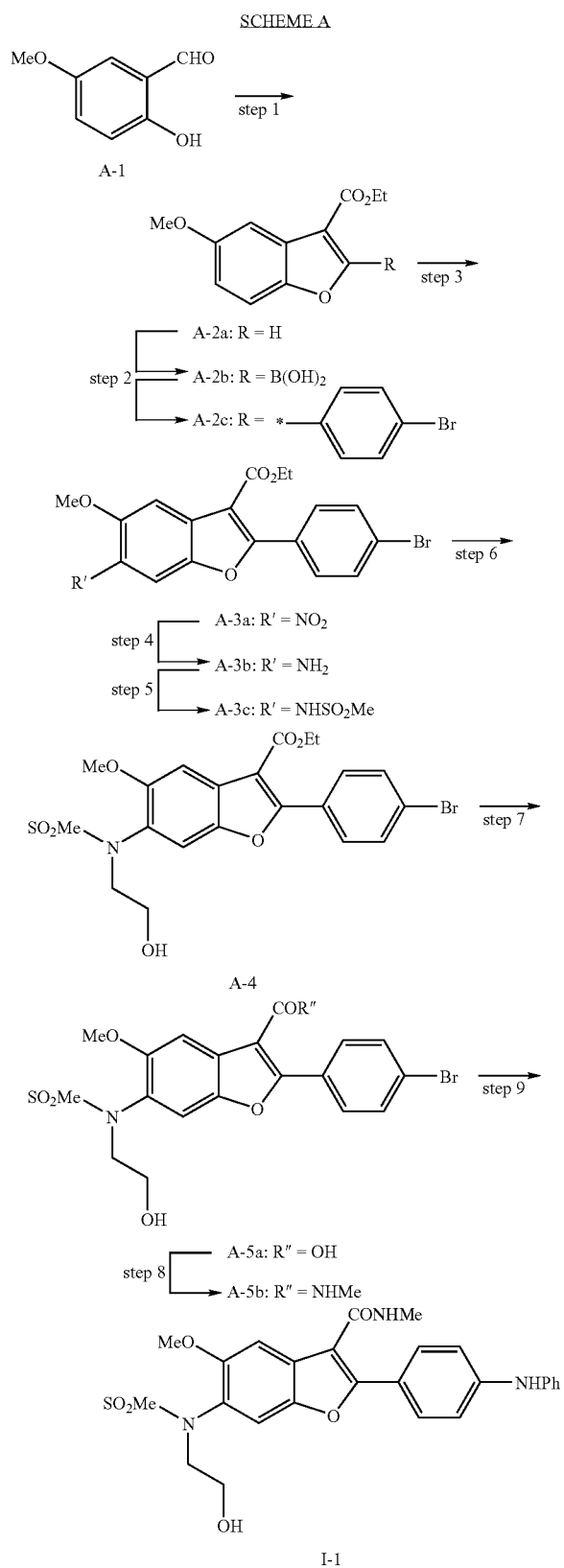

The Suzuki reaction is a palladium-catalyzed coupling of a boronic acid (R—B(OH)$_2$ wherein R is aryl or vinyl) with an aryl or vinyl halide or triflate (R'Y wherein R'=aryl or vinyl; Y=halide or —OSO$_2$CF$_3$) to afford a compound R—R'. Typical catalysts include Pd(PPh$_3$)$_3$, Pd(OAc)$_2$ and PdCl$_2$(dppf). With PdCl$_2$(dppf), primary alkyl boronic acid compounds can be coupled to aryl or vinyl halide or triflate without β-elimination. Highly active catalysts have been identified (see, e.g. J. P. Wolfe et al., *J. Am. Chem. Soc.* 1999 121(41): 9550-9561 and A. F. Littke et al., *J. Am. Chem. Soc.* 2000 122(17):4020-4028). The reaction can be carried out in a variety of organic solvents including toluene, THF, dioxane, DCE, DMF, DMSO and acetonitrile, aqueous solvents and under biphasic conditions. Reactions are typically run from about room temperature to about 150° C. Additives (e.g. CsF, KF, TlOH, NaOEt and KOH) frequently accelerate the coupling. There are a large number of parameters in the Suzuki reaction including the palladium source, ligand, additives and temperature and optimum conditions sometimes require optimization of the parameters for a given pair of reactants. A. F. Littke et al., supra, disclose conditions for Suzuki cross-coupling with arylboronic acids in high yield at RT utilizing Pd$_2$(dba)$_3$/P(tert-Bu)$_3$ and conditions for cross coupling of aryl- and vinyl triflates utilizing Pd(OAc)$_2$/P(C$_6$H$_{11}$)$_3$ at RT. J. P. Wolf et al., supra, disclose efficient condition for Suzuki cross-coupling utilizing Pd(OAc)$_2$%-(di-tert-butylphosphino)biphenyl or o-(dicyclohexylyphosphino)biphenyl. One skilled in the art can determine optimal conditions without undue experimentation.

Nitration of the benzofuran afforded a mixture of isomers from which the 6-nitro derivative A-3a could be isolated. Aromatic nitration is well known and can be conducted under a variety of conditions known in the art. Nitration can be carried out by exposing an aromatic compound to a mixture of concentrated nitric acid and sulfuric acid. Active substrates can be nitrated with HNO$_3$ alone or in H$_2$O, HOAc and acetic anhydride and active compounds may be oxidized by mixtures of HNO$_3$ and H$_2$SO$_4$. Other nitrating reagents include NaNO$_3$/TFA, N$_2$O$_4$, NO$_2^+$BF$_4^-$, NO$_2^+$PF$_6^-$ and NO$_2$+CF$_3$SO$_4^-$. (J. March, *Advanced Organic Chemistry*, John Wiley & Sons: New York, N.Y., 1992, pp. 522-23)

Reduction of the nitro group and sulfonation of A-3a was carried out under standard conditions. Reduction of a nitro compound is achieved with a reducing agent in an inert solvent, e.g. MeOH, EtOH, EtOAc, THF or mixtures thereof. The reduction may be carried out under known hydrogenation conditions in the presence of a metal catalyst, e.g. nickel catalysts such as Raney nickel, palladium catalysts such as Pd/C, platinum catalysts such as PtO$_2$, or ruthenium catalysts such as RuCl$_2$(Ph$_3$P)$_3$ under H$_2$ atmosphere or in the presence of hydrogen sources such as hydrazine or formic acid. If desired, the reaction is carried out under acidic conditions, e.g. in the presence of HCl or HOAc. The reduction may also be carried out in the presence of a suitable reducing agent, e.g. LiAlH$_4$, LiBH$_4$, Fe, Sn or Zn, in a reaction inert solvent, e.g. MeOH, EtOH, diglyme, benzene, toluene, xylene, o-dichlorobenzene, DCM, DCE, THF, dioxane, or mixtures thereof; or without solvent. If desired, when the reducing reagent is Fe, Sn or Zn, the reaction is carried out under acidic conditions in the presence of water. Sulfonylation of the A-3b with methanesulfonyl chloride in the presence of base under standard conditions afforded A-3c.

The N-arylsulfonamide A-3c was sufficiently acidic to undergo deprotonation and alkylation in the presence of K$_2$CO$_3$ and MeCN. The sulfonamide salt is treated with an alkylating agent, RZ$^1$, wherein Z$^1$ is a leaving group such as a halide, C$_{1-4}$ alkanesulfonyloxy, benzenesulfonyloxy or p-toluenesulfonyloxy. Varying the alkylating agent allows the introduction of a variety of substituents on the nitrogen atom and examples of other nitrogen substituents can be found in the examples which follow. One skilled in the art would appreciate the sequence of these reactions can be altered to afford additional flexibility. For example the aromatic amine can first be alkylated and the resulting secondary amine sulfonylated. The initial alkylation can be carried out by direct alkylation of the amine with an alkylating agent or by reductive amination of the amine. Alkylation of amines is typically carried out in aprotic solvents such as THF, DMF, DMSO, NMP and mixtures thereof at temperatures between −78° C. and 100° C. Typically used bases are potassium carbonate, sodium hydride, potassium hydride, lithium hexamethyldisilazide, sodium hexamethyldisilazide, potassium hexamethyldisilazide. Reductive amination is typically carried out by combining an amine and carbonyl compound in the presence of a complex metal hydride such as $NaBH_4$, $LiBH_4$, $NaBH_3CN$, $Zn(BH4)_2$, sodium triacetoxyborohydride or borane/pyridine conveniently at a pH of 1-7 optionally in the presence of a dehydrating agent such as molecular sieve or $Ti(IV)(O-i-Pr)_4$ to facilitate formation of the intermediate imine at ambient temperature. Reductive amination procedures have been reviewed: R. M. Hutchings and M. K. Hutchings, Reduction of C=N to CHNH by Metal Hydrides in Comprehensive Organic Synthesis col. 8, I. Fleming (Ed) Pergamon, Oxford 1991 pp. 47-54. Acylation or sulfonylation is readily accomplished by treating the N-alkylamine with an acylating agent of sulfonylating agent.

The term "acylating agent" as used herein refers to either an anhydride, acid halide or an activated derivative of a carboxylic acid. The term "anhydride" as used herein refers to compounds of the general structure RC(O)—O—C(O)R. The term "acid halide" as used herein refers to compounds of the general structure RC(O)X wherein X is a halogen. The term "activated derivative" of a compound as used herein refers to a transient reactive form of the original compound which renders the compound active in a desired chemical reaction, in which the original compound is only moderately reactive or non-reactive. Activation is achieved by formation of a derivative or a chemical grouping within the molecule with a higher free energy content than that of the original compound, which renders the activated form more susceptible to react with another reagent. In the context of the present invention activation of the carboxy group is of particular importance and corresponding activating agents or groupings which activate the carboxy group are described in more detail below. A variety of activating agents are well known, e.g., diimides (e.g., EDCI, DCC), EEDQ, BOP, DEAD-PPh₃, diethylcyanophosphate, diethylphosphorylazide, 2-chloro-1-methylpyridinium iodide, or ethyl chloroformate. The acylation are carried out in an inert solvent, e.g. acetone, DMF, MeCN, halogenated hydrocarbons, such as DCM, DCE, chloroform, and ethers, such as THF and dioxane. If desired, this reaction may be carried out in the presence of an additive such as HOBt or 1-hydroxyazabenzotriazole or in the presence of a base such as NMM.

Conversion of the ester A-4 to the corresponding amide A-5b is carried out under conventional conditions. Esters can be further converted to carboxylic acids under basic reaction conditions (for further reaction conditions see R. C. Larock, Comprehensive Organic Transformations—A Guide to Functional Group Preparations, 1989, VCH Publishers Inc., New York; pp. 981-985), preferentially using potassium or sodium hydroxide at RT or elevated temperatures in a solvent such as MeOH, dioxane, THF, DMF or DMA or mixtures thereof. In order to enhance the rate of conversion heating might be applied, whereby conventional heating or microwave assisted heating might be employed using a suitable microwave irradiation apparatus. The acid is then converted to an acid halide with a halogenating agent such as oxalyl chloride or thionyl chloride to afford an acyl chloride or another activated carboxylic acid derivative supra, which is condensed with an amine to form the corresponding amide.

Formation of the diaryl amine linkage in step 9 was carried out utilizing a palladium catalyzed coupling of A-5b and an optionally substituted aniline. Displacement of a suitable leaving group such as chlorine, bromine, iodine, mesylate (methanesulfonate) or triflate (trifluoro-methanesulfonate) substituent on aryl or heteroaryl ring by amines (e.g., Buchwald-Hartwig coupling) has become a well established procedure. (see, e.g., (a) J. P. Wolfe, S. Wagaw and S. L. Buchwald *J. Am. Chem. Soc.* 1996 118:7215-7216; (b) J. P. Wolfe and S. L. Buchwald *Tetrahedron Lett.* 1997 38:6359-6362; (c) J. P. Wolfe, S. Wagaw, J.-F. Marcoux and S. L. Buchwald, *Acc. Chem. Res.* 1998 31:805-818; (d) B. H. Yang and S. L. Buchwald *J. Organomet. Chem.* 1999 576:125-146; (e) J. F. Hartwig, *Angew. Chem. Int. Ed.* 1998 37:2046-2067; (f) A. Prim et al., *Tetrahedron* 2002 58:2041). The amination of an aryl halide or sulfonate is catalyzed by palladium catalyst such as tris-(dibenzylideneacetone) dipalladium(0) ($Pd_2(dba)_3$) or $Pd(OAc)_2$, a phosphine ligand like triphenylphosphine, rac-2,2'-bis(diphenylphosphino)-1,1'-binaphthalene (rac-BINAP), dicyclohexyl-(2',4',6'-tri-iso-propyl-biphenyl-2-yl)-phosphane (X-Phos), (R)-(−)-1-[(S)-2-(dicyclohexylphosphino)ferrocenyl]ethyldi-tert-butylphosphine (Josiphos; see Q. Shen, S. Shekhar, J. P. Stambuli and J. F. Hartwig, *Angew. Chem. Int. Ed.* 2005 44:1371-1375), $P(C_6H_{11})_3$, $P(ortho-Tol)_3$ or $P(tert-Bu)_3$. Basic additives such as $Cs_2CO_3$, $K_3PO_4$ or KO-tert-Bu in a solvent like toluene, EtOH, DME, dioxane or water or mixtures thereof, are commonly employed. C—N formation may be conducted at RT or at elevated temperatures which may be achieved conventionally or by microwave irradiation (see also Palladium(0) Complexes in Organic Chemistry, in *Organometallics in Synthesis* (Ed. M. Schlosser), Chapter 4, 2nd Edition, 2002, John Wiley & Sons, Ltd, Chichester, UK and D. Prim et al., *Tetrahedron* 2002 58:2041. One skilled in the art will appreciate that the sequence could be altered to couple a 4-halo-aniline to be benzofuran and subsequently utilize an optionally substituted aryl bromide, iodide, triflate or mesylate in step 9. These alternatives afford great flexibility constructing substituted diaryl amines.

Compounds of the present invention which contain a diaryl ether in place of the diaryl amine can be prepared by a similar sequence. Methodology to introduce a biaryl ether by palladium-catalyzed coupling of an aryl bromide and a phenol has been optimized. (C. H. Burgos et al., *Angew. Chem. Int. Ed. Eng.* 2006 45:4321-4326). Coupling A-5b and phenol thus affords I-4.

SCHEME B

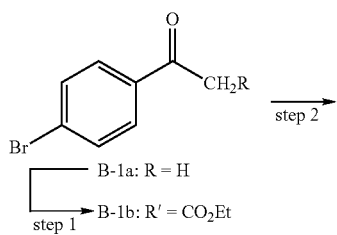

B-1a: R = H
B-1b: R' = CO₂Et
step 1
step 2

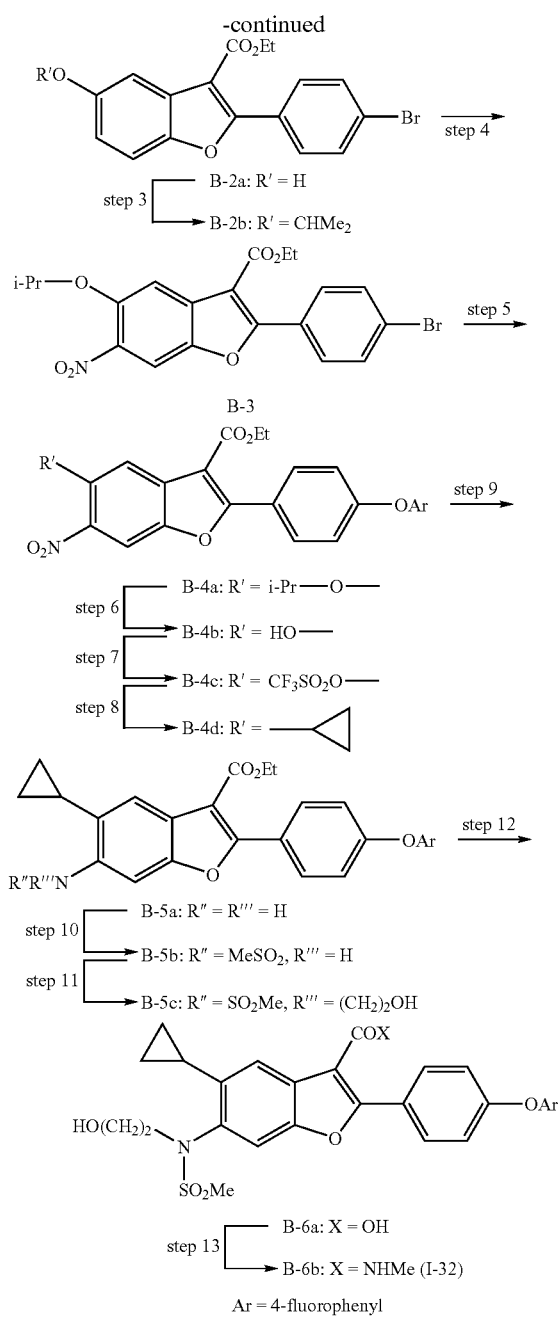

Ar = 4-fluorophenyl

Alkyl benzofurans can be prepared analogously from the corresponding 5-alkyl salicylaldehydes in similar fashion. 2-Alkyl-benzofurans also can be prepared by $H_2O_2$ oxidation of flavylium salts which, in turn, are prepared by condensation of a 5-alkyl-salicyladehyde and a 2-methoxyacetophenone substituted on the aryl ring with a halo or a suitably protected amine in the 4-position of the phenyl ring. (E. Ritchie and W. C. Turner, *Aust. J. Chem.* 1969 22 1329-30 and R. S. McCredie et al. *Aust. J. Chem.* 1969, 22, 1011). Alternatively 5-alkyl- and 5-cyclopropyl-benzylfuran were prepared as depicted in SCHEME B based on the procedure described by C. Burns, et al. in WO2004/041201 published May 21, 2004. Lewis-acid catalyzed condensation of paraquinone and ethyl 3-(4-bromo-phenyl)-3-oxo-propionate affords the benzofuran B-2a in which the C-2 aryl substituent has been introduced. In the example which follows the 5-hydroxy group is protected as an alkyl ether and a 6-amino group is introduced by nitration (step 4). After palladium-catalyzed coupling of a phenol or aniline to the diaryl ether or amine the alkyl-aryl ether are cleaved to afford the phenol (step 6) which can be converted to the triflate ester and subjected to Suzuki-coupling to introduce an alkyl or cycloalkyl substituent at C-5 (step 8). After introduction of the $C_{1-5}$ alkyl or cycloalkyl moiety the remaining steps follow the sequence depicted in SCHEME A.

These general schemes suffice to prepare the compounds of the present invention Variations used to introduce C-6 functionality encompassed by the claimed compounds and used for specific compounds can be found in the examples which follow. Other approaches to introduce C-6 substituents can be found in the examples which follow.

Anti-Viral Activity

The activity of the inventive compounds as inhibitors of HCV activity may be measured by any of the suitable methods known to those skilled in the art, including in vivo and in vitro assays. For example, the HCV NS5B inhibitory activity of the compounds of formula I can determined using standard assay procedures described in Behrens et al., *EMBO J.* 1996 15:12-22, Lohmann et al., *Virology* 1998 249:108-118 and Ranjith-Kumar et al., *J. Virology* 2001 75:8615-8623. Unless otherwise noted, the compounds of this invention have demonstrated in vitro HCV NS5B inhibitory activity in such standard assays. The HCV polymerase assay conditions used for compounds of the present invention are described in Example 3. Cell-based replicon systems for HCV have been developed, in which the nonstructural proteins stably replicate subgenomic viral RNA in Huh7 cells (V. Lohmann et al., *Science* 1999 285:110 and K. J. Blight et al., *Science* 2000 290:1972. The cell-based replicon assay conditions used for compounds of the present invention are described in Example 4. In the absence of a purified, functional HCV replicase consisting of viral non-structural and host proteins, our understanding of Flaviviridae RNA synthesis comes from studies using active recombinant RNA-dependent RNA-polymerases and validation of these studies in the HCV replicon system. Inhibition of recombinant purified HCV polymerase with compounds in vitro biochemical assays may be validated using the replicon system whereby the polymerase exists within a replicase complex, associated with other viral and cellular polypeptides in appropriate stoichiometry. Demonstration of cell-based inhibition of HCV replication may be more predictive of in vivo function than demonstration of HCV NS5B inhibitory activity in vitro biochemical assays Dosage and Administration The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate. The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in Remington: The Science and Practice of Pharmacy 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent such as ribavirin, a nucleoside HCV polymerase inhibitor, another HCV non-nucleoside polymerase inhibitor or HCV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

In general a therapeutically effective amount of a compound of the present invention, and optionally one or more additional antiviral agents, is an amount effective to reduce the viral load or achieve a sustained viral response to therapy. Useful indicators for a sustained response, in addition to the viral load include, but are not limited to liver fibrosis, elevation in serum transaminase levels and necroinflammatory activity in the liver. One common example, which is intended to be exemplary and not limiting, of a marker is serum alanine transminase (ALT) which is measured by standard clinical assays. In some embodiments of the invention an effective treatment regimen is one which reduces ALT levels to less than about 45 IU/mL serum.

EXAMPLE 1

6-[(2-hydroxy-ethyl)-methanesulfonyl-amino]-5-methoxy-2-(4-phenylamino-phenyl)-benzofuran-3-carboxylic acid methylamide (I-1; SCHEME A)

step 1—To a solution of 5-methoxy-salicylaldehyde (6.0 g, 0.04 mol) and DCM (50 mL) was added $HBF_4.Et_2O$ (600 microliters). To the resulting solution was added dropwise over a 2 h period a solution of ethyl diazoacetate (6.84 g, 0.06 mol) and DCM (100 mL). The orange reaction mixture was concentrated and $H_2SO_4$ (1 mL) was added and the resulting mixture stirred for 30 min, then diluted with EtOAc, washed sequentially with water and brine, dried ($Na_2SO_4$), filtered and concentrated in vacuo. The crude product was purified by $SiO_2$ chromatography eluting with 5% EtOAc/hexane to afford 3.0 g of A-2a.

step 2—To a mixture of A-2a (2.5 g, 0.011 mol), trimethylborate (3.4 g, 0.024 mol) and anhydrous THF (100 mL) was cooled to −78° C. and maintained under a $N_2$ atmosphere and a solution of lithium diisopropylamide (12 mL, 1.8 M THF solution) was added and the yellow solution was stirred at −78° C. for 15 min. While at −78° C., the solution was quenched with 4N HCl, allowed to warm to RT and diluted with EtOAc. The solution was washed sequentially with $H_2O$ and brine, dried ($Na_2SO_4$), filtered and concentrated in vacuo. The residual boronic acid A-2b was used in the next step without further purification. The residue was dissolved in DME (50 mL) and $Na_2CO_3$ (4.6 g), $Pd(PPh_3)_4$ (0.6 g), 4-bromo-iodobenzene (7.8 g, 0.027 mol) and $H_2O$ (50 mL) were added and the resulting reaction mixture heated to 50° C. for 2 h. The reaction mixture was cooled to RT, diluted with EtOAc, washed sequentially with water and brine, dried ($Na_2SO_4$), filtered and in vacuo. The crude product was purified by $SiO_2$ chromatography eluting with an EtOAc/hexane gradient (0 to 10% EtOAc) to afford 1.1 g of A-2c.

step 3—To a solution of A-2c (1 g) and $CHCl_3$ (100 mL) cooled in an ice-bath was added 70% $HNO_3$ (5 mL). The resulting solution was stirred for 3 h. The reaction mixture was diluted with DCM, washed sequentially with water and brine, dried ($Na_2SO_4$), filtered and concentrated in vacuo. The residue was triturated with EtOAc/hexane and filtered to afford 0.9 g of A-3a. The filtrate contained additionally material along with some isomeric nitration product.

step 4—To a solution of A-3a from step 4 dissolved in DCM (50 mL)/HOAc (3 mL) was added Zn dust (5 g) and the resulting slurry stirred for 1 h. The solids were removed by filtration through CELITE® and the pad was further washed with DCM. The filtrate was evaporated and the solid trituated with EtOAc/hexane to afford 0.8 g of A-3b.

steps 5 & 6—To a ice-cold solution of A-3b (0.5 g) in pyridine (1 mL) and DCM (10 mL) was added mesyl chloride (0.3 mL) and the reaction was stirred for 20 min at RT. An additional aliquot of MsCl (0.2 mL) was added and stirring continued for 30 min. The reaction mixture was diluted with EtOAc, washed sequentially with dilute HCl, water and brine, dried ($Na_2SO_4$), filtered and evaporated to afford 0.3 g of A-3c. The resulting solid was suspended in MeCN (20 mL) and $K_2CO_3$ (0.5 g) and bromoethanol (0.5 g) were added. The reaction mixture was heated overnight at 80° C. The reaction mixture was cooled, diluted with EtOAc and washed sequentially with $H_2O$ and brine, dried ($Na_2SO_4$), filtered and evaporated. The crude product was purified by $SiO_2$ chromatography eluting with an EtOAc/DCM gradient (0 to 10% EtOAc) to afford 0.20 g of A-4.

steps 7 & 8—A mixture of A-4 (0.200 g) and NaOH (0.200 g) in MeOH (3 mL), THF (3 mL) and $H_2O$ (5 mL) was heated at 70° C. for 1 h. The reaction mixture was cooled to RT and acidified with dilute HCl and the resulting solid containing A-5a was filtered and dried in a vacuum oven at 50° C. The resulting solid was dissolved in DMF (3 mL) and HBTU (0.300 g) DIPEA (1 mL) and $MeNH_3{}^+Cl^-$ (0.200 g) was added. The reaction mixture was heated at 70° C. for 1 h. The reaction mixture was cooled to RT, diluted with $H_2O$ and stirred with 50% EtOAc/hexane. The remaining solid was collected by filtration and dried in vacuo at 50° C. to afford 0.15 g of A-5b.

step 9—A sealed tube was charged with crude A-5b (50 mg from the previous step), aniline (0.050 g), Pd[Pd(tert-Bu)$_3$] (0.010 g), NaOH (50 mg), toluene (2.5 mL) and DME (0.5 mL) and the resulting mixture was heated to 150° C. in a microwave reactor for 10 min. The reaction mixture was cooled to RT and the solvents evaporated in vacuo. The residue was purified by $SiO_2$ chromatography eluting with an acetone/DCM gradient (0 to 20% acetone). The recovered solid was triturated with EtOAc/hexane to afford 0.018 g of I-1: mp 187.1-191° C.

The following were prepared analogously except in step 9 aniline was replaced with I-2 (p-fluoro-aniline), I-3 (p-chloro-aniline), I-5 (o-fluoro-aniline), I-6 (4-iso-propyl-aniline), I-7 (m-methoxy-aniline), I-10 (3,4-difluoro-aniline), I-11 (p-trifluoromethyl-aniline), I-12 (m-amino-benzonitrile), I-13 (p-amino-benzonitrile), I-14 (2,4-difluoro-aniline), I-15 (3-chloro-4-fluoro-aniline), I-16 (3,5-difluoro-aniline), I-19 (4-chloro-aniline), I-20 (4-methyl-aniline), I-21 2,3-difluoro-aniline) I-122 (3-amino-pyridine), I-123 (2-aminopyridine) and I-124 (2-amino-5-fluoro-pyridine).

I-17 and I-18 are prepared from A-3c except the alkylating agent in step 6, is iodoethane rather than bromoethanol and the Suzuki in step 9 is carried out with p-fluoro-aniline and o-fluoro-aniline respectively rather than aniline.

The following biphenyl ethers are prepared analogously except in step 9, aniline is replaced by the phenol in parentheses: I-44 (o-chloro-phenol); I-45 (3,4-difluoro-phenol), I-47 (m-hydroxy-benzonitrile), I-48 (p-hydroxy-benzonitrile).

The following biphenyl ethers are prepared analogously except in step 9, aniline is replaced by the phenol in parentheses and in the N-alkylation in step 6 bromoethanol is replaced with the designated alkylating agent: I-35 (p-fluorophenol, methyl iodide), I-36 (o-fluorophenol, methyl iodide), I-47 (3,5-difluorophenol, methyl iodide), I-37 (3,5-difluorophenol, methyl iodide).

I-43 is prepared analogously except step 6 is omitted.

EXAMPLE 2

6-[(2-Hydroxy-ethyl)-methanesulfonyl-amino]-5-methoxy-2-(4-phenoxy-phenyl)-benzofuran-3-carboxylic acid methylamide (I-4)

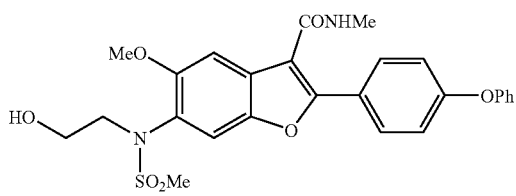

To a solution of A-4 (0.020 g), phenol (0.050 g), di-tert-butyl(2', 4', 6'-triisopropyl-biphenyl-2-yl)-phosphane (0.006 g), Pd(OAc)$_2$ (0.003 g), K$_3$PO$_4$ (0.020 g) and toluene (2 mL) were heated at 100° C. for 4 h. The solution was cooled, diluted with DCM washed with brine, dried (Na$_2$SO$_4$), filtered and evaporated. The crude product was purified by SiO$_2$ chromatography eluting with an acetone/DCM gradient (0 to 20% acetone) to afford 0.013 g (52%) of 19. Conversion of 19 to I-4 was carried out by the procedures described in steps 7 and 8 of example 1.

I-8, I-9, I-22, I-25 and I-38 were prepared analogously except phenol was replaced with 4-fluoro-phenol and 2-fluoro-phenol, 2,3-difluoro-phenol, 2,6-difluoro-phenol and m-chloro-phenol respectively I-23 and I-24 are prepared by analogous procedures except in step 6 of example 1, bromoethanol was replaced with ethyl iodide and phenol in example 2 is replaced with o-fluoro-phenol and p-fluoro-phenol respectively.

EXAMPLE 3

5-Cyclopropyl-2-[4-(4-fluoro-phenoxy)-phenyl]-6-[(2-hydroxy-ethyl)-methanesulfonyl-amino]-benzofuran-3-carboxylic acid methylamide (I-32)

step 1—To a suspension of NaH (16 g, 0.4 mol, 60% mineral oil dispersion) and toluene (300 mL) at RT was added dropwise diethyl carbonate (61 mL, 0.5 mol) over a 1 h period a solution of B-1a (20 g, 0.1 mol). The solution was heated at reflux overnight then cooled to RT and quenched with glacial HOAc followed by a solution of con HCl (40 mL) and ice water (300 mL). The layers were separated and the aqueous layer was twice extracted with EtOAc. The combined organic extracts were washed sequentially with sat'd. NaHCO$_3$ and brine, dried (Na$_2$SO$_4$), filtered and evaporated. The crude product was distilled (135° C./0.8 Torr) to afford 17.6 g of B-1b.

step 2—A three-neck flask was charged with ZnCl$_2$ (3.0 g, 22.13 mmol) and heated at 100° C. in a vacuum oven for 1 h. To the resulting solid was added anhydrous EtOH (105 mL) and B-1b (6.0 g, 22.13 mmol) and the mixture heated to 110° C. The flask was fitted with a dropping funnel charged with quinone (2.39 g, 22.13 mmol) and EtOH was introduced by evaporating the EtOH in the flask through the side arm and condensing the vapor in the dropping funnel (ca. 12 mL) which slowly dissolved the solid quinone overnight and added the quinone to the mixture of ZnCl$_2$ and B-1b (ca. 18 h). The solution was cooled and partitioned between EtOAc and brine and the organic phase dried (Na$_2$SO$_4$), filtered and evaporated. The crude product was purified by SiO$_2$ chromatography eluting with 15% EtOAc/hexane to afford 2.83 g of B-2a as a cream colored solid. The solid contained a small amount of an impurity that could be removed by washing with a small amount of EtOAc.

step 3—To a solution of B-2a (2.85 g, 7.87 mmol) in anhydrous NMP (10 mL) was added Cs$_2$CO$_3$ (5.12 g, 15.347 mmol) and the resulting solution stirred at RT for 10 min. 2-Bromopropane (2.2 mL, 23.61 mmol) was added and the resulting solution heated at 50° C. for 6 h. The reaction mixture was diluted with EtOAc and thrice washed with H$_2$O. The EtOAc solution was dried (Na$_2$SO$_4$), filtered and evaporated to afford 3.55 g (100%) of B-2b which was used without further purification.

step 4—To a solution of B-2b (3.5 g, 8.66 mmol) in CHCl$_3$ (12 mL) at ca. 20° C. was added dropwise 70% HNO$_3$ (8.8 g) and the resulting solution stirred for 1 h. The reaction mixture was diluted with H$_2$O and the CHCl$_3$ layer separated and thrice washed with H$_2$O. The organic solution was dried (Na$_2$SO$_4$), filtered and evaporated to afford 2.47 g of pure B-3.

step 5—To a mixture of B-3 (1.0 g, 2.46 mmol), p-fluorophenol, K$_3$PO$_4$ (1.0 g, 4.92 mmol), di-tert-butyl-(2',4',6'-tri-iso-propy 1-biphenyl-2-yl)-phosphane (20, 0.73 g, 0.172 mmol, CASRN 564483-19-8) in toluene (2 mL, degassed with N$_2$) was added Pd(OAc)$_2$ and the solution was heated to 100° C. overnight. The solution was diluted with water and the aqueous phase extracted with EtOAc. The combined extracts were dried (Na$_2$SO$_4$), filtered and evaporated. The crude product was purified by SiO$_2$ chromatography eluting with an EtOAc/hexane gradient (0 to 20% EtOAc) to afford 0.957 g (76%) of B-4a (Ar=p-fluorophenyl).

step 6—To a solution of B-4a (0.45 g, 0.94 mmol) and DCM (20 mL) at RT was added dropwise BCl$_3$ (4.5 mL, 4.50 mmol, 1 M solution in hexane). The solution was stirred for 6 h then poured into ice-water and the resulting mixture extracted with DCM. The organic extract was washed twice with H$_2$O, dried (Na$_2$SO$_4$), filtered and evaporated. The resulting solid was triturated with hexane and filtered to afford 2.09 g of B-4-b. The hexane wash was evaporated and the resulting solid purified by SiO$_2$ chromatography eluting with an EtOAc/hexane gradient (0 to 20% EtOAc) to afford an addition 1.0 g of B-4-b.

step 7—To a solution of B-4-b (1.0 g, 0.91 mmol) in DCM was added DIPEA (0.17 mL 1.0 mmol) and DMAP (0.011 g, 0.09 mmol) and the solution was cooled to 0° C. and triflic anhydride (0.28 g, 1.0 mmol) was added and the resulting solution stirred overnight. The resulting solution was twice washed with H$_2$O then brine, dried (Na$_2$SO$_4$), filtered and concentrated. The crude product was purified by SiO$_2$ chromatography eluting with an EtOAc/hexane gradient (0 to 20% EtOAc) to afford 0.465 g of B-4c.

step 8—A mixture of B-4c (0.46 g, 0.81 mmol), cyclopropaneboronic acid (0.076 g, 0.89 mmol), KF.2H$_2$O (0.25 g, 2.67 mmol), NaBr (0.083 g, 0.81 mmol), Pd(PPh$_3$)$_4$ (0.028 g, 0.024 mmol) and anhydrous toluene (3 mL) was degassed by bubbling N$_2$ then heated at reflux overnight. The solution was cooled to RT, water added and the resulting mixture extracted with EtOAc. The extract was dried (Na$_2$SO$_4$), filtered and concentrated. The crude product was purified by SiO$_2$ chromatography eluting with an EtOAc/hexane gradient to afford 0.372 g of B4d.

step 9—A suspension of B-4-d (0.37 g, 0.803 nmol), 10% Pd/C (0.050 g) and EtOAc (10 mL) was stirred overnight under 1 atmosphere of H$_2$. The catalyst was removed by filtration through filtering agent and the resulting solution concentrated to afford 0.292 g of B-5a.

step 10—To a solution of B-5a (0.29 g, 0.67 mmol) in DCM (5 mL) cooled to 0° C. was added sequentially pyridine (0.74 mg, 1.01 mmol) and mesyl chloride (0.065 g, 0.74 mmol). The resulting solution was stirred at RT overnight then concentrated. The crude product was purified by $SiO_2$ chromatography eluting with an EtOAc/hexane gradient (0 to 30% EtOAc) to afford 0.344 g of B-5b.

step 11—To a solution of B-5b (0.1 g, 0.197 mmol), $K_2CO_3$ (0.081 g, 0.590 mmol, 2-bromoethanol (0.050 g, 0.394 mmol) in anhydrous MeCN (5 mL) was heated at reflux overnight. The resulting solution was concentrated and purified by $SiO_2$ chromatography eluting with an EtOAc/hexane gradient (0 to 40% EtOAc) to afford 0.102 g of B-5c.

step 12—A solution of B-5c (0.1 g, 0.181 mmol), KOH (0.1 g, 1.81 mmol) in EtOH (3 mL) and water (1.5 mL) was heated at reflux for 2 h, cooled and concentrated in vacuo. The pH was adjusted to ca. 1 with 1N HCl and the resulting precipitate was filtered and washed with $H_2O$ and dried to afford 0.096 g of B-6a.

step 13—A mixture of B-6a (0.095 g, 0.181 mmol), HBTU (0.075 g, 0.200 mmol), $MeNH_3^+Cl^-$ (0.12 g, 1.81 mmol), DIPEA (0.30 mL, 1.81 mmol) and anhydrous DMF was heated at 80° C. for 3 h. The solution was cooled and partitioned between EtOAc/hexane and the organic phase thrice washed with $H_2O$, dried ($Na_2SO_4$), filtered and concentrated. The crude product was purified by $SiO_2$ chromatography eluting with 70% EtOAc/hexane to afford 0.061 g of I-32 as a white solid.

The following compounds are prepared analogously except in step 5, p-fluorophenol is replaced with the phenol in parentheses: I-33 (phenol), I-58 (2,4-difluoro-phenol), I-61 (o-fluorophenol).

I-40 is prepared analogously except the N-alkylation in step 11 was omitted.

The biphenyl amine I-62 is prepared analogously except in step 5, p-fluoro-phenol is replaced with p-fluoro-aniline. Representative procedures which are adaptable to coupling aniline and phenol derivatives to haloalkanes such as B-3 are described in step 5 of the current example and step 3 of example 1.

I-53 is prepared analogously except in step 6, bromoethanol is replaced with tert-butyl N-(2-iodoethyl)-carbamic acid (CASRN 122234-46-2). The Boc protecting groups were removed with 1M HCl in $Et_2O$ in anhydrous DCM/MeOH.

I-77 is prepared by alkylation of B-5a with bis-(2-chloroethyl)ether (CASRN 111-44-4).

EXAMPLE 4

5-Ethyl-2-[4-(4-fluoro-phenoxy)-phenyl]-6-[(2-hydroxy-ethyl)-methanesulfonyl-amino]-benzofuran-3-carboxylic acid methylamide (I-51)

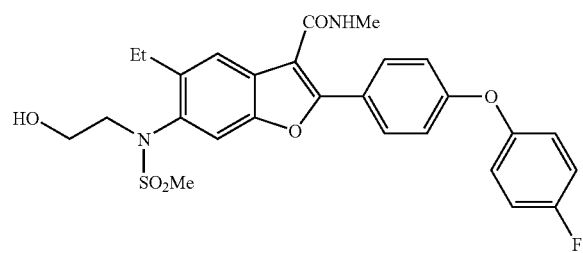

step 1—A solution of B-4c (0.20 g, 0.352 mmol), cesium trifluoro(vinyl)borate (0.052 g, 0.387 mmol), $Cs_2CO_3$ (0.034 g, 1.06 mmol), dicyclopentyl-(2',6'-dimethoxy-biphenyl-2-yl)-phosphane (22, 0.009 g, 0.02 mmol), $Pd(OAc)_2$ (0.002 g, 0.007 mmol) and $THF/H_2O$ (9:1, 5 mL) was degassed with a $N_2$ purge and heated at 80° C. overnight. The solution was cooled to RT and filtered through CELITE® and concentrated. The crude product was purified by $SiO_2$ chromatography eluting with an EtOAc/hexane gradient (0 to 2.5% EtOAc) to afford 0.052 g of ethyl 2-[4-(4-fluoro-phenoxy)-phenyl]-6-nitro-S-vinyl-benzofuran-3-carboxylate (24).

step 2—A suspension of 24 (0.052 g), Pd/C (0.010 g) and EtOAc (5 mL) was stirred overnight at RT under 1 atmosphere of $H_2$. The solution was filtered through CELITE and concentrated to afford 0.045 g of ethyl 6-amino-5-ethyl-2-[4-(4-fluoro-phenoxy)-phenyl]-benzofuran-3-carboxylate (26).

The amine 26 is converted to I-51 by the procedures described in steps 10 to 13 of example 3.

I-52 is prepared analogously from 26 by the procedures in steps 10-13 of example 3 except in step 1, bromoethanol is replaced with iodomethane.

EXAMPLE 5

5-Cyclopropyl-2-[4-(4-fluoro-phenoxy)-phenyl]-6-(methanesulfonyl-oxetan-3-ylmethyl-amino)-benzofuran-3-carboxylic acid methylamide (I-70)

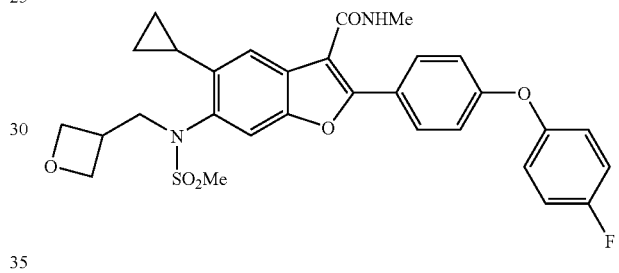

B-5b is converted to 5-cyclopropyl-2-[4-(4-fluoro-phenoxy)-phenyl]-6-methanesulfonylamino-benzofuran-3-carboxylic acid (28) as described in step 12 of example 3.

step 1—To a solution of 28 (0.51 g, 1.07 mmol) in dry DMF (5 mL) was added CDI (0.19 g, 1.17 mmol) and the solution stirred at RT for 2 h. Methyl amine hydrochloride (0.72 g, 10.7 mmol) and DIPEA (1.4 g, 10.7 mmol) were added and the resulting solution heated at 85° C. for 3 h. The solution was cooled and partitioned between EtOAc and $H_2O$. The organic phase was dried ($Na_2SO_4$), filtered and concentrated. The crude product was purified by $SiO_2$ chromatography eluting with an EtOAc/hexane gradient (0 to 40% EtOAc) to afford 0.426 g of 5-cyclopropyl-2-[4-(4-fluoro-phenoxy)-phenyl]-6-methanesulfonylamino-benzofuran-3-carboxylic acid methylamide (30).

step 2—To a solution of 30 (0.050 g, 0.10 mmol), 3-iodomethyl-oxetane (0.030 g, 0.15 mmol, CASRN 1003013-77-1) and $K_2CO_3$ (0.041 g, 0.30 mmol) in dry DMF (0.5 mL) was heated at 85° C. for 3 h. The reaction mixture was cooled and partitioned between EtOAc and $H_2O$. The organic phase was dried ($Na_2SO_4$), filtered and evaporated. The crude product was purified by $SiO_2$ chromatography eluting with an EtOAc/hexane gradient (0 to 70% EtOAc) to afford 0.054 g of I-70.

The following compounds were prepared analogously except in step 2, 3-iodomethyl-oxetane was replaced with the alkylating agent in parentheses: I-41 (methyl iodide), I-42 (ethyl iodide), I-56 (tetrahydro-4-(iodomethyl)-2H-pyran, CASRN 101691-94-5), I-57 (1-bromo-2-methoxy-ethane, CASN 6482-24-2), I-60 (3-iodomethyltetrahydrofuran, CASRN 475090-43-6), I-68 (1-bromo-propan-2-ol), I-71 4-bromomethyl-pyridinium hydrobromide, CASRN 73870-24-3), I-72 (tetrahydro-4-iodo-2H-pyran, CASRN 25637-18-7), I-73 (iodoacetamide, CASRN 144-48-9), I-84 (3-bromotetrahydrofuran, CASRN 19311-37-6), I-87 (3-bromomethyl-3-methyl-oxetane, CASRN 78385-26-9), I-88 (5-bromomethyl-pyrimidine, CASRN 25198-96-3) I-96 (3-bromobutyronitrile, CASRN 5332-06-9), and I-106 (3-bromo-propanol).

I-69, I-74, I-92 and I-95 are prepared analogously except in step 2,3-iodomethyl-oxetane is replaced with tert-butyl N-(3-iodopropyl)-carbamic acid (CASRN 167479-01-8) and tert-butyl N-(2-iodoethyl)-carbamic acid (CASRN 122234-46-2) and tert-butyl N-(4-bromobutyl)-carbamic acid (CASRN 164365-88-2) and (2-bromopropyl)-carbamic acid, 1,1-dimethylethyl ester (CASRN 121102-88-3) respectively. The Boc protecting groups were subsequently removed with TFA in DCM or $CHCl_3$. I-79 is prepared by acetylation of I-74 (supra) with acetic anhydride and pyridine in DCM. The final product was purified on a preparative $SiO_2$ plate developed with 90% EtOAc/hexane. I-80 and I-116 were prepared by sulfonylation of I-74 and I-69, respectively, with mesyl chloride and TEA.

I-116 was prepared by treating a DCM solution of I-69 with mesyl chloride (1.5 equivalents) and dry pyridine (3.5 equivalents). I-116 was purified by $SiO_2$ chromatography eluting with 5% MeOH/DCM followed by preparative $SiO_2$ TLC developed with 5% MeOH/DCM. I-117 can be prepared by N-alkylation of I-116 with iodomethane in the presence of an alkali or alkaline metal carbonate and MeCN.

I-75—was prepared analogously except in step 2,3-iodomethyl-oxetane was replaced with tert-butyl 3-iodo-1-azetidinecarboxylate (CASRN 254454-54-1) and the Boc protecting group was subsequently removed by contacting a solution of the product from the alkylation step in DCM/MeOH with 1N HCl in $Et_2O$ at RT overnight to afford I-75.

I-76 is analogously except in step 2,3-iodomethyl-oxetane was replaced with 1-(tert-butoxycarbonyl)-4-iodopiperidine (CASRN 301673-14-3).

I-99 and I-100 were prepare analogously except in step 2,3-iodomethyl-oxetane was replaced with 4-iodo-cyclohexanol. The reaction was sluggish and the reaction mixture was heated for several days with periodic addition of 4-iodo-cyclohexanol. Eventually two new products were detected along with starting material. The reaction was worked up in the normal manner and purified by $SiO_2$ chromatography eluting with 30, 40 and 80% EtOAc/hexane. Fractions contained the new products were further purified on a preparative $SiO_2$ plate developed with 10% acetone/DCM followed by 80% EtOAc/hexane to afford 14 mg (15%) of I-99 and 7.5 mg (7.5%) of I-100

EXAMPLE 6

6-[(4-Amino-cyclohexyl)-methanesulfonyl-amino]-5-cyclopropyl-2-[4-(4-fluoro-phenoxy)-phenyl]-benzofuran-3-carboxylic acid methylamide (I-98)

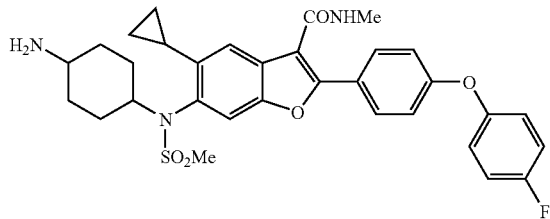

(4-Iodo-cyclohexyl)-carbamic acid, tert-butyl ester—To a mixture of $Ph_3P$ (0.79 g, 3.02 mmol) and imidazole (0.41 g, 3.03 mmol) in DCM cooled to 0° C. was added iodine (0.77 g, 3.02 mmol) and the mixture stirred at 0° C. until the iodine dissolved. A solution of (4-hydroxy-cyclohexyl)-carbamic acid tert-butyl ester (0.5 g, 2.32 mmol, CASRN 224309-64-2) and DCM was then added dropwise and stirring continued for 30 min at 0° C., then at RT for 1 h. The reaction mixture was poured into ice-$H_2O$ and twice extracted with DCM. The combined extracts were dried ($Na_2SO_4$), filtered and evaporated. The crude product was purified by $SiO_2$ chromatography eluting with an EtOAc/hexane gradient (0 to 20% EtOAc) to afford 0.338 g of 32 as a white solid.

step 1—[4-({5-Cyclopropyl-2-[4-(4-fluoro-phenoxy)-phenyl]-3-methylcarbamoyl-benzofuran-6-yl}-methanesulfonyl-amino)-cyclohexyl]-carbamic acid tert-butyl ester (34) was prepared by alkylation of 30 (0.05 g, 0.104 mmol) with 32 (0.051 g, 0.156 mmol) in accord with the procedure in step 2 of example 5 to afford 8 mg of 34 which was purified on a preparative $SiO_2$ TLC plate developed with 1:1 EtOAc/hexane.

step 2—A solution of 34 (8 mg), 1M HCl/$Et_2O$ (3 mL) and DCM (3 mL) was stirred at RT overnight. The solvent was evaporated and the solid triturated three times with ether to afford 2 mg of (I-98)

I-108 was prepared analogously except in step 1, 32 was replaced with tert-butyl 4-iodomethyl-2-oxo-oxazolidine-3-carboxylate CASRN 197389-07-4) and step 2 was omitted.

EXAMPLE 7

6-[(3-Amino-2,2-difluoro-propyl)-methanesulfonyl-amino]-5-cyclopropyl-2-[4-(4-fluoro-phenoxy)-phenyl]-benzofuran-3-carboxylic acid methylamide; hydrochloride salt (I-115)

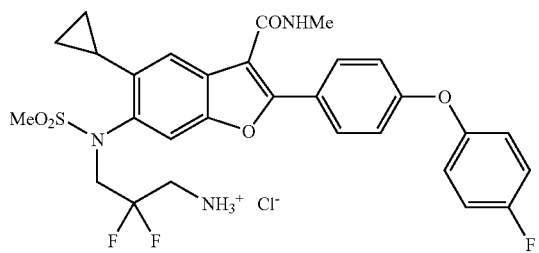

step 1—[4-({5-Cyclopropyl-2-[4-(4-fluoro-phenoxy)-phenyl]-3-methylcarbamoyl-benzofuran-6-yl}-methanesulfonyl-amino)-2-hydroxy-propyl]-carbamic acid tert-butyl ester was prepared by alkylation of 30 (0.3 g, 0.6 mmol) with 40b (0.3 g, 1.2 mmol, see example 10) in accord with the procedure in step 2 of example 5 to afford 248 mg of [3-({5-cyclopropyl-2-[4-(4-fluoro-phenoxy)-phenyl]-3-methylcarbamoyl-benzofuran-6-yl}-methanesulfonyl-amino)-2-hydroxy-propyl]-carbamic acid (36) which was purified by $SiO_2$ chromatography eluting with an EtOAc/hexane gradient (0 to 50% EtOAc).

step 2—A solution of 36 (0.178 g, 0.267 mmol), PCC (0.114 g, 0.680 mmol), NaOAc (214 mg) and DCM (8 mL) was added stirred overnight. The solvent was evaporated and the crude product purified on a $SiO_2$ column eluting with an EtOAc/hexane gradient (0 to 50% EtOAc) to afford 0.081 g of [3-({5-cyclopropyl-2-[4-(4-fluoro-phenoxy)-phenyl]-3-methylcarbamoyl-benzofuran-6-yl}-methanesulfonyl-amino)-2-oxo-propyl]-carbamic acid tert-butyl ester (38).

step 3—To a solution of 38 (0.060 g, 0.090 mmol) in DCM (3 mL) was added a solution of morpholino sulfur trifluoride and the resulting solution stirred for 2 d. The reaction was quenched by adding sat'd. $NaHCO_3$ and the resulting solution extracted with DCM. The combined DCM extracts were dried (Na$_2$SO$_4$), filtered and evaporated. The crude product was purified on a preparative SiO$_2$ TLC plate to afford 12 mg of 40.

step 4—A solution of 40 (0.024 g), 1M HCl/ether (5 mL) in MeOH (2 mL) and DCM (2 mL) was stirred for 6 h at RT then evaporated. The resulting solid was washed sequentially with hexane, ether and EtOAc and filtered to afford 0.018 g of I-115.

EXAMPLE 8

5-Cyclopropyl-2-[4-(4-fluoro-phenoxy)-phenyl]-6-[methanesulfonyl-(2-sulfamoyl-ethyl)-amino]-benzofuran-3-carboxylic acid methylamide (I-119)

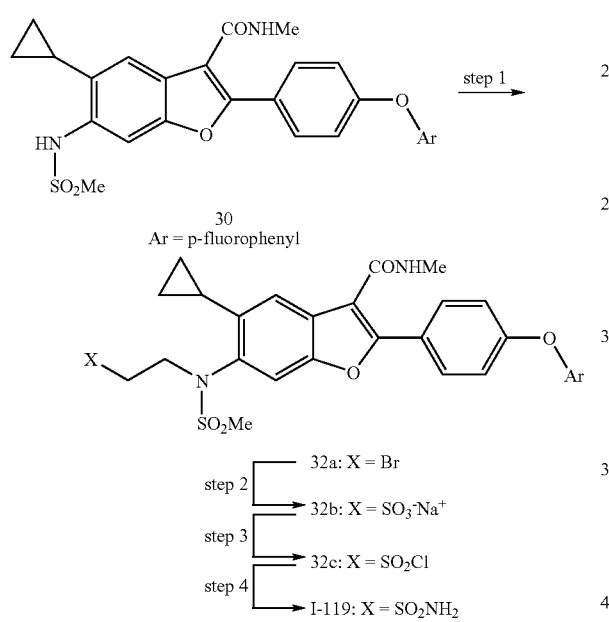

step 1—A mixture of 30 (0.20 g, 0.405 mmol), dibromoethane (1.1 g, 6.0 mmol), K$_2$CO$_3$ (0.83 g, 6.0 mmol) and dry DMF (10 mL) was heated at 50° C. for 3 h. The solvent was removed in vacuo and the residue partitioned between EtOAc and H$_2$O. The EtOAc extracts were combined, dried (Na$_2$SO$_4$), filtered and evaporated. The crude product was purified by SiO$_2$ chromatography eluting with an EtOAc/hexane gradient (0 to 60% EtOAc) to afford 0.242 g of 32a.

step 2—To a solution of 32a (0.240 g, 0.40 mmol) and EtOH (2 mL) was added to a solution of Na$_2$SO$_3$ (0.060 g, 0.48 mmol) and H$_2$O (3 mL) and the resulting solution heated at reflux overnight. Addition of more Na$_2$SO$_3$ did not result in additional conversion to the product. The solvents were evaporated and the residual solid washed with water and DCM which afforded 0.035 g of 32b as a white solid.

step 3—To a suspension of 32b (0.030 g, 0.05 mmol) in dry benzene was added SOCl$_2$ (0.012 g) and one drop of DMF and the resulting solution was heated at reflux overnight. The solvents were evaporated and the resulting crude sulfonyl chloride 32c was used in the next step without further purification.

step 4—To a solution of 32c (0.035 g) in DCM (2 mL) was added a 0.5 M solution of NH$_3$ in dioxane (2 mL) and the resulting solution stirred at RT for 3 h then concentrated in vacuo. The crude product was purified on a preparative SiO$_2$ TLC plate developed with 5% MeOH/DCM to afford 6 mg of I-119. The major byproduct was 30 which was formed by elimination of ethenesulfonic acid amide.

I-118 was prepared analogously except in step 1, 1,3-dibromopropane was used in place of 1,2-dibromoethane.

EXAMPLE 9

6-[(2-Hydroxy-ethyl)-methanesulfonyl-amino]-5-isopropoxy-2-(4-phenylamino-phenyl)-benzofuran-3-carboxylic acid methylamide (I-28)

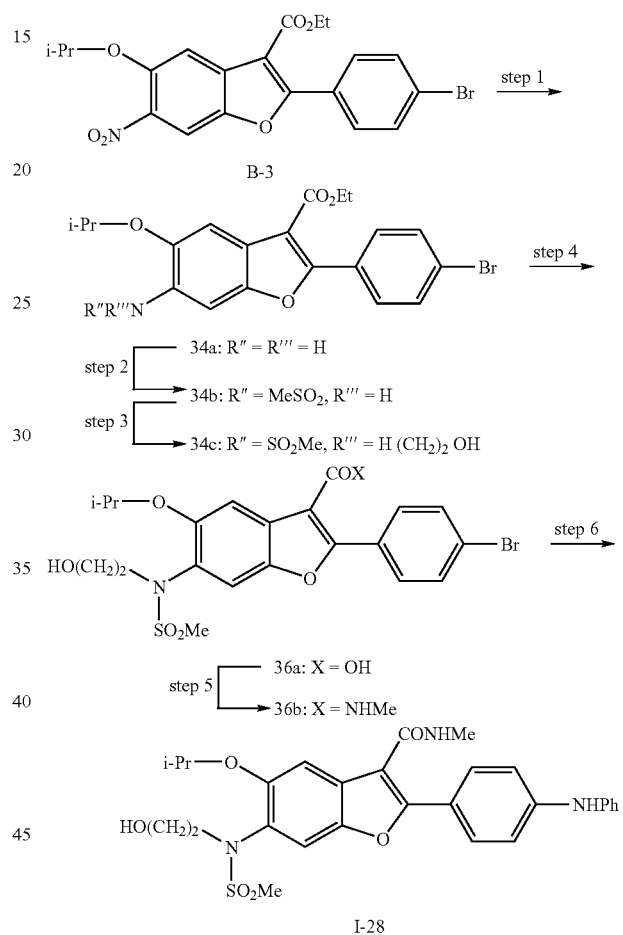

step 1—To a suspension of B-3 (4.99 g, 11.1 mmol) in EtOH (240 mL) and H$_2$O (40 mL) was added iron powder (4.35 g, 77.9 mmol) and NH$_4$Cl (4.06 g, 77.9 mmol) and the resulting mixture heated at 80° C. for 4 h. The reaction was cooled, filtered through CELITE and the pad was washed with DCM and MeOH. The filtrate was concentrated and the residue dissolved in DCM and filtered. The DCM was evaporated and the crude product purified by SiO$_2$ chromatography eluting with 15% EtOAc/hexane to afford 4.15 g of 34a as a yellow solid.

34a is converted into 2-(4-bromo-phenyl)-6-[(2-hydroxy-ethyl)-methanesulfonyl-amino]-5-isopropoxy-benzofuran-3-carboxylic acid methylamide (36b) as depicted in steps 2 to 5 of the present example using procedures described in steps 10 to 13 of example 3 step 6—A vial was charged with 36b (0.075 g, 0.14 mmol), K$_3$PO$_4$ (0.091 g, 0.43 mmol), Pd(OAc)$_2$ (0.016 g, 0.07 mmol), 20 (0.030 g, 0.07 mmol), aniline (0.04 mL, 0.43 mmol) and toluene (7.5 mL), sealed and heated at 100° C. overnight. The vial was cooled and concentrated. The residue was taken up in acetone/DCM and applied to a SiO₂ chromatography column and eluted with a DCM/acetone gradient (10 to 15% acetone). The recovered solid was run through a plug of SiO₂ and eluted with 5% MeOH/DCM followed by a SiO₂ column eluting with EtOAc to afford 0.024 g of I-28.

The following compounds were prepared analogously except in step 6, aniline was replaced with the substituted aniline in parentheses: I-29 (m-fluoro-aniline), I-30 (p-chloro-aniline), I-31 (p-fluoro-aniline) and I-34 (o-fluoro-aniline).

The following compounds were prepared analogously except in step 6, aniline was replaced with the substituted phenol in parentheses: I-26 (m-fluoro-phenol), I-27 (p-chloro-phenol), I-39, (2,4-difluoro-phenol), I-46 (m-chloro-phenol), I-49 (chlorophenol) and I-50 (3,4-difluoro-phenol).

EXAMPLE 10

6-[(3-Amino-2-hydroxy-propyl)-methanesulfonyl-amino]-5-cyclopropyl-2-[4-(4-fluoro-phenoxy)-phenyl]-benzofuran-3-carboxylic acid methylamide; hydrochloride salt (I-97)

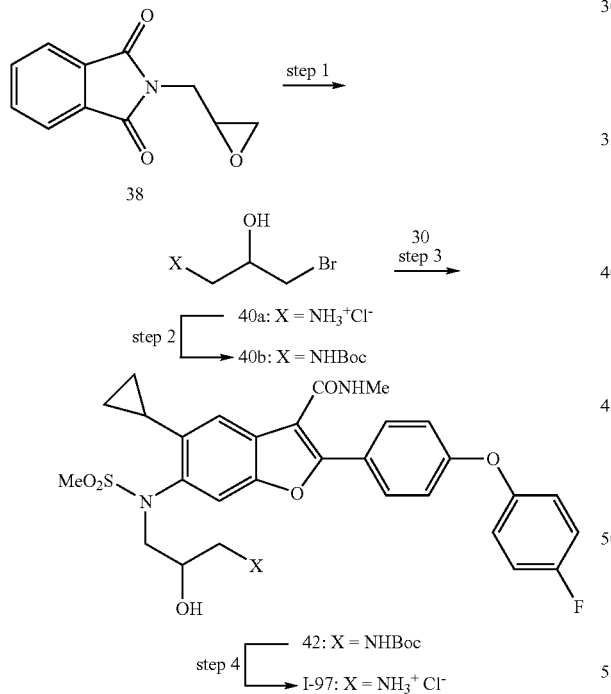

step 1—A solution of 38 (5 g, 24.6 mmol, CASRN 5455-98-1) and 48% aq HBr (26 mL) was heated at reflux overnight. The solution was cooled and concentrated. The residue was twice azeotroped with toluene and the residue triturated three times with Et₂O then three times with CHCl₃ to afford 12.1 g of sticky crystals. The crystals were twice washed with IPA then dried to afford 6.74 g a ca. 1:1 mixture of 40a and phthalic acid which was used directly in the next step.

step 2—To a suspension of 40a from step 1 (2.36 g calculated based on purity, 10.0 mmol) in a mixture of DCM (40 mL) and MeOH (10 mL) cooled to −13° C. was added a solution of (Boc)₂O (3.29 g, 15.1 mmol) and DCM (3 mL) followed by TEA (2.1 mL, 15.1 mmol). The reaction was stirred overnight at RT then concentrated. The residue was purified by SiO₂ chromatography eluting with 10% MeOH/DCM to afford 451 mg or pure 40b in one fraction and another 824 mg of impure product in two following fractions.

step 3—A solution of 30 (0.300 g, 0.61 mmol), 40b (0.185 g, 0.73 mmol), K₂CO₃ (0.252 g, 1.82 mmol) and dry DMF (4 mL) was heat at 85° C. for 6 h. Analysis of the product mixture indicated unreacted 30 remained and additional 40b (0.100 g) in DMF (3 mL) and K₂CO₃ (0.100 g) were added and heating continued overnight. The reaction mixture was cooled and partitioned between EtOAc (200 mL) and H₂O (90 mL). The EtOAc phase was washed with H₂O (50 mL), dried (Na₂SO₄), filtered and evaporated. The crude product was purified by SiO₂ chromatography eluting with 60% EtOAc/hexane to afford 203 mg of 42.

step 4—To a solution of 42 (20 mg), dry MeOH (0.5 mL), dry DCM (5 mL) was added 1M HCl in Et₂O (1 mL) and the reaction mixture aged overnight. The reaction mixture was concentrated and the resulting solid washed with Et₂O and dried. The resulting solid was triturated with DCM in a vial and the solvent evaporated to afford a quantitative yield of I-97.

EXAMPLE 11

5-Cyclopropyl-2-[4-(4-fluoro-phenoxy)-phenyl]-6-[methanesulfonyl-(2-methylsulfanyl-ethyl)-amino]-benzofuran-3-carboxylic acid methylamide (I-81) and 5-cyclopropyl-2-[4-(4-fluoro-phenoxy)-phenyl]-6-[methanesulfonyl-(2-methanesulfonyl-ethyl)-amino]-benzofuran-3-carboxylic acid methylamide (I-83)

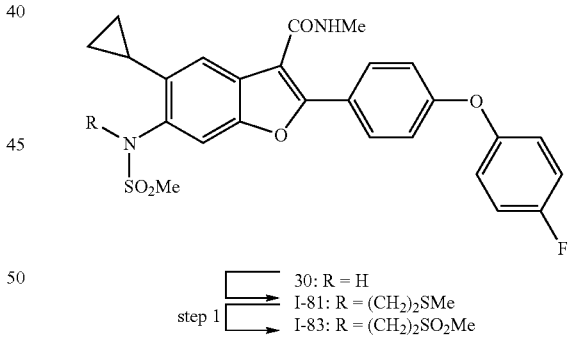

I-81 was prepared from 30 in accord with the procedure in step 2 of example 5 except 3-iodomethyl-oxetane was replaced with 1-iodo-2-(methylthio)ethane (CASRN 108122-14-1).

step 1—To a solution of I-81 (0.045 g, 0.08 mmol) in MeOH (2.7 mL) was added sequentially H₂O (0.9 mL) and OXONE® (0.049 g, 0.08 mmol, potassium peroxomonosulfate) and the resulting reaction mixture stirred at RT for 2 h. LCMS indicated significant amounts of sulfoxide were still present and additional OXONE (0.048 g) was added and the reaction kept overnight in a refrigerator. The reaction mixture was concentrated and partitioned between DCM (20 mL) and 1M NaOH (1 mL). The organic phase was dried (Na₂SO₄), filtered and evaporated. The crude product was purified by SiO$_2$ chromatography eluting with 5% acetone/DCM to afford 0.023 g of I-83.

I-113 and I-114 are prepared analogously except 1-iodo-2-(methylthio)ethane was replaced with 1-bromo-3-(methylthio)propane (CASRN 68734-27-1).

EXAMPLE 12

2-[4-(2-Fluoro-phenoxy)-phenyl]-6-[(2-hydroxyethyl)-methanesulfonyl-amino]-5-propyl-benzofuran-3-carboxylic acid methylamide (I-65)

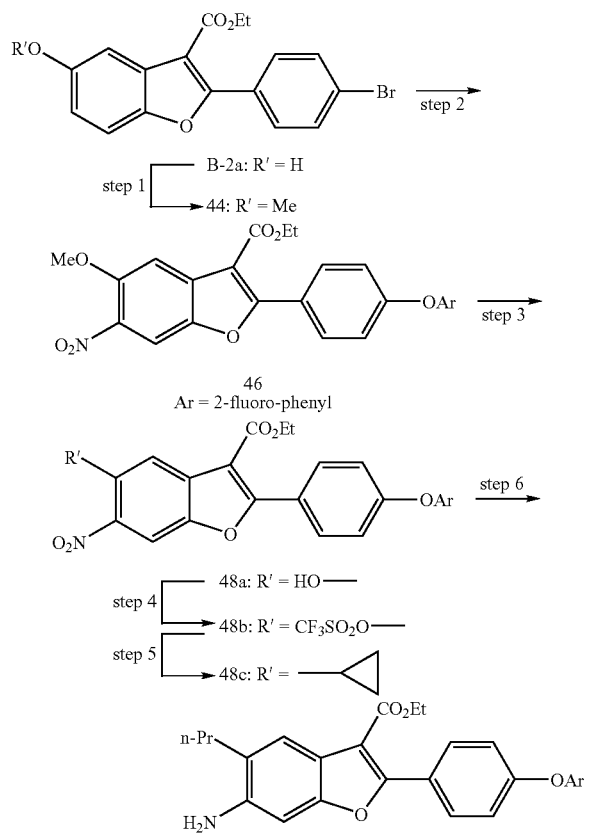

The preparation of 48c from B-2a is carried out as described in steps 3-8 of example 3 except in step 1 of the current example iso-propyl bromide is replaced with methyl iodide to afford the methyl ether.

step 6—A suspension of 48c (0.26 g, 0.563 mmol) 10% Pd/C (0.030 g) and EtOAc (10 mL) was stirred was stirred at RT overnight under a H$_2$ atmosphere maintained by a H$_2$-filled balloon. The catalyst was removed by filtration through filtering aid, washed with DCM and the combined filtrates were evaporated. The crude product was purified by SiO$_2$ chromatography eluting with 20 and 30% EtOAc/hexane to afford 34 mg of 50 and 0.19 g of the corresponding compound wherein the cyclopropyl remained intact.

Further conversion of 50 to I-65 by hydrolysis of the ethyl ester and formation of the methylamide is carried out in accord with the procedures in steps 10 to 13 of example 3.

EXAMPLE 13

5-Cyclopropyl-2-[4-(4-fluoro-phenoxy)-phenyl]-6-(methanesulfonyl-pyrrolidin-3-yl-amino)-benzofuran-3-carboxylic acid methylamide; hydrochloride salt (I-91) and 5-cyclopropyl-2-[4-(4-fluoro-phenoxy)-phenyl]-6-[methanesulfonyl-(1-methanesulfonyl-pyrrolidin-3-yl)-amino]-benzofuran-3-carboxylic acid methylamide (I-94)

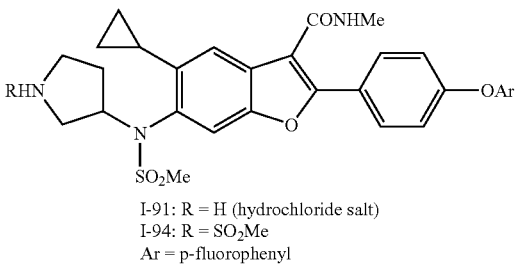

I-91: R = H (hydrochloride salt)
I-94: R = SO$_2$Me
Ar = p-fluorophenyl

3-Iodo-pyrrolidine-1-carboxylic acid tert-butyl ester (52)—To a solution pyrrolidine-1,3-dicarboxylic acid 1-tert-butyl ester (0.2 g, 0.929 mmol, CASRN 59378-75-5), (diacetoxyiodo)-benzene (0.87 g, 2.70 mmol, CASRN 3240-34-4) in CCl$_4$ (30 mL) was added iodine (0.55 g, 2.17 mmol) and the mixture was stirred and irradiated with a 100 W tungsten bulb overnight. The product was partition between DCM and 5% NaHCO$_3$. The aqueous solution was twice extracted with DCM and the combined organic extracts washed with brine, dried (Na$_2$SO$_4$), filtered and evaporated. The crude product was purified on a SiO$_2$ column eluting with 10 and 20% EtOAc/hexane to afford 0.16 g of 52.

I-91 were prepared in accord with the procedure described for I-70 in example 5 except in step 2,3-iodomethyl-oxetane was replaced with 52. The Boc group was removed with 1M HCl in ether in a DCM/MeOH solution (RT overnight). The product was purified by precipitating the product from a MeOH solution with Et$_2$O. I-94 was prepared by contacting I-91 with mesyl chloride and TEA in DCM under standard conditions and was purified on a preparative SiO$_2$ TLC plate developed with 5% acetone/DCM.

EXAMPLE 14

2-[4-(2-Fluoro-phenoxy)-phenyl]-6-(methanesulfonyl-methyl-amino)-5-methyl-benzofuran-3-carboxylic acid methylamide (I-59)

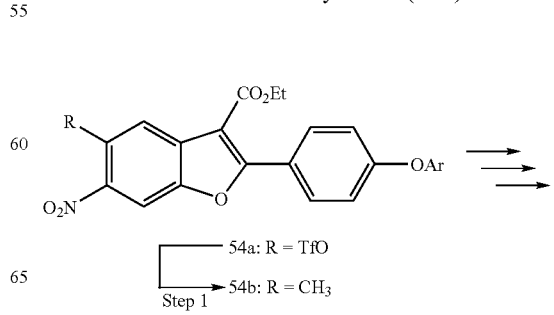

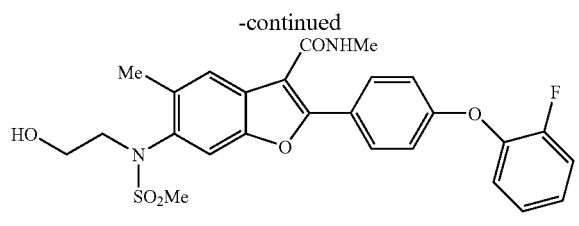

I-59

Ar = o-fluorophenyl

B-3 was converted to ethyl 2-[4-(2-fluoro-phenoxy)-phenyl]-5-isopropoxy-6-nitro-benzofuran-3-carboxylate (56) utilizing the procedure in step 5 of example 3 except p-fluorophenol was replaced with o-fluorophenol. Cleavage of the isopropyl ether and introduction of the triflate ester to afford ethyl 2-[4-(2-fluoro-phenoxy)-phenyl]-6-nitro-5-trifluoromethanesulfonyloxy-benzofuran-3-carboxylate (58) was carried out as described in steps 6 and 7 of example 3.

step 1—A tube was charged with 58 (0.060 g, 0.11 µmol), Pd(PPh$_3$)$_4$ (0.025 g, 0.02 mmol), K$_3$PO$_4$ (0.034 g, 0.11 mmol), trimethylboroxine (0.02 mL, 0.13 mmol) and dioxane (2 mL), sealed and heated at 100° C. for 2 h with stirring. The reaction mixture was cooled, diluted with DCM and filtered through a glass filter. The filtrated was dried and applied to an SiO$_2$ column and eluted with 15% EtOAc/hexane to afford 0.020 g of 54b.

Reduction of the nitro group, sulfonylation and alkylation of the resulting sulfonamide were carried out as described in steps 9 to 11 of example 3. Hydrolysis of the ethyl ester and introduction of the N-methyl amide were carried out as described in steps 12 and 13 of example 3 to afford I-59.

I-55 was prepared from B-4c which was prepared in step 7 of example 3. I-63 was prepared as described for I-55 except in step 11, the alkylating agent was methyl iodide instead of 2-bromo-ethanol and acetone was the solvent.

EXAMPLE 15

5-Cyclopropyl-6-(1,1-dioxo-1λ$^6$-isothiazolidin-2-yl)-2-(4-phenoxy-phenyl)-benzofuran-3-carboxylic acid methylamide (I-82)

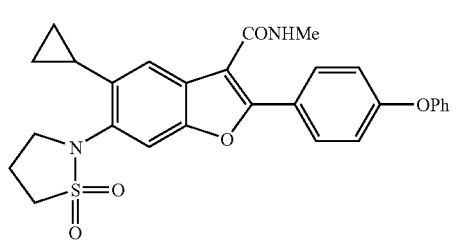

I-82

A solution of B-5a (0.085 g, 0.21 mmol, Ar=phenyl), 3-chloro-propane-1-sulfonyl chloride (0.02 mL, 0.21 mmol, CASRN 1633-82-5), TEA (0.06 mL, 0.42 mmol) and THF (15 mL) was stirred for 5 d, filtered and concentrated in vacuo. The residue was dissolved in EtOH containing NaOEt (0.236 g 3.47 mmol) and the resulting solution heated at reflux for 1 h. The reaction mixture was cooled and evaporated. The crude product was purified by SiO$_2$ chromatography eluting with an EtOAc/hexane gradient (35 to 50% EtOAc) to afford 72 mg of ethyl 5-cyclopropyl-6-(1,1-dibxo-1λ$^6$-isothiazolidin-2-yl)-2-(4-phenoxy-phenyl)-benzofuran-3-carboxylate (59).

Hydrolysis of the ethyl ester and conversion to the amide was carried out as previously described in steps 12 and 13 of example 3 to afford I-82.

I-93 was made analogously except 3-chloro-propane-1-sulfonyl chloride was replaced with 4-chloro-butyl-sulfonyl chloride (CASRN 1633-84-7).

EXAMPLE 16

5-Cyclopropyl-6-(1,1-dioxo-1λ$^6$-[1,2,5]thiadiazolidin-2-yl)-2-(4-phenoxy-phenyl)-benzofuran-3-carboxylic acid methylamide (I-102)

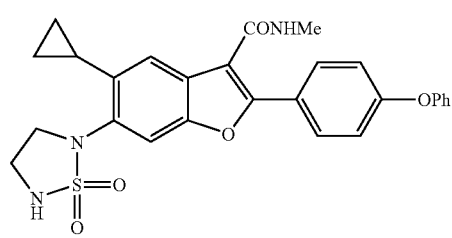

I-102

A solution 2-chloroethyl amine hydrochloride (0.348 g, 3.0 mmol) and sulfuryl chloride (18 mL, 18 mmol) in MeCN (25 mL) was heated overnight at 80° C. then cooled and evaporated to afford N-(2-chloroethyl)-sulfamoyl chloride (60). (P. D. Johnson et al. *Tetrahedron Lett.* 2003 44:5483)

An ether solution of 60 was added dropwise to a solution of B5a (0.500 g, 1.2 mmol, Ar=phenyl), TEA (0.33 mL, 2.4 mmol) and ether (100 mL) cooled to −78° C. After the addition was complete the cooling bath was removed and the reaction was allowed to stir at RT for 4 h, then washed with water, dried (MgSO$_4$) filtered and evaporated. The residue was dissolved in DMSO and K$_2$CO$_3$ (0.166 g, 1.2 mmol) was added and the reaction mixture was stirred for 72 h. The reaction was quenched with H$_2$O and extracted with EtOAc/Et$_2$O (1:1). The organic phase was washed sequentially with H$_2$O and brine, dried (MgSO$_4$), filtered and evaporated. The residue was purified on a SiO$_2$ column eluting with 30% EtOAc/hexane to afford 0.158 g of ethyl 5-cyclopropyl-6-(1,1-dioxo-1λ$^6$-[1,2,5]thiadiazolidin-2-yl)-2-(4-phenoxy-phenyl)-benzofuran-3-carboxylate (62). Hydrolysis of the ethyl ester and conversion to the amide was carried out as previously described in steps 12 and 13 of example 3 to afford I-102.

EXAMPLE 17

5-Cyclopropyl-6-(5-methyl-1,1-dioxo-1λ$^6$-[1,2,5]thiadiazolidin-2-yl)-2-(4-phenoxy-phenyl)-benzofuran-3-carboxylic acid methylamide (I-105)

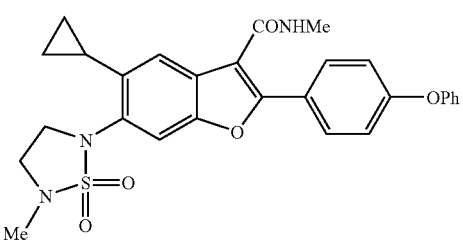

(I-105)

To a solution of 62 (0.058 g, 0.11 mmol) and dry DMF (5 mL) was added sequentially NaH (5 mg, 0.12 mmol, 50% mineral oil dispersion) and MeI (0.08 mL, 0.14 mmol). The reaction mixture was stirred for 15 min then quenched with H₂O and extracted with EtOAc/Et₂O. The organic phase was washed sequentially with H₂O and brine, dried (MgSO₄), filtered and evaporated to afford 30 mg of ethyl 5-cyclopropyl-6-(5-methyl-1,1-dioxo-1λ⁶-[1,2,5]thiadiazolidin-2-yl)-2-(4-phenoxy-phenyl)-benzofuran-3-carboxylate (64). Hydrolysis of the ethyl ester and conversion to the amide was carried out as previously described in steps 12 and 13 of example 3 to afford I-105.

EXAMPLE 18

2-[4-(4-Fluoro-phenoxy)-phenyl]-6-[(2-hydroxy-ethyl)-methanesulfonyl-amino]-benzofuran-3-carboxylic acid methylamide (I-64)

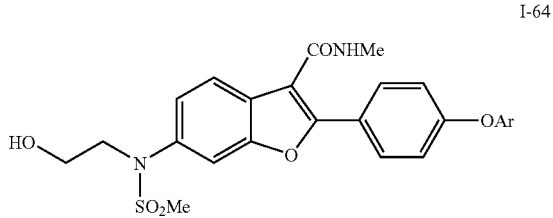

I-64

A tube was charged with B-4c (0.600 g, 1.05 mmol), pinacolborane (0.46, 3.16 mmol), PdCl₂(dppf) (0.171 g, 0.21 mmol), TEA (0.44 mL, 3.16 mmol) and dioxane (10 mL), sealed and heated overnight at 110° C. The tube was cooled and the reaction mixture diluted with Et₂O and DCM and filtered through a glass fritted funnel. The filtrate was washed sequentially with H₂O and brine, dried (MgSO₄), filtered and evaporated. The crude product was purified by SiO₂ chromatography eluting with an EtOAc/hexane gradient (20 to 30% EtOAc) to afford ethyl 6-amino-2-[4-(4-fluoro-phenoxy)-phenyl]-5-(4,4,5,5-tetramethyl-[1,3,2]dioxaborolan-2-yl)-benzofuran-3-carboxylate (66).

Conversion of 66 to I-64 is carried out in accord with the procedure described in steps 11 to 13 of example 3.

EXAMPLE 19

5-Cyclopropyl-6-(3,5-dimethyl-isoxazol-4-yl)-2-(4-phenoxy-phenyl)-benzofuran-3-carboxylic acid methylamide (I-85)

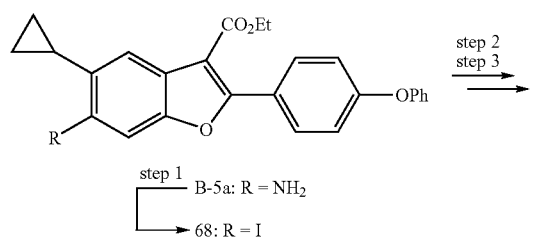

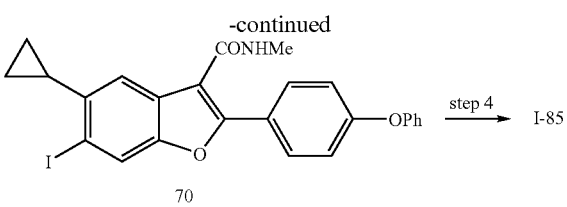

step 1—To a suspension of B-5a in 6 N HCl (10 mL) cooled in an ice bath was added a solution of sodium nitrite (0.100 g) and H₂O (2 mL) and the reaction was stirred at 0° C. for 30 min. The reaction mixture was poured into a mixture of KI (1 g) and EtOAc/H₂O and stirred for 30 min. The organic layer was separated, washed sequentially with aq Na₂S₂O₈ and brine, dried (Na₂SO₄), filtered and evaporated. The crude product was purified by SiO₂ chromatography eluting with an EtOAc/hexane gradient (0 to 10% EtOAc) to afford 0.090 g of 68.

steps 2 & 3—Conversion of 68 to the corresponding N-methyl amide 70 was carried out as described in steps 12 and 13 of example 3.

step 4—A mixture of 70 (0.040 g), 3,5-dimethyl-isoxazol-4-yl boronic acid (0.050 g, CASRN 16114-47-9), Pd(PPh₃)₄ (0.010 g), Na₂CO₃ (10 mg), DCM and MeOH was heated at 120° C. for 30 min. The reaction mixture was cooled and concentrated in vacuo. The residue was dissolved in EtOAc and washed sequentially with H₂O and brine, dried (Na₂SO₄), filtered and evaporated. The crude product was purified by SiO₂ chromatography eluting with an EtOAc/hexane gradient (10 to 30% EtOAc) to afford 30 mg of I-85.

I-101 is prepared analogously except 68 and 3,5-dimethyl-pyrazol-4-yl boronic acid (CASRN 851524-99-7) were coupled with prior to hydrolysis of the ester and conversion of the corresponding acid to the N-methyl amide I-101. The product was purified by first treating the crude product with (Boc)₂O, DMAP and THF, purifying the crude Boc adduct by SiO₂ chromatography eluting with an EtOAc/hexane gradient (0 to 40% EtOAc) and treating the product with TFA and DCM overnight to remove the Boc protecting group.

EXAMPLE 20

5-Cyclopropyl-2-(4-phenoxy-phenyl)-6-(1H-pyrrol-2-yl)-benzofuran-3-carboxylic acid methylamide (I-89) and 5-5-Cyclopropyl-2-(4-phenoxy-phenyl)-6-pyrrolidin-2-yl-benzofuran-3-carboxylic acid methylamideyclopropyl-2-(4-phenoxy-phenyl)-6-pyrrolidin-2-yl-benzofuran-3-carboxylic acid methylamide (I-90)

I-89 was prepared analogously to the procedure in example 19 except in step 4, 70 was coupled with N-Boc-pyrrol-2-yl boronic acid (CASRN 135884-31-0). Purification of the product by SiO₂ chromatography with an EtOAc/hexane gradient (0 to 30% EtOAc) afforded I-89 and the product which retained the Boc group (72).

step 1—A suspension of 72 (0.080 g), Pd/C (15 mg) and EtOAc was shaken in a Paar shaker under a hydrogen atmosphere (50 psi) overnight at RT. The suspension was filtered through CELITE, the pad washed with EtOAc and the filtrate concentrated in vacuo. The crude product was purified by SiO₂ chromatography eluting with an EtOAc/hexane gradient (0 to 30% EtOAc).

The fractions containing 2-[5-cyclopropyl-3-methylcarbamoyl-2-(4-phenoxy-phenyl)-benzofuran-6-yl]-pyrrolidine-1-carboxylic acid tert-butyl ester were combined and concentrated in vacuo. The resulting residue was dissolved in TFA/DCM (2 mL) and stirred overnight at RT. The solvents were removed in vacuo, diluted with EtOAc and washed sequentially H$_2$O, sat'd. NaHCO$_3$ and brine, dried (Na$_2$SO$_4$), filtered and evaporated. The crude product was purified by SiO$_2$ chromatography eluting with a MeOH/DCM gradient (0 to 5% MeOH containing a small amount of ammonia to afford 2 mg of I-90.

EXAMPLE 21

2-[4-(4-Fluoro-phenoxy)-phenyl]-5-methoxy-6-pyrrolidin-2-yl-benzofuran-3-carboxylic acid methylamide (I-111), 6-(1-acetyl-pyrrolidin-2-yl)-2-[4-(4-fluoro-phenoxy)-phenyl]-5-methoxy-benzofuran-3-carboxylic acid methylamide (I-109) and 2-[4-(4-Fluoro-phenoxy)-phenyl]-6-(1-methanesulfonyl-pyrrolidin-2-yl)-5-methoxy-benzofuran-3-carboxylic acid methylamide (I-112)

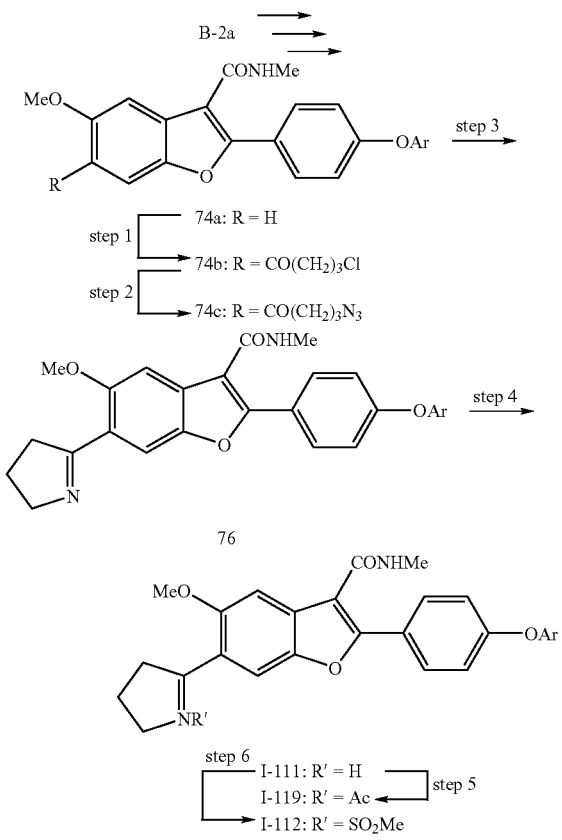

Ar = p-fluoro-phenyl

B-2a is converted to 74a by alkylation of the phenol (MeI/K$_2$CO$_3$), Suzuki coupling with p-fluoro-phenol (as described in example 3, step 5), hydrolysis of the ethyl ester and coupling with methylamine (as described in example 3, steps 12 & 13)

step 1—To a mixture of 74a (0.5 g) and 3-chloro-butyryl chloride (0.30 mL) in DCM (10 mL) cooled in an ice-bath was added AlCl$_3$ (0.400 g) and the resulting mixture stirred at 0° C. for 30 min. The reaction was quenched with ice-water, stirred for 10 min then extracted with DCM. The organic phase was washed sequentially with H$_2$O and brine, dried (Na$_2$SO$_4$), filtered and evaporated to afford 0.4 g of 74b.

step 2—The crude product from step 1 was suspended in DMSO (5 mL) and NaI (0.8 g) and NaN$_3$ (0.8 g) were added and heated overnight at 50° C. The reaction was cooled, diluted with EtOAc and washed sequentially with H$_2$O and brine, dried (Na$_2$SO$_4$), filtered and evaporated to afford 0.4 g of 74c.

step 3—A solution of 74c (0.4 g) was dissolved in EtOAc and PPh$_3$ (0.5 g) was added and the reaction stirred overnight. The resulting solid was collected by filtration to afford 0.15 g of 76.

step 4—To a solution of 76 (0.050 g) in MeOH/HOAc (2:1, 3 mL) was added NaBH$_4$ (0.020 g) and the resulting solution was stirred for 30 min. The reaction was quenched with H$_2$O and extracted with EtOAc, washed sequentially with NaHCO$_3$, H$_2$O and brine, dried (Na$_2$SO$_4$), filtered and evaporated which afford I-111.

step 5—The amine 1-ill was stirred with AcCl, TEA and DCM to afford I-109.

step 6—The amine I-11 was stirred with mesyl chloride, TEA and DCM to afford I-112.

EXAMPLE 22

5-Cyclopropyl-2-[4-(4-fluoro-phenoxy)-phenyl]-6-(1-hydroxy-1-methyl-ethyl)-benzofuran-3-carboxylic acid methylamide (I-110)

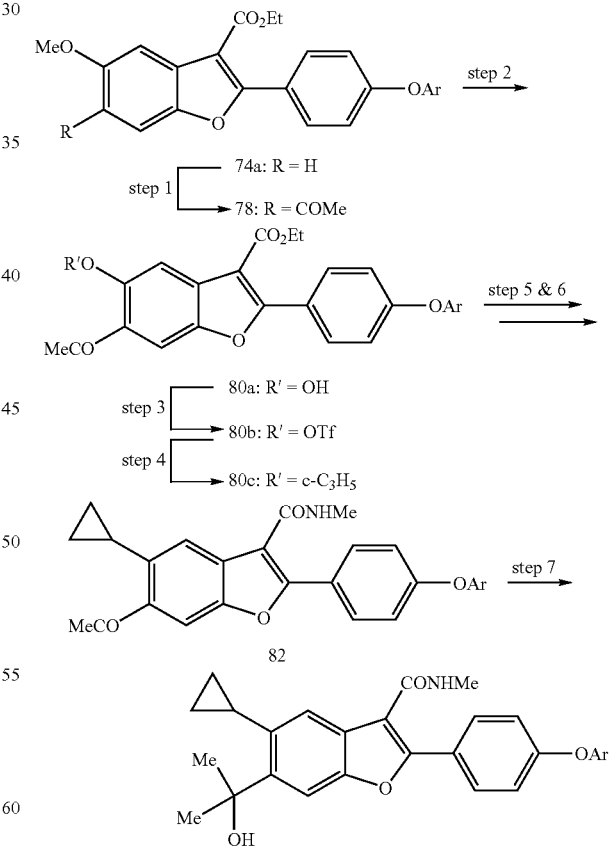

step 1—To a solution of 74a (0.5 g), acetyl chloride (0.35 g) and DCM cooled to

0° C. was added AlCl$_3$ (0.35 g). The reaction mixture was stirred for 15 min and an additional amount of AlCl$_3$ (50 mg)

was added and stirring continued for another 15 min. The reaction was quenched with ice water and the organic phase separated, washed with brine, dried (Na$_2$SO$_4$), filtered and evaporated. The crude product was purified by SiO$_2$ chromatography eluting with an EtOAc/hexane gradient (0 to 25% EtOAc) to afford 0.35 g of 78.

step 2—To a solution of 78 dissolved to DCM (2 mL) was added a solution of BCl$_3$ and DCM (2 mL, 1M solution). The reaction was stirred for 2 h then quenched with ice and diluted with DCM. The organic phase was washed with brine, dried (Na$_2$SO$_4$), filtered and evaporated to afford 80a which was used directly in step 3.

Steps 3-6 were carried out by the procedures described in steps 7, 8, 12 and 13 of example 3 to afford 82.

step 7—To a solution of 82 (50 mg) and dry THF cooled to −78° C. was added a solution of MeMgBr and THF (0.20 mL, 3M solution in THF). The solution was stirred for 20 min then quenched with sat'd. NH$_4$Cl and diluted with EtOAc. The organic phase was washed with brine, dried (Na$_2$SO$_4$), filtered and evaporated. The crude product was purified by SiO$_2$ chromatography eluting with an EtOAc/hexane gradient (0 to 40% EtOAc) to afford 7 mg of I-110.

I-86 is prepared analogously except the starting material was 6-acetyl-5-cyclopropyl-2-(4-phenoxy-phenyl)-benzofuran-3-carboxylic acid methylamide. I-103 and I-104 can be prepared from A-2c by introduction of the p-fluorophenyl by Suzuki coupling with p-fluoro-phenol (see step 5 of example 3), Freidel-Crafts acylation, hydrolysis of the ethyl ester and coupling with methylamine and addition of methyl magnesium bromide as carried described in the current example.

EXAMPLE 23

5-Cyclopropyl-2-[4-(4-fluoro-phenoxy)-phenyl]-6-[(2-methanesulfinyl-ethyl)-methanesulfonyl-amino]-benzofuran-3-carboxylic acid methylamide (I-120)

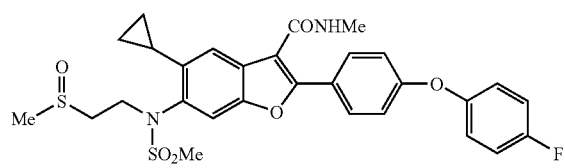

To a solution of I-81 (0.086 g, 0.15 mmol) in MeOH (5 mL) and H$_2$O (1.7 mL) was added OXONE (0.065 g, 0.11 mmol). The reaction was stirred at RT for 30 min then concentrated in vacuo. The residue was partitioned between DCM (40 mL) and 1M NaOH (1 mL). The organic extract was dried (Na$_2$SO$_4$), filtered and evaporated. The crude product was purified on a preparative SiO$_2$ TLC plate developed with 3% MeOH/DCM to afford 30 mg if I-120 as a yellow solid. I-121 was prepared analogously by oxidation of I-113

EXAMPLE 24

6-[(2-Hydroxy-ethyl)-methanesulfonyl-amino]-5-methoxy-2-[4-(pyridin-2-yloxy)-phenyl]-benzofuran-3-carboxylic acid methylamide (I-127)

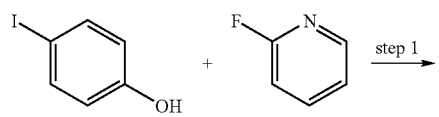

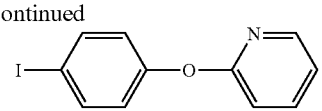

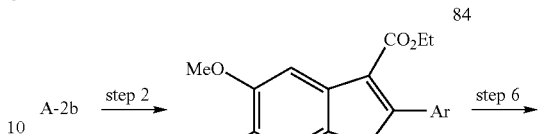

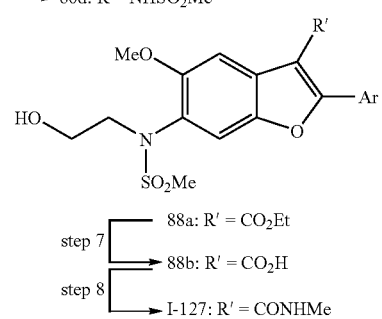

Ar = 4-(pyridin-2-yloxy)-phenyl step 1—A solution of 4-iodo-phenol (1.0 g), 2-fluoro-pyridine (1.0 g), K$_2$CO$_3$ (1 g) in DMSO was heated overnight at 90° C. The reaction was cooled, partitioned between EtOAc and H$_2$O. The organic phase was washed sequentially with H$_2$O and brine, dried (Na$_2$SO$_4$), filtered and concentrated in vacuo. The crude product was purified by SiO$_2$ chromatography eluting with hexane to afford 0.4 g of 84.

step 2—A mixture of A-2b (1.2 g), 84 (0.4 g), Pd(PPh$_3$)$_4$ (0.100 g), Na$_2$CO$_3$ (1.5 g), MeOH (40 mL) and DCM (10 mL) was heated at reflux overnight. The reaction mixture was cooled and filtered through CELITE. The CELITE was washed with EtOAc and the filtrated sequentially washed with H$_2$O and brine, dried (Na$_2$SO$_4$) filtered and evaporated. The crude product was purified by SiO$_2$ chromatography eluting with an EtOAc/hexane gradient (0 to 20% EtOAc) to afford 0.3 g of 86b.

Steps 3-8 can be carried out utilizing the procedures described in the corresponding steps 3 to 8 in example 1 to afford I-127.

EXAMPLE 25

2-[6-(4-Fluoro-phenoxy)-pyridin-3-yl]-6-[(2-hydroxy-ethyl)-methanesulfonyl-amino]-5-methoxy-benzofuran-3-carboxylic acid methylamide (I-125)

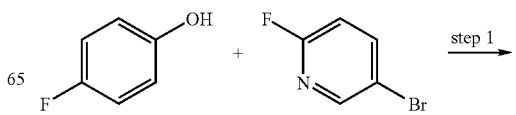

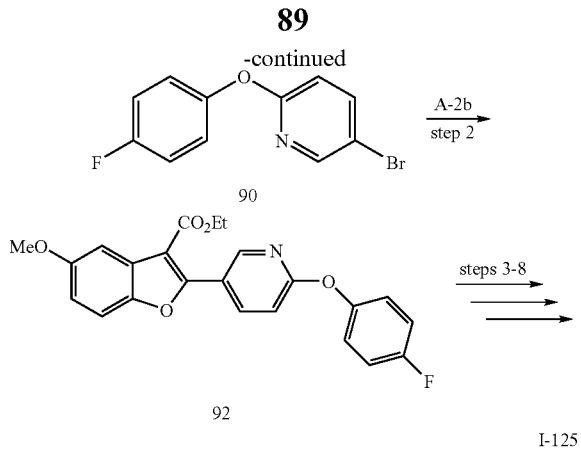

step 1—A mixture of 4-fluoro-phenol (1.0 g), 5-bromo-2-fluoro-pyridine (1.5 g), K$_2$CO$_3$ (1.0 g) in DMSO (20 mL) was heated at 100° C. overnight. The reaction mixture was cooled and diluted with EtOAc. The resulting solution was washed sequentially with H$_2$O and brine, dried (Na$_2$SO$_4$), filtered and evaporated. The product was purified by SiO$_2$ chromatography eluting with an EtOAc/hexane gradient (0 to 5% EtOAc) to afford 1.2 g of 90.

step 2—A mixture of 90 (1.2 g), A-2b (2 g), Pd(0)(PPh$_3$)$_4$ (200 mg), K$_2$CO$_3$ (2.0 g) in MeOH (50 mL) and DCM (10 mL) was heated at reflux overnight. The reaction mixture was cooled and filtered through CELITE and the pad was washed well with 1:1 EtOAc/hexane and EtOAc. The filtrates were combined, washed sequentially with H$_2$O and brine, dried (Na$_2$SO$_4$), filtered and evaporated to afford 0.77 g of 92.

The conversion of 92 to I-125 (steps 3-8) was carried out by the corresponding procedures described in example 1.

EXAMPLE 26

2-[6-(4-Fluoro-phenylamino)-pyridin-3-yl]-6-[(2-hydroxy-ethyl)-methanesulfonyl-amino]-5-methoxy-benzofuran-3-carboxylic acid methylamide (I-126)

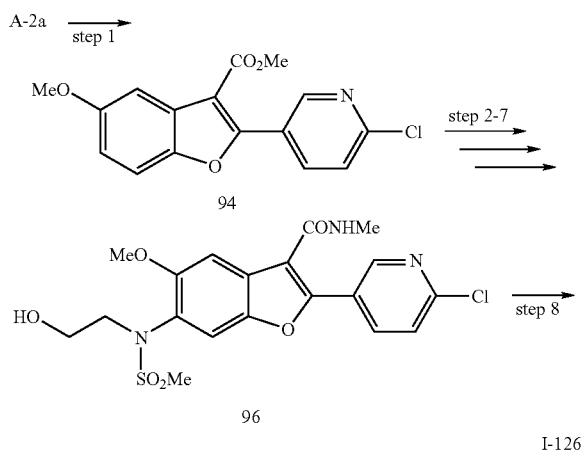

step 1—To a solution of A-2a (2 g, 9 mmol), trimethyl borate (1.12 g, 10 mmol) in dry THF (5 mL) cooled to −78° C. was added 1.2 equivalents of 2M solution of lithium diisopropylamide and THF. After 10 min an aliquot was quenched and showed starting material remained. Additional 5 mL of LDA was and after an additional 10 min the reaction appeared complete. The reaction was quenched with water and the solution extracted with EtOAc. The aqueous layer was acidified with 6N HCl and twice extracted with EtOAc. The combined extracts were washed sequentially with water and brine, dried (Na$_2$SO$_4$), filtered and concentrated. The residue was dissolved in MeOH (50 mL) and DCM (10 mL) and 2-chloro-5-iodo-pyridine (2.0 g), Pd(0)(PPh$_3$)$_4$ (0.200 g) and Na$_2$CO$_3$ (2 g) were added. The reaction was heated at reflux overnight then cooled and filtered through CELITE and the pad washed with DCM, The filtrate was concentrated and the resulting solid triturated with hexane and collected by filtration. The product was purified by SiO$_2$ chromatography eluting with an EtOAc/hexane gradient (0 to 20% EtOAc) to afford 0.5 g of 94.

Steps 2-5 comprising nitration of the 6 position of 94, reduction of the nitro group, mesylation and alkylation of the resulting sulfonamide and steps 6 and 7 comprising hydrolysis of the ester and conversion the resulting carboxylic acid to the N-methyl amide were carried out as described in steps 3 to 8 of example 1 to afford 96.

step 8—Formation of the aryl pyridinyl amine was carried out by coupling 96 and p-fluoro aniline as described in step 9 of example 1. The product was purified by SiO$_2$ chromatography eluting with a MeOH/DCM gradient (0 to 3% MeOH) to afford 4 mg of I-126).

EXAMPLE 25

HCV NS5B RNA Polymerase Activity

The enzymatic activity of HCV polymerase (NS5B570n-Con1) was measured as the incorporation of radiolabeled nucleotide monophosphates into acid insoluble RNA products. Unincorporated radiolabeled substrate was removed by filtration and scintillant was added to the washed and dried filter plate containing radiolabeled RNA product. The amount of RNA product generated by NS5B570-Con1 at the end of the reaction was directly proportional to the amount of light emitted by the scintillant.

The N-terminal 6-histidine tagged HCV polymerase, derived from HCV Con1 strain, genotype 1b (NS5B570n-Con1) contains a 21 amino acid deletion at the C-terminus relative to the full-length HCV polymerase and was purified from *E. coli* strain BL21 (DE) pLysS. The construct, containing the coding sequence of HCV NS5B Con1 (GenBank accession number AJ242654) was inserted into the plasmid construct pETI 7b, downstream of a T7 promoter expression cassette and transformed into *E. coli*. A single colony was grown overnight as a starter culture and later used inoculate 10 L of LB media supplemented with 100 μg/mL ampicillin at 37° C. Protein expression was induced by the addition of 0.25 mM isopropyl-β-D-thiogalactopyranoside (IPTG) when optical density at 600 nM of the culture was between 0.6 and 0.8 and cells were harvested after 16 to 18 h at 30° C. NS5B570n-Con1 was purified to homogeneity using a three-step protocol including subsequent column chromatography on Ni-NTA, SP-Sepharose HP and Superdex 75 resins.

Each 50 μl enzymatic reaction contained 20 nM RNA template derived from the complementary sequence of the Internal Ribosome Entry Site (cIRES), 20 nM NS5B570n-Con1 enzyme, 0.5 μCi of tritiated UTP (Perkin Elmer catalog no. TRK-412; specific activity: 30 to 60 Ci/mmol; stock solution concentration from 7.5×10-5 M to 20.6×10-6 M), 1 μM each ATP, CTP, and GTP, 40 mM Tris-HCl pH 8.0, 40 mM NaCl, 4 mM DTT (dithiothreitol), 4 mM MgCl2, and 5 μl of compound serial diluted in DMSO. Reaction mixtures were assembled in 96-well filter plates (cat #MADVN0B, Millipore Co.) and incubated for 2 h at 30° C. Reactions were stopped by addition of 10% final (v/v) trichloroacetic acid and incubated for 40 min at 4° C. Reactions were filtered, washed with 8 reaction volumes of 10% (v/v) trichloroacetic acetic acid, 4 reaction volumes of 70% (v/v) ethanol, air dried, and 25 µl of scintillant (Microscint 20, Perkin-Elmer) was added to each reaction well.

The amount of light emitted from the scintillant was converted to counts per minute (CPM) on a Topcount® plate reader (Perkin-Elmer, Energy Range: Low, Efficiency Mode Normal, Count Time: 1 min, Background Subtract: none, Cross talk reduction: Off).

Data was analyzed in Excel® (Microsoft®) and ActivityBase® (idbsg). The reaction in the absence of enzyme was used to determine the background signal, which was subtracted from the enzymatic reactions. Positive control reactions were performed in the absence of compound, from which the background corrected activity was set as 100% polymerase activity. All data was expressed as a percentage of the positive control. The compound concentration at which the enzyme-catalyzed rate of RNA synthesis was reduced by 50% ($IC_{50}$) was calculated by fitting $$Y = \% \text{ Min} + \frac{(\% \text{ Max} - \% \text{ Min})}{\left[1 + \frac{X}{(IC_{50})^S}\right]} \quad (i)$$

equation (t) to the data.where "Y" corresponds to the relative enzyme activity (in %), "% Min" is the residual relative activity at saturating compound concentration, "% Max" is the relative maximum enzymatic activity, "X" corresponds to the compound concentration, and "S" is the Hill coefficient (or slope).

EXAMPLE 26

HCV Replicon Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The *Renilla luciferase* gene was introduced into the first open reading frame of a genotype 1b replicon construct NK5.1 (N. Krieger et al., *J. Virol.* 2001 75(10):4614), immediately after the internal ribosome entry site (IRES) sequence, and fused with the neomycin phosphotransferase (NPTII) gene via a self-cleavage peptide 2A from foot and mouth disease virus (M. D. Ryan & J. Drew, *EMBO* 1994 13(4):928-933). After in vitro transcription the RNA was electroporated into human hepatoma Huh7 cells, and G418-resistant colonies were isolated and expanded. Stably selected cell line 2209-23 contains replicative HCV subgenomic RNA, and the activity of *Renilla luciferase* expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation or due to cell death.

HCV replicon cells (2209-23), which express *Renilla luciferase* reporter, were cultured in Dulbecco's MEM (Invitrogen cat no. 10569-010) with 5% fetal bovine serum (FBS, Invitrogen cat. no. 10082-147) and plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and luciferase activity was measured by using the *R. luciferase* Assay system (Promega cat no. E2820). All the reagents described in the following paragraph were included in the manufacturer's kit, and the manufacturer's instructions were followed for preparations of the reagents. The cells were washed once with 100 µl of phosphate buffered saline (pH 7.0) (PBS) per well and lysed with 20 µl of 1× *R. luciferase* Assay lysis buffer prior to incubation at room temperature for 20 min. The plate was then inserted into the Centro LB 960 microplate luminometer (Berthold Technologies), and 100 µl of *R. luciferase* Assay buffer was injected into each well and the signal measured using a 2-second delay, 2-second measurement program. $IC_{50}$, the concentration of the drug required for reducing replicon level by 50% in relation to the untreated cell control value, can be calculated from the plot of percentage reduction of the luciferase activity vs. drug concentration as described above.

WST-1 reagent from Roche Diagnostic (cat no. 1644807) was used for the cytotoxicity assay. Ten microliter of WST-1 reagent was added to each well of the transparent plates including wells that contain media alone as blanks. Cells were then incubated for 2 h at 37° C., and the OD value was measured using the MRX Revelation microtiter plate reader (Lab System) at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration as described above.

TABLE II

| Compound Number | Polymerase Assay IC50 (µM) | HCV Replicon Activity IC50 (µM) | Cytotoxic Activity CC50 (µM) |
|---|---|---|---|
| I-1 | 0.005 | 0.043 | 30.6 |
| I-69 | 0.018 | 0.01 | 4.6 |
| I-116 | | 0.004 | |

EXAMPLE 27

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound according to formula I wherein:

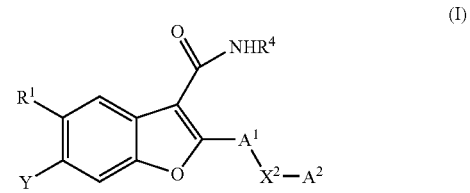

$A^1$ is phenylene or pyridinylene;

$A^2$ is phenyl or pyridinyl either optionally substituted with 1 to 3 groups independently selected from the group consisting of halogen, $C_{1-6}$ alkyl, $C_{1-6}$ haloalkyl, cyano and $C_{1-6}$ alkoxy;

$R^1$ is hydrogen, $C_{1-10}$ alkyl, $C_{3-7}$ cycloalkyl, $C_{1-10}$ alkoxy or halogen;

Y is $NR^2R^3$, $C_{1-6}$ hydroxyalkyl, $C_{1-6}$ acyl or heteroaryl selected from the group consisting of pyrrolyl, pyrazolyl or isoxazolyl said heteroaryl optionally substituted by one or two groups selected from $C_{1-3}$ alkyl, $C_{1-3}$ haloalkyl, $C_{1-3}$ alkoxy, halogen or pyrrolidinyl wherein the nitrogen atom is optionally substituted by $C_{1-6}$ acyl or $C_{1-6}$ alkylsulfonyl;

either (i) $R^2$ is (a) hydrogen,
  (b) $C_{1-10}$ alkyl,
  (c) $C_{1-10}$ alkyl substituted by one to four groups selected independently in each occurrence from hydroxy, $NR^{7b}R^{8b}$, $C_{1-3}$ alkoxy, halogen or cyano;
  (d) $R^{11}S(=O)_m[C(R^5)_2]_{1-6}$ wherein $R^{11}$ is $C_{1-6}$ alkyl or $NR^{7c}R^{8c}$;
  (e) $C_{1-3}$ alkyl-$S(=O)_2NH$—$[C(R^5)_2]_{1-6}$;
  (f) $R^{7b}R^{8b}NC(=O)$—$[C(R^5)_2]_{1-6}$;
  (g) $C_{3-6}$ cycloalkyl optionally substituted by —OH, $C_{1-3}$ alkoxy or —$NR^{7b}R^{8b}$;
  (h) heterocyclyl;
  (i) heterocyclyl-$C_{1-6}$alkyl;
  (j) heteroaryl-$C_{1-6}$ alkyl;
  (k) $C_{1-6}$ acyl optionally substituted with $C_{1-6}$ alkylsulfonyl;
  (l) $(CH_2)_pCOX^3$ wherein p is one to six and $X^3$ is hydroxy, $C_{1-6}$ alkoxy or $NR^{7c}R^{8c}$;
  wherein said heterocyclyl moiety is oxetanyl, tetrahydrofuranyl, tetrahydropyranyl, azetidinyl, pyrrolidinyl or piperidinyl, oxazolidin-2-on-4-yl and said heteroaryl moiety is pyridinyl or pyrimidinyl and said heterocyclyl or heteroaryl groups are optionally substituted with optionally substituted by —OH, $C_{1-3}$ alkoxy, $C_{1-3}$ alkyl or —$NR^{7b}R^{8b}$ $R^3$ is hydrogen, $C_{1-10}$ alkyl, $S(=O)_2R^6$, $S(=O)_2NR^{7a}R^{8a}$, $C_{1-6}$ acyl or $C(=O)NR^{7a}R^{8a}$; or, (ii) $R^2$ and $R^3$ together are $(CH_2)_2X^1(CH_2)_2$, $(CH_2)_{3-4}S(=O)_2$, $(CH_2)_{2-3}NR^{10}S(=O)_2$;

$R^4$ and $R^5$ are independently in each occurrence hydrogen or $C_{1-6}$ alkyl;

$R^6$ is $C_{1-6}$ alkyl or $C_{3-7}$ cycloalkyl;

$R^{7a}$ and $R^{8a}$ are (i) independently hydrogen, $C_{1-6}$ alkyl, $C_{1-6}$ hydroxyalkyl $C_{1-6}$ haloalkyl or (ii) $R^{7a}$ and $R^{8a}$ together are $(CH_2)_2X^1(CH_2)_2$;

$R^{7b}$, $R^{8b}$ and $R^{10}$ are independently hydrogen, $C_{1-6}$ alkyl, $C_{1-6}$ acyl or $C_{1-6}$ alkylsulfonyl, $R^{7c}$ and $R^{8c}$ are independently hydrogen or $C_{1-3}$ alkyl;

$R^9$ is hydrogen $C_{1-3}$ acyl, $C_{1-3}$ alkylsulfonyl or $C_{1-3}$ alkyl;

$R^{10}$ is hydrogen or $C_{1-6}$ alkyl;

$X^1$ is —O—.—$NR^9$—, —$S(O)_m$—, $(CH_2)_n$;

$X^2$ is $NHR^5$ or O;

m and n are independently in each occurrence an integer from 0 to 2; or, pharmaceutically acceptable salts thereof.

2. A compound according to claim 1 wherein Y is $NR^2R^3$ and $A^1$ is para-phenylene.

3. A compound according to claim 2 wherein $R^3$ is $S(=O)_2 R^6$ and $R^6$ is $C_{1-6}$ alkyl.

4. A compound according to claim 3 wherein $R^2$ is $R^{11}S(=O)_m[C(R^5)_2]_{1-6}$ and $R^{11}$ is $C_{1-6}$ alkyl or $NR^7NR^{8c}$.

5. A compound according to claim 4 wherein $R^{11}$ is $C_{1-6}$ alkyl.

6. A compound according to claim 3 wherein $R^2$ is $C_{1-10}$ alkyl substituted by one to four groups selected independently in each occurrence from hydroxy, $NR^{7b}R^{8b}$, $C_{1-3}$ alkoxy, halogen or cyano.

7. A compound according to claim 6 wherein $R^2$ is $C_{1-10}$ alkyl substituted by a hydroxy or a $NR^{7b}R^{8b}$ moiety.

8. A compound according to claim 7 wherein $R^2$ is a $C_{1-10}$ alkyl substituted by a $NR^{7b}R^{8b}$ moiety wherein is $R^{7b}$ is $C_{1-6}$ alkylsulfonyl or $C_{1-6}$ acyl.

9. A compound according to claim 3 wherein $R^2$ is optionally substituted heterocyclyl or heterocyclyl-$C_{1-6}$ alkyl.

10. A compound according to claim 1 wherein Y is $NR^2R^3$ and $A^1$ is meta-phenylene.

11. A compound according to claim 1 wherein Y is $NR^2R^3$ and $A^2$ is optionally substituted 2-pyridinyl or 3-pyridinyl.

12. A compound according to claim 1 wherein Y is $NR^2R^3$ and $A^1$ is pyridinylene.

13. A compound according to claim 1 which compound is selected from the group consisting of:

6-[(2-hydroxy-ethyl)-methanesulfonyl-amino]-5-methoxy-2-(4-phenylamino-phenyl)-benzofuran-3-carboxylic acid methylamide;

2-[4-(4-fluoro-phenylamino)-phenyl]-6-[(2-hydroxy-ethyl)-methanesulfonyl-amino]-5-methoxy-benzofuran-3-carboxylic acid methylamide;

2-[4-(4-chloro-phenylamino)-phenyl]-6-[(2-hydroxy-ethyl)-methanesulfonyl-amino]-5-methoxy-benzofuran-3-carboxylic acid methylamide;

6-[(2-hydroxy-ethyl)-methanesulfonyl-amino]-5-methoxy-2-(4-phenoxy-phenyl)-benzofuran-3-carboxylic acid methylamide;

2-[4-(2-fluoro-phenylamino)-phenyl]-6-[(2-hydroxy-ethyl)-methanesulfonyl-amino]-5-methoxy-benzofuran-3-carboxylic acid methylamide;

6-[(2-hydroxy-ethyl)-methanesulfonyl-amino]-2-[4-(4-isopropyl-phenylamino)-phenyl]-5-methoxy-benzofuran-3-carboxylic acid methylamide;

6-[(2-hydroxy-ethyl)-methanesulfonyl-amino]-5-methoxy-2-[4-(3-methoxy-phenylamino)-phenyl]-benzofuran-3-carboxylic acid methylamide;

2-[4-(4-fluoro-phenoxy)-phenyl]-6-[(2-hydroxy-ethyl)-methanesulfonyl-amino]-5-methoxy-benzofuran-3-carboxylic acid methylamide;

2-[4-(2-fluoro-phenoxy)-phenyl]-6-[(2-hydroxy-ethyl)-methanesulfonyl-amino]-5-methoxy-benzofuran-3-carboxylic acid methylamide;

2-[4-(3,4-difluoro-phenylamino)-phenyl]-6-[(2-hydroxy-ethyl)-methanesulfonyl-amino]-5-methoxy-benzofuran-3-carboxylic acid methylamide;

6-[(2-hydroxy-ethyl)-methanesulfonyl-amino]-5-methoxy-2-[4-(4-trifluoromethyl-phenylamino)-phenyl]-benzofuran-3-carboxylic acid methylamide;

2-[4-(3-cyano-phenylamino)-phenyl]-6-[(2-hydroxy-ethyl)-methanesulfonyl-amino]-5-methoxy-benzofuran-3-carboxylic acid methylamide;

2-[4-(4-cyano-phenylamino)-phenyl]-6-[(2-hydroxy-ethyl)-methanesulfonyl-amino]-5-methoxy-benzofuran-3-carboxylic acid methylamide;

2-[4-(2,4-difluoro-phenylamino)-phenyl]-6-[(2-hydroxy-ethyl)-methanesulfonyl-amino]-5-methoxy-benzofuran-3-carboxylic acid methylamide;

2-[4-(3-chloro-4-fluoro-phenylamino)-phenyl]-6-[(2-hydroxy-ethyl)-methanesulfonyl-amino]-5-methoxy-benzofuran-3-carboxylic acid methylamide;

2-[4-(3,5-difluoro-phenylamino)-phenyl]-6-[(2-hydroxy-ethyl)-methanesulfonyl-amino]-5-methoxy-benzofuran-3-carboxylic acid methylamide;

6-(ethyl-methanesulfonyl-amino)-2-[4-(4-fluoro-phenylamino)-phenyl]-5-methoxy-benzofuran-3-carboxylic acid methylamide;

6-(ethyl-methanesulfonyl-amino)-2-[4-(2-fluoro-phenylamino)-phenyl]-5-methoxy-benzofuran-3-carboxylic acid methylamide;

2-[4-(4-chloro-phenoxy)-phenyl]-6-[(2-hydroxy-ethyl)-methanesulfonyl-amino]-5-methoxy-benzofuran-3-carboxylic acid methylamide;

6-[(2-hydroxy-ethyl)-methanesulfonyl-amino]-5-methoxy-2-(4-p-tolylamino-phenyl)-benzofuran-3-carboxylic acid methylamide;

2-[4-(2,3-difluoro-phenylamino)-phenyl]-6-[(2-hydroxy-ethyl)-methanesulfonyl-amino]-5-methoxy-benzofuran-3-carboxylic acid methylamide;

2-[4-(2,3-difluoro-phenoxy)-phenyl]-6-[(2-hydroxy-ethyl)-methanesulfonyl-amino]-5-methoxy-benzofuran-3-carboxylic acid methylamide;

6-(ethyl-methanesulfonyl-amino)-2-[4-(2-fluoro-phenoxy)-phenyl]-5-methoxy-benzofuran-3-carboxylic acid methylamide;

6-(ethyl-methanesulfonyl-amino)-2-[4-(4-fluoro-phenoxy)-phenyl]-5-methoxy-benzofuran-3-carboxylic acid methylamide;

2-[4-(2,6-difluoro-phenylamino)-phenyl]-6-[(2-hydroxy-ethyl)-methanesulfonyl-amino]-5-methoxy-benzofuran-3-carboxylic acid methylamide;

2-[4-(3-fluoro-phenoxy)-phenyl]-6-[(2-hydroxy-ethyl)-methanesulfonyl-amino]-5-isopropoxy-benzofuran-3-carboxylic acid methylamide;

2-[4-(4-chloro-phenoxy)-phenyl]-6-[(2-hydroxy-ethyl)-methanesulfonyl-amino]-5-isopropoxy-benzofuran-3-carboxylic acid methylamide;

6-[(2-hydroxy-ethyl)-methanesulfonyl-amino]-5-isopropoxy-2-(4-phenylamino-phenyl)-benzofuran-3-carboxylic acid methylamide;

2-[4-(3-fluoro-phenylamino)-phenyl]-6-[(2-hydroxy-ethyl)-methanesulfonyl-amino]-5-isopropoxy-benzofuran-3-carboxylic acid methylamide;

2-[4-(4-chloro-phenylamino)-phenyl]-6-[(2-hydroxy-ethyl)-methanesulfonyl-amino]-5-isopropoxy-benzofuran-3-carboxylic acid methylamide;

2-[4-(4-fluoro-phenylamino)-phenyl]-6-[(2-hydroxy-ethyl)-methanesulfonyl-amino]-5-isopropoxy-benzofuran-3-carboxylic acid methylamide;

5-cyclopropyl-2-[4-(4-fluoro-phenoxy)-phenyl]-6-[(2-hydroxy-ethyl)-methanesulfonyl-amino]-benzofuran-3-carboxylic acid methylamide;

5-cyclopropyl-6-[(2-hydroxy-ethyl)-methanesulfonyl-amino]-2-(4-phenoxy-phenyl)-benzofuran-3-carboxylic acid methylamide;

2-[4-(2-fluoro-phenylamino)-phenyl]-6-[(2-hydroxy-ethyl)-methanesulfonyl-amino]-5-isopropoxy-benzofuran-3-carboxylic acid methylamide;

2-[4-(4-fluoro-phenoxy)-phenyl]-6-(methanesulfonyl-methyl-amino)-5-methoxy-benzofuran-3-carboxylic acid methylamide;

2-[4-(2-fluoro-phenoxy)-phenyl]-6-(methanesulfonyl-methyl-amino)-5-methoxy-benzofuran-3-carboxylic acid methylamide;

2-[4-(2,4-difluoro-phenoxy)-phenyl]-6-[(2-hydroxy-ethyl)-methanesulfonyl-amino]-5-methoxy-benzofuran-3-carboxylic acid methylamide;

2-[4-(3-chloro-phenoxy)-phenyl]-6-[(2-hydroxy-ethyl)-methanesulfonyl-amino]-5-methoxy-benzofuran-3-carboxylic acid methylamide;

2-[4-(2,4-difluoro-phenoxy)-phenyl]-6-[(2-hydroxy-ethyl)-methanesulfonyl-amino]-5-isopropoxy-benzofuran-3-carboxylic acid methylamide;

5-cyclopropyl-2-[4-(4-fluoro-phenoxy)-phenyl]-6-methanesulfonylamino-benzofuran-3-carboxylic acid methylamide;

5-cyclopropyl-2-[4-(4-fluoro-phenoxy)-phenyl]-6-(methanesulfonyl-methyl-amino)-benzofuran-3-carboxylic acid methylamide;

5-cyclopropyl-6-(ethyl-methanesulfonyl-amino)-2-[4-(4-fluoro-phenoxy)-phenyl]-benzofuran-3-carboxylic acid methylamide;

6-[(2-hydroxy-ethyl)-methanesulfonyl-amino]-5-methoxy-2-[4-(pyridin-3-ylamino)-phenyl]-benzofuran-3-carboxylic acid methylamide;

2-[4-(4-fluoro-phenoxy)-phenyl]-6-methanesulfonylamino-5-methoxy-benzofuran-3-carboxylic acid methylamide;

6-[(2-hydroxy-ethyl)-methanesulfonyl-amino]-5-methoxy-2-[4-(pyridin-2-ylamino)-phenyl]-benzofuran-3-carboxylic acid methylamide;

2-[4-(2-chloro-phenoxy)-phenyl]-6-[(2-hydroxy-ethyl)-methanesulfonyl-amino]-5-methoxy-benzofuran-3-carboxylic acid methylamide;

2-[4-(3,4-difluoro-phenoxy)-phenyl]-6-[(2-hydroxy-ethyl)-methanesulfonyl-amino]-5-methoxy-benzofuran-3-carboxylic acid methylamide;

2-[4-(3-chloro-phenoxy)-phenyl]-6-[(2-hydroxy-ethyl)-methanesulfonyl-amino]-5-isopropoxy-benzofuran-3-carboxylic acid methylamide;

2-[4-(3-cyano-phenoxy)-phenyl]-6-[(2-hydroxy-ethyl)-methanesulfonyl-amino]-5-methoxy-benzofuran-3-carboxylic acid methylamide;

2-[4-(4-cyano-phenoxy)-phenyl]-6-[(2-hydroxy-ethyl)-methanesulfonyl-amino]-5-methoxy-benzofuran-3-carboxylic acid methylamide;

2-[4-(2-chloro-phenoxy)-phenyl]-6-[(2-hydroxy-ethyl)-methanesulfonyl-amino]-5-isopropoxy-benzofuran-3-carboxylic acid methylamide;

2-[4-(5-fluoro-pyridin-2-ylamino)-phenyl]-6-[(2-hydroxy-ethyl)-methanesulfonyl-amino]-5-methoxy-benzofuran-3-carboxylic acid methylamide;

2-[4-(3,4-difluoro-phenoxy)-phenyl]-6-[(2-hydroxy-ethyl)-methanesulfonyl-amino]-5-isopropoxy-benzofuran-3-carboxylic acid methylamide;

2-[6-(4-fluoro-phenoxy)-pyridin-3-yl]-6-[(2-hydroxy-ethyl)-methanesulfonyl-amino]-5-methoxy-benzofuran-3-carboxylic acid methylamide;

5-ethyl-2-[4-(4-fluoro-phenoxy)-phenyl]-6-[(2-hydroxy-ethyl)-methanesulfonyl-amino]-benzofuran-3-carboxylic acid methylamide;

5-ethyl-2-[4-(4-fluoro-phenoxy)-phenyl]-6-(methanesulfonyl-methyl-amino)-benzofuran-3-carboxylic acid methylamide;

2-[6-(4-fluoro-phenylamino)-pyridin-3-yl]-6-[(2-hydroxy-ethyl)-methanesulfonyl-amino]-5-methoxy-benzofuran-3-carboxylic acid methylamide;

6-[(2-amino-ethyl)-methanesulfonyl-amino]-2-[4-(4-fluoro-phenoxy)-phenyl]-5-methoxy-benzofuran-3-carboxylic acid methylamide; TFA salt 6-[acetyl-(2-amino-ethyl)-amino]-2-[4-(4-fluoro-phenoxy)-phenyl]-5-methoxy-benzofuran-3-carboxylic acid methylamide; TFA salt 2-[4-(4-fluoro-phenoxy)-phenyl]-6-[(2-hydroxy-ethyl)-methanesulfonyl-amino]-5-methyl-benzofuran-3-carboxylic acid methylamide;

5-cyclopropyl-2-[4-(4-fluoro-phenoxy)-phenyl]-6-[methanesulfonyl-(tetrahydro-pyran-4-ylmethyl)-amino]-benzofuran-3-carboxylic acid methylamide;

5-cyclopropyl-2-[4-(4-fluoro-phenoxy)-phenyl]-6-[methanesulfonyl-(2-methoxy-ethyl)-amino]-benzofuran-3-carboxylic acid methylamide;

5-cyclopropyl-2-[4-(2,4-difluoro-phenoxy)-phenyl]-6-[(2-hydroxy-ethyl)-methanesulfonyl-amino]-benzofuran-3-carboxylic acid methylamide;

2-[4-(2-fluoro-phenoxy)-phenyl]-6-(methanesulfonyl-methyl-amino)-5-methyl-benzofuran-3-carboxylic acid methylamide;

5-cyclopropyl-2-[4-(4-fluoro-phenoxy)-phenyl]-6-[methanesulfonyl-(tetrahydro-furan-3-ylmethyl)-amino]-benzofuran-3-carboxylic acid methylamide;

5-cyclopropyl-2-[4-(2-fluoro-phenoxy)-phenyl]-6-[(2-hydroxy-ethyl)-methanesulfonyl-amino]-benzofuran-3-carboxylic acid methylamide;

5-cyclopropyl-2-[4-(4-fluoro-phenylamino)-phenyl]-6-[(2-hydroxy-ethyl)-methanesulfonyl-amino]-benzofuran-3-carboxylic acid methylamide;

2-[4-(4-fluoro-phenoxy)-phenyl]-6-(methanesulfonyl-methyl-amino)-5-methyl-benzofuran-3-carboxylic acid methylamide;

2-[4-(4-fluoro-phenoxy)-phenyl]-6-[(2-hydroxy-ethyl)-methanesulfonyl-amino]-benzofuran-3-carboxylic acid methylamide;

2-[4-(2-fluoro-phenoxy)-phenyl]-6-[(2-hydroxy-ethyl)-methanesulfonyl-amino]-5-propyl-benzofuran-3-carboxylic acid methylamide;

5-chloro-2-[4-(4-fluoro-phenoxy)-phenyl]-6-(methanesulfonyl-methyl-amino)-benzofuran-3-carboxylic acid methylamide;

4-({5-Cyclopropyl-2-[4-(4-fluoro-phenoxy)-phenyl]-3-methylcarbamoyl-benzofuran-6-yl}-methyl-amino)-butyric acid methyl ester 5-cyclopropyl-2-[4-(4-fluoro-phenoxy)-phenyl]-6-[(2-hydroxy-propyl)-methanesulfonyl-amino]-benzofuran-3-carboxylic acid methylamide;

6-[(3-amino-propyl)-methanesulfonyl-amino]-5-cyclopropyl-2-[4-(4-fluoro-phenoxy)-phenyl]-benzofuran-3-carboxylic acid methylamide; HCl salt 5-cyclopropyl-2-[4-(4-fluoro-phenoxy)-phenyl]-6-(methanesulfonyl-oxetan-3-ylmethyl-amino)-benzofuran-3-carboxylic acid methylamide;
5-cyclopropyl-2-[4-(4-fluoro-phenoxy)-phenyl]-6-(methanesulfonyl-pyridin-4-ylmethyl-amino)-benzofuran-3-carboxylic acid methylamide;
5-cyclopropyl-2-[4-(4-fluoro-phenoxy)-phenyl]-6-[methanesulfonyl-(tetrahydro-pyran-4-yl)-amino]-benzofuran-3-carboxylic acid methylamide;
6-(carbamoylmethyl-methanesulfonyl-amino)-5-cyclopropyl-2-[4-(4-fluoro-phenoxy)-phenyl]-benzofuran-3-carboxylic acid methylamide;
6-[(2-amino-ethyl)-methanesulfonyl-amino]-5-cyclopropyl-2-[4-(4-fluoro-phenoxy)-phenyl]-benzofuran-3-carboxylic acid methylamide; HCl salt
6-(azetidin-3-yl-methanesulfonyl-amino)-5-cyclopropyl-2-[4-(4-fluoro-phenoxy)-phenyl]-benzofuran-3-carboxylic acid methylamide; HCl salt
5-cyclopropyl-2-[4-(4-fluoro-phenoxy)-phenyl]-6-(methanesulfonyl-piperidin-4-yl-amino)-benzofuran-3-carboxylic acid methylamide; HCl salt
5-cyclopropyl-6-morpholin-4-yl-2-(4-phenoxy-phenyl)-benzofuran-3-carboxylic acid methylamide;
5-cyclopropyl-2-[4-(4-fluoro-phenoxy)-phenyl]-6-[(2-hydroxy-2-methyl-propyl)-methanesulfonyl-amino]-benzofuran-3-carboxylic acid methylamide;
6-[(2-acetylamino-ethyl)-methanesulfonyl-amino]-5-cyclopropyl-2-[4-(4-fluoro-phenoxy)-phenyl]-benzofuran-3-carboxylic acid methylamide;
5-cyclopropyl-2-[4-(4-fluoro-phenoxy)-phenyl]-6-[methanesulfonyl-(2-methanesulfonylamino-ethyl)-amino]-benzofuran-3-carboxylic acid methylamide;
5-cyclopropyl-2-[4-(4-fluoro-phenoxy)-phenyl]-6-[methanesulfonyl-(2-methylsulfanyl-ethyl)-amino]-benzofuran-3-carboxylic acid methylamide;
5-cyclopropyl-6-(1,1-dioxo-1$\lambda^6$-isothiazolidin-2-yl)-2-(4-phenoxy-phenyl)-benzofuran-3-carboxylic acid methylamide;
5-cyclopropyl-2-[4-(4-fluoro-phenoxy)-phenyl]-6-[methanesulfonyl-(2-methanesulfonyl-ethyl)-amino]-benzofuran-3-carboxylic acid methylamide;
5-cyclopropyl-2-[4-(4-fluoro-phenoxy)-phenyl]-6-[methanesulfonyl-(tetrahydro-furan-3-yl)-amino]-benzofuran-3-carboxylic acid methylamide;
5-cyclopropyl-6-(3,5-dimethyl-isoxazol-4-yl)-2-(4-phenoxy-phenyl)-benzofuran-3-carboxylic acid methylamide;
6-acetyl-5-cyclopropyl-2-(4-phenoxy-phenyl)-benzofuran-3-carboxylic acid methylamide;
5-cyclopropyl-2-[4-(4-fluoro-phenoxy)-phenyl]-6-[methanesulfonyl-(3-methyl-oxetan-3-ylmethyl)-amino]-benzofuran-3-carboxylic acid methylamide;
5-cyclopropyl-2-[4-(4-fluoro-phenoxy)-phenyl]-6-(methanesulfonyl-pyrimidin-5-ylmethyl-amino)-benzofuran-3-carboxylic acid methylamide;
5-cyclopropyl-2-(4-phenoxy-phenyl)-6-(1H-pyrrol-2-yl)-benzofuran-3-carboxylic acid methylamide;
5-cyclopropyl-2-(4-phenoxy-phenyl)-6-pyrrolidin-2-yl-benzofuran-3-carboxylic acid methylamide;
5-cyclopropyl-2-[4-(4-fluoro-phenoxy)-phenyl]-6-(methanesulfonyl-pyrrolidin-3-yl-amino)-benzofuran-3-carboxylic acid methylamide; HCl salt
6-[(4-amino-butyl)-methanesulfonyl-amino]-5-cyclopropyl-2-[4-(4-fluoro-phenoxy)-phenyl]-benzofuran-3-carboxylic acid methylamide; HCl salt
5-cyclopropyl-6-(1,1-dioxo-1$\lambda^6$-[1,2]thiazinan-2-yl)-2-(4-phenoxy-phenyl)-benzofuran-3-carboxylic acid methylamide;
5-cyclopropyl-2-[4-(4-fluoro-phenoxy)-phenyl]-6-[methanesulfonyl-(1-methanesulfonyl-pyrrolidin-3-yl)-amino]-benzofuran-3-carboxylic acid methylamide;
6-[(2-amino-1-methyl-ethyl)-methanesulfonyl-amino]-5-cyclopropyl-2-[4-(4-fluoro-phenoxy)-phenyl]-benzofuran-3-carboxylic acid methylamide; HCl salt
6-[(3-cyano-propyl)-methanesulfonyl-amino]-5-cyclopropyl-2-[4-(4-fluoro-phenoxy)-phenyl]-benzofuran-3-carboxylic acid methylamide;
6-[(3-amino-2-hydroxy-propyl)-methanesulfonyl-amino]-5-cyclopropyl-2-[4-(4-fluoro-phenoxy)-phenyl]-benzofuran-3-carboxylic acid methylamide; HCl salt 6-[(4-amino-cyclohexyl)-methanesulfonyl-amino]-5-cyclopropyl-2-[4-(4-fluoro-phenoxy)-phenyl]-benzofuran-3-carboxylic acid methylamide;
5-cyclopropyl-2-[4-(4-fluoro-phenoxy)-phenyl]-6-[(4-hydroxy-cyclohexyl)-methanesulfonyl-amino]-benzofuran-3-carboxylic acid methylamide;
5-cyclopropyl-2-[4-(4-fluoro-phenoxy)-phenyl]-6-[(4-hydroxy-cyclohexyl)-methanesulfonyl-amino]-benzofuran-3-carboxylic acid methylamide;
5-cyclopropyl-6-(3,5-dimethyl-1H-pyrazol-4-yl)-2-(4-phenoxy-phenyl)-benzofuran-3-carboxylic acid methylamide;
5-cyclopropyl-6-(1,1-dioxo-1$\lambda^6$-[1,2,5]thiadiazolidin-2-yl)-2-(4-phenoxy-phenyl)-benzofuran-3-carboxylic acid methylamide;
2-[4-(4-fluoro-phenoxy)-phenyl]-6-(1-hydroxy-1-methyl-ethyl)-5-methoxy-benzofuran-3-carboxylic acid methylamide;
6-acetyl-2-[4-(4-fluoro-phenoxy)-phenyl]-5-methoxy-benzofuran-3-carboxylic acid methylamide;
5-cyclopropyl-6-(5-methyl-1,1-dioxo-1$\lambda^6$-[1,2,5]thiadiazolidin-2-yl)-2-(4-phenoxy-phenyl)-benzofuran-3-carboxylic acid methylamide;
5-cyclopropyl-2-[4-(4-fluoro-phenoxy)-phenyl]-6-[(3-hydroxy-propyl)-methanesulfonyl-amino]-benzofuran-3-carboxylic acid methylamide;
6-[(2-amino-3-hydroxy-propyl)-methanesulfonyl-amino]-5-cyclopropyl-2-[4-(4-fluoro-phenoxy)-phenyl]-benzofuran-3-carboxylic acid methylamide; HCl salt
5-cyclopropyl-2-[4-(4-fluoro-phenoxy)-phenyl]-6-[methanesulfonyl-(2-oxo-oxazolidin-4-ylmethyl)-amino]-benzofuran-3-carboxylic acid methylamide;
6-(1-acetyl-pyrrolidin-2-yl)-2-[4-(4-fluoro-phenoxy)-phenyl]-5-methoxy-benzofuran-3-carboxylic acid methylamide;
5-cyclopropyl-2-[4-(4-fluoro-phenoxy)-phenyl]-6-(1-hydroxy-1-methyl-ethyl)-benzofuran-3-carboxylic acid methylamide;
2-[4-(4-fluoro-phenoxy)-phenyl]-5-methoxy-6-pyrrolidin-2-yl-benzofuran-3-carboxylic acid methyl amide;
2-[4-(4-fluoro-phenoxy)-phenyl]-6-(1-methanesulfonyl-pyrrolidin-2-yl)-5-methoxy-benzofuran-3-carboxylic acid methylamide;
5-cyclopropyl-2-[4-(4-fluoro-phenoxy)-phenyl]-6-[methanesulfonyl-(3-methylsulfanyl-propyl)-amino]-benzofuran-3-carboxylic acid methylamide;
5-cyclopropyl-2-[4-(4-fluoro-phenoxy)-phenyl]-6-[methanesulfonyl-(3-methanesulfonyl-propyl)-amino]-benzofuran-3-carboxylic acid methylamide;

6-[(3-amino-2,2-difluoro-propyl)-methanesulfonyl-amino]-5-cyclopropyl-2-[4-(4-fluoro-phenoxy)-phenyl]-benzofuran-3-carboxylic acid methylamide; HCl salt 5-cyclopropyl-2-[4-(4-fluoro-phenoxy)-phenyl]-6-[methanesulfonyl-(3-methanesulfonylamino-propyl)-amino]-benzofuran-3-carboxylic acid methyl amide;

5-cyclopropyl-2-[4-(4-fluoro-phenoxy)-phenyl]-6-{methanesulfonyl-[3-(methanesulfonyl-methyl-amino)-propyl]-amino}-benzofuran-3-carboxylic acid methyl amide;

5-cyclopropyl-2-[4-(4-fluoro-phenoxy)-phenyl]-6-[methanesulfonyl-(3-sulfamoyl-propyl)-amino]-benzofuran-3-carboxylic acid methylamide;

5-cyclopropyl-2-[4-(4-fluoro-phenoxy)-phenyl]-6-[methanesulfonyl-(2-sulfamoyl-ethyl)-amino]-benzofuran-3-carboxylic acid methylamide;

5-cyclopropyl-2-[4-(4-fluoro-phenoxy)-phenyl]-6-[(2-methanesulfinyl-ethyl)-methanesulfonyl-amino]-benzofuran-3-carboxylic acid methylamide;

5-cyclopropyl-2-[4-(4-fluoro-phenoxy)-phenyl]-6-[(3-methanesulfinyl-propyl)-methanesulfonyl-amino]-benzofuran-3-carboxylic acid methylamide;

4-({5-Cyclopropyl-2-[4-(4-fluoro-phenoxy)-phenyl]-3-methylcarbamoyl-benzofuran-6-yl}-methanesulfonyl-amino)-butyric acid;

6-[(2-hydroxy-ethyl)-methanesulfonyl-amino]-5-methoxy-2-[4-(pyridin-2-yloxy)-phenyl]-benzofuran-3-carboxylic acid methylamide; or, pharmaceutically acceptable salts thereof.

14. A method for treating a disease caused by the Hepatitis C Virus (HCV) infection comprising administering to a patient in need thereof, a therapeutically effective quantity of a compound according to claim 1.

15. The method of claim 14 further co-comprising administering at least one immune system modulator and/or at least one antiviral agent that inhibits replication of HCV.

16. The method of claim 13 wherein the immune system modulator is an interferon, interleukin, tumor necrosis factor or colony stimulating factor.

17. The method of claim 16 wherein the immune system modulator is an interferon or chemically derivatized interferon.

18. The method of claim 15 wherein the antiviral compound is selected from the group consisting of a HCV protease inhibitor, another HCV polymerase inhibitor, a HCV helicase inhibitor, a HCV primase inhibitor and a HCV fusion inhibitor.

19. A method of inhibiting replication of HCV infection in a cell comprising treating the cell with a compound of claim 1.

20. A pharmaceutical composition comprising a therapeutically effective quantity of a compound according to claim 1 admixed with at least one pharmaceutically acceptable carrier, diluent or excipient.

* * * * *